(12) United States Patent
Kamboj et al.

(10) Patent No.: US 7,919,484 B2
(45) Date of Patent: *Apr. 5, 2011

(54) COMBINATION THERAPY

(75) Inventors: Rajender Kamboj, Burnaby (CA);
Michael D. Winther, Vancouver (CA);
Robert Fraser, Vancouver (CA);
Mikhail Chafeev, Burnaby (CA);
Sultan Chowdhury, Surrey (CA);
Jian-Min Fu, Burnaby (CA); Duanjie Hou, Burnaby (CA); Shifeng Liu, Port Coquitlam (CA); Vandna Raina, Vancouver (CA); Mehran Seid Bagherzadeh, North Vancouver (CA);
Serguei Sviridov, Burnaby (CA);
Kashinath Sadalapure, Edmonton (CA); Shaoyi Sun, Vancouver (CA);
Vishnumurthy Kodumuru, Burnaby (CA); Nagasree Chakka, Burnaby (CA); Zaihui Zhang, Vancouver (CA);
Melwyn Abreo, Jamul (CA); Mikhail A. Kondratenko, San Diego, CA (US);
Daniel F. Harvey, San Diego, CA (US);
Cindy J. Hudson, Buena Park, CA (US);
Wenbao Li, San Diego, CA (US); Chi Tu, San Diego, CA (US); Sengen Sun, San Diego, CA (US); Mark W. Holladay, San Diego, CA (US); Heinz W. Gschwend, Santa Rosa, CA (US)

(73) Assignee: Xenon Pharmaceuticals Inc., Burnaby, British Columbia (CA)

( * ) Notice: Subject to any disclaimer, the term of this patent is extended or adjusted under 35 U.S.C. 154(b) by 279 days.

This patent is subject to a terminal disclaimer.

(21) Appl. No.: 11/815,739

(22) PCT Filed: Feb. 8, 2006

(86) PCT No.: PCT/US2006/004383
§ 371 (c)(1),
(2), (4) Date: Jan. 26, 2009

(87) PCT Pub. No.: WO2006/086445
PCT Pub. Date: Aug. 17, 2006

(65) Prior Publication Data
US 2009/0131447 A1    May 21, 2009

Related U.S. Application Data

(60) Provisional application No. 60/651,584, filed on Feb. 9, 2005.

(51) Int. Cl.
*A61K 31/501* (2006.01)
*C07D 211/34* (2006.01)

(52) U.S. Cl. .............. 514/183; 544/238; 544/252.02
(58) Field of Classification Search ............ 514/252.02;
544/238
See application file for complete search history.

(56) References Cited

U.S. PATENT DOCUMENTS 7,335,658 B2 * 2/2008 Chakka et al. ............ 514/252.02
2004/0122033 A1   6/2004 Nargund et al.

FOREIGN PATENT DOCUMENTS

| WO | WO 98/01446 | * | 1/1998 |
| WO | 2004/047746 | | 6/2004 |
| WO | 2006/034315 | | 3/2006 |

OTHER PUBLICATIONS

Pickavance et al. (Br-J-Pharmacol. Dec. 1999; 128(7): 1570-6, (Abstract only).*
Virk et al. Obesity Reviews 5(3) 167-170, (Abstract only).*
Office Action issued by the Pakistan Patent Office on Mar. 25, 2008, in related Pakistan Patent Application No. 97/2006 (12 Pages).
Office Action issued May 20, 2009, by the Canadian Intellectual Property Office in related-Canadian Patent Application No. 2,597,067 (3 pages).
English translation of a Rejection Decision (Office Action) issued Jun. 9, 2010, by the State Intellectual Property Office of The People's Republic of China, in related Chinese Patent Application No. CN-200680009724.6 (6 pages).
Official Action issued Sep. 13, 2010, by the Japan Patent Office in related Japan Patent Application No. JP-2007-555181, with partial English translation (11 pages).

* cited by examiner

*Primary Examiner* — Brandon J Fetterolf
*Assistant Examiner* — Shirley V Gembeh
(74) *Attorney, Agent, or Firm* — Osha • Liang LLP

(57) ABSTRACT

This invention is directed to the use of SCD-1 inhibitors of the formula (I): where x, y, V, W, G, J, L, M, R2, R3, R5, R5a, R6, R6a, R7, R7a, R8 and R8a are defined herein, in combination with other drug therapies to treat adverse weight gain.

18 Claims, 1 Drawing Sheet

COMBINATION THERAPY

FIELD OF THE INVENTION

The present invention relates to methods for treating adverse weight gain associated with drug therapies. More particularly, the invention relates to the use of an SCD-1 inhibitor in combination with drug therapies, particularly drug therapies for diabetes, to treat the adverse weight gain.

BACKGROUND OF THE INVENTION

Adverse weight gain is a consistently documented side effect associated with many different types of drug therapies. It is not known precisely how many of these drugs there are. A good list provided by Dr. George L. Blackburn, an obesity authority at Harvard University, includes more than 50 common drugs for the treatment of a range of disorders and conditions. (see, Blackburn, G L. Weight gain and antipsychotic medication. J. Clin. Psychiatry 2000; 61(8S): 36-42). The major therapeutic areas with currently known drugs associated with adverse weight gain include, but are not limited to: anti-diabetics, anti-depressants, anti-psychotics, anti-convulsants, anti-epileptics, oral contraceptives, cancer therapy, preventative migraine therapy, therapy for systemic inflammatory conditions, endometriosis therapy, osteoporosis therapy, hair growth therapy, and HIV therapy. Drug-induced adverse weight gain can be severe or mild depending on the treatment. The adverse weight gain can lead to overweight, and obesity (i.e. BMI>30 kg/m$^2$), and may exacerbate many health problems, both independently and in associations with other diseases, and clearly associated with increased morbidity and mortality.

Adverse weight gain ranks among the main reasons these patient populations stop taking some medications (i.e. poor compliance) or contributes to their reluctance to start such treatment in the first place. This side effect presents a serious problem for those who urgently need to treat health problems that are often times far more dangerous than weight gain. Switching to another drug with a lower risk of adverse weight gain is an alternative approach, although this carries a risk of loss of clinical effectiveness. In some cases, the drugs that will most benefit the subject also have the highest incidence of side effects, particularly undesirable side effects such as adverse weight gain. Often times, however, no other appropriate treatments are available.

Therefore, there is a continuing need for new methods of treating adverse weight gain associated with drug therapies. Nowhere is this need more urgently felt than with people who suffer from diabetes mellitus ('diabetes'). The majority of people who develop diabetes, especially types 2 diabetes, either are or have been obese. That means any additional weight gain would exacerbate their diabetes and contribute to the development or progression of obesity-related complications such as hypertension, dyslipidemia, coronary heart disease, stroke, gallbladder disease, osteoarthritis, sleep apnea, and respiratory problems, metabolic syndrome, and endometrial, breast, prostate, and colon cancers, just to name a few.

Diabetes affects an estimated 16 million people in the United States, 90% of whom suffer from type 2 diabetes, formerly referred to as Non-insulin Dependent Diabetes Mellitus, which is a serious, life-threatening disease. (see, Malinowski, J, Rosiglitazone in the Treatment of Type 2 Diabetes Mellitus: A Critical Review, Clin. Therap. 22, 10:1151-1168 (2000)). Type 2 diabetes is the fourth leading cause of death in the United States and a major contributor to blindness, chronic renal failure, and foot and leg amputations in adults. (see, U.S. Department of Health and Human Services. Diabetes Statistics, Bethesda, Md., National Diabetes Information Clearinghouse, October 1995, NIH Publication, 96-236.) Sufferers of type 2 diabetes, presents as a spectrum of metabolic abnormalities relative insulin deficiency and prominent inability to utilize the insulin that is produced by their bodies (i.e. insulin resistance).

The current approach to management of drug therapy in patients with type 2 diabetes is to start with oral drugs. In the United States, there are five classes of drugs that are approved for the treatment of type 2 diabetes and are set out in Table 1.

TABLE 1

Different classes of anti-diabetic drugs

| Drug | Side Effects |
|---|---|
| Sulfonylureas, including first generation (e.g., tolbutamide) and second generation (e.g., glyburide) sulfonylureas. | Sulfonylurea therapy is usually associated with weight gain due to hyperinsulinemia. |
| Biguanides - metformin (e.g. Glucovance ®) | Metformin reduces plasma glucose via inhibition of hepatic glucose production and increase of muscle glucose uptake. It also reduces plasma triglyceride and LDL-cholesterol levels. |
| Alpha-glucosidase inhibitors - acarbose (e.g. Precose ®) | The major side effects are gas, bloating, and diarrhea. |
| Thiazolidinediones troglitazone (e.g. Resulin ®), rosiglitazone (e.g. Avandia ®) and pioglitazone ®. | The major side effects are weight gain and an increase in LDL-cholesterol levels. |
| Meglitinides - Repaglinide (e.g. Prandin ®) | Weight gain, gastrointestinal disturbances, and hypoglycemia are common side effects. |

Patients with type 2 diabetes often become less responsive to a single class of drugs over time, so that combination therapy of two or more of the classes of drugs is often needed for adequate control of blood glucose levels. Many of these anti-diabetic drugs cause adverse weight gain, as indicated above. That means many drug therapy for diabetes would likely involve one or more of the classes of drugs associated with adverse weight gain. Further, insulin is usually added when glycemic control is suboptimal at maximal doses of the oral drug. Weight gain is a well-documented common side effect of insulin. (see, Sinha A, et al., Effect of insulin on body composition in patients with insulin-dependent and non-insulin-dependent diabetes. Diabetes Med 1996; 13:40-46.)

Weight loss drugs for the treatment of obesity include orlisat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. &:189-98) and phentermine (Douglas, A. et al. (1983) Int. J. Obes. 7:591-5). However, the side effects of these drugs and anti-obesity agents may limit their use. Dexfenfluramine was withdrawn from the market because of suspected heart valvulopathy; orlistat is limited by gastrointestinal side effects; and the use of sibutramine is limited by its cardiovascular side effects which have led to reports of deaths and its withdrawal from the market in Italy.

Recently, it has been suggested in PCT published patent application WO 04/018041 that a combination therapy of fibrate, an activator of peroxisome proliferators activated receptor alpha agonists ("PPAR-α"), and the Thiazolidinediones class of drugs, specifically rosiglitazone, would off-set some of the adverse weight gain associated with the treatment of the drugs alone or in combination therapy with other anti-diabetic therapies. The combination therapy of fibrate and rosiglitazone is not useful if the patient is taking cholesterollowering statins such as Lipitor™, Zocor™, and Crestor™. Combined statin-fibrate therapy appears to increase the risk of rhabdomyolysis and severe myopathy and should only be undertaken with extreme caution (see, Shek, A. et al, Statin-fibrate combination therapy; The Annals of Pharmacotherapy: Vol. 35, No. 7, pp. 908-917 (2001)). PCT published patent application WO 04/110375 discloses another combination therapy for treating obesity by administering to a subject in need thereof a composition comprising an anti-obesity agent and an anti-diabetic agent.

Being that adverse weight gain is one of the top contributors to discontinuing medications, it is a side effect that must be dealt with effectively. The absence of a method to treat the adverse weight gain continues to be a major medical challenge, particularly for people with diabetes. Thus, there clearly remains an unmet medical need for treatments of diseases, with therapeutics that do not have the side effect of adverse weight gain.

The present invention addresses this problem by providing a new method for treating the adverse weight gain associated with drug therapies, particularly drug therapies for diabetes, comprising administering to a subject in need thereof a therapeutically effective amount of an SCD-1 inhibitor, in conjunction with a pharmaceutically acceptable diluent or carrier. Subjects with drug-induced adverse weight gain treated with an SCD-1 inhibitor are expected to gain less weight than those treated with the drug alone. As a result, the combination therapy is more likely to result in the subjects continuing with the treatment and ameliorate other medical complications often associated with such adverse weight gain. Further, it is an object of this invention to provide a pharmaceutical composition for use in treating the adverse weight gain associated with drug therapies.

BRIEF SUMMARY OF THE INVENTION

The present invention relates to the discovery that SCD-1 inhibitors have the beneficial property of reducing the adverse weight gain associated with a drug therapy.

In one aspect, the invention relates to a method for treating adverse weight gain associated with a drug therapy, comprising administering to a subject in need thereof therapeutically effective amounts of an SCD-1 inhibitor, in conjunction with a pharmaceutically acceptable diluent or carrier. Preferably, the subject is a mammal, such as a human being.

In one embodiment, the drug therapy is selected from the group consisting of anti-diabetics, anti-depressants, anti-psychotics, anti-convulsants, anti-epileptics, oral contraceptives, cancer therapy, preventative migraine therapy, therapy for systemic inflammatory conditions, endometriosis therapy, osteoporosis therapy, hair growth therapy, and HIV therapy.

In a class of this embodiment, the anti-diabetic drugs useful in the invention is selected from the group consisting of a sulfonylurea, a meglitinide, a PPAR-γ agonists, and insulin. Preferably, the PPAR-γ agonists may be selected from rosiglitazone and pioglitazone. In another class of this embodiment, the anti-depressant useful in the invention is selected from the group consisting of selective serotonin reuptake inhibitors, monoamine oxidase inhibitors, and tricyclic inhibitors. In another class of this embodiment, the anti-psychotic useful in the invention is selected from second generation anti-psychotics. In another class of this embodiment, the cancer therapy useful in the invention is chemotherapy or hormone replacement therapy.

In another embodiment, the drug therapy and the SCD-1 inhibitor are administered together. Alternatively, the drug therapy and the SCD-1 inhibitor are administered sequentially.

In a further embodiment, the therapeutically effect amounts of the SCD-1 inhibitor is about 0.01 mg/kg to about 500 mg/kg, preferably about 0.05 mg/kg to about 100 mg/kg, preferably about 0.20 mg/kg to about 50 mg/kg, preferably about 0.50 mg/kg to about 20 mg/kg, preferably about 1.0 mg/kg to about 2.0 mg/kg per day. Preferably, the SCD-1 inhibitor is effective to inhibit or reverse the adverse weight gain.

In another aspect of the invention, the SCD-1 inhibitor is a compound having the formula (I):

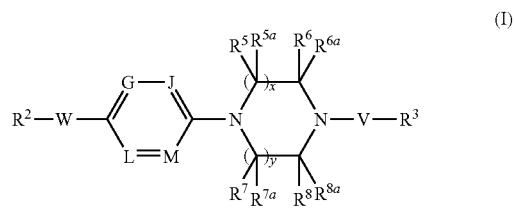

wherein:
x and y are each independently 1, 2 or 3;
W is a direct bond, —N(R$^1$)C(O)—, —C(O)N(R$^1$)—, —OC(O)N(R$^1$)—, —N(R$^1$)C(O)N(R$^1$)—, —O—, —N(R$^1$)—, —S(O)$_t$— (where t is 0, 1 or 2), —N(R$^1$)S(O)$_p$— (where p is 1 or 2), —S(O)$_p$N(R$^1$)— (where p is 1 or 2), —C(O)—, —OS(O)$_2$N(R$^1$)—, —OC(O)—, —C(O)O—, —N(R$^1$)C(O)O—, —NR$^1$C(=NR$^{1a}$)NR$^1$—, —NR$^1$C(=S) NR$^1$—, or —C(=NR$^{1a}$)NR$^1$—;
V is —C(O)—, —C(O)O—, —C(S)—, —C(O)N(R$^1$)—, —S(O)$_t$— (where t is 0, 1 or 2), —S(O)$_p$N(R$^1$)— (where p is 1 or 2), —C(R$^{10}$)H—, —N(R$^1$)—, —C(=NR$^{1a}$)—, or —O—;
G, J, L and M are each independently selected from —N= or —C(R$^4$)=; provided that at most two of G, J, L and M are —N=,
each R$^1$ is independently selected from the group consisting of hydrogen, C$_1$-C$_{12}$alkyl, C$_2$-C$_{12}$hydroxyalkyl, C$_4$-C$_{12}$cycloalkylalkyl and C$_7$-C$_{19}$aralkyl;
each R$^{1a}$ is independently selected from the group consisting of hydrogen, C$_1$-C$_{12}$alkyl, C$_4$-C$_{12}$cycloalkylalkyl, C$_7$-C$_{19}$aralkyl, OR$^1$, and cyano;
R$^2$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl, and C$_3$-C$_{12}$heteroarylalkyl;
or R$^2$ is a multi-ring structure having 2 to 4 rings wherein the rings are independently selected from the group consisting of cycloalkyl, heterocyclyl, aryl and heteroaryl and where some or all of the rings may be fused to each other;
R$^3$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl and C$_3$-C$_{12}$heteroarylalkyl;
or R$^3$ is a multi-ring structure having 2 to 4 rings wherein the rings are independently selected from the group consisting of cycloalkyl, heterocyclyl, aryl and heteroaryl and where some or all of the rings may be fused to each other;

each $R^4$ is independently selected from hydrogen, fluoro, chloro, methyl, methoxy, trifluoromethyl, cyano, nitro or —$N(R^9)_2$;

each $R^5$, $R^{5a}$, $R^6$, $R^{6a}$, $R^7$, $R^{7a}$, $R^8$ and $R^{8a}$ is independently selected from hydrogen or $C_1$-$C_3$alkyl;

or $R^5$ and $R^{5a}$ together, or $R^6$ and $R^{6a}$ together, or $R^7$ and $R^{7a}$ together, or $R^8$ and $R^{8a}$ together are an oxo group, provided that when V is —C(O)—, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

or one of $R^5$, $R^{5a}$, $R^6$, and $R^{6a}$ together with one of $R^7$, $R^{7a}$, $R^8$ and $R^{8a}$ form an alkylene bridge, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

$R^{10}$ is hydrogen or $C_1$-$C_3$alkyl; and each $R^9$ is independently selected from hydrogen or $C_1$-$C_6$alkyl;

provided that when G, J and L are each —C($R^4$) where each $R^4$ is hydrogen, and M is —N=, and x is 1 or 2 and y is 1; W cannot be —N($R^1$)C(O)—;

a stereoisomer, enantiomer or tautomer thereof, a pharmaceutically acceptable salt thereof.

In another aspect, the invention relates to a method of treating, controlling or preventing obesity in a subject at risk for obesity, comprising administration of (a) a therapeutically effective amount of an SCD-1 inhibitor, and pharmaceutically acceptable salts and esters thereof; and (b) a therapeutically effective amount of a drug therapy having a side effect of adverse weight gain, and pharmaceutically acceptable salts and esters thereof.

In another aspect, the invention relates to a method of treating diabetes while mitigating the effect adverse weight gain side associated with PPAR-γ agonist treatment comprising administration of a therapeutically effective amount of an SCD-1 inhibitor, or a pharmaceutically acceptable salt thereof, and a therapeutically effective amount of a PPAR-γ agonist, or a pharmaceutically acceptable salt thereof, to a subject in need of such treatment.

The invention is also concerned with the use of (a) a therapeutically effective amount of a SCD-1 inhibitor and pharmaceutically acceptable salts and esters thereof, and (b) a therapeutically effective amount of a therapeutic agent, for the manufacture of a medicament useful for the treatment of a side effect of adverse weight gain.

The invention also relates to a pharmaceutical composition comprising therapeutically effective amounts of a drug therapy having a side effect of adverse weight gain and an SCD-1 inhibitor.

DETAILED DESCRIPTION OF THE INVENTION

Figure 1:
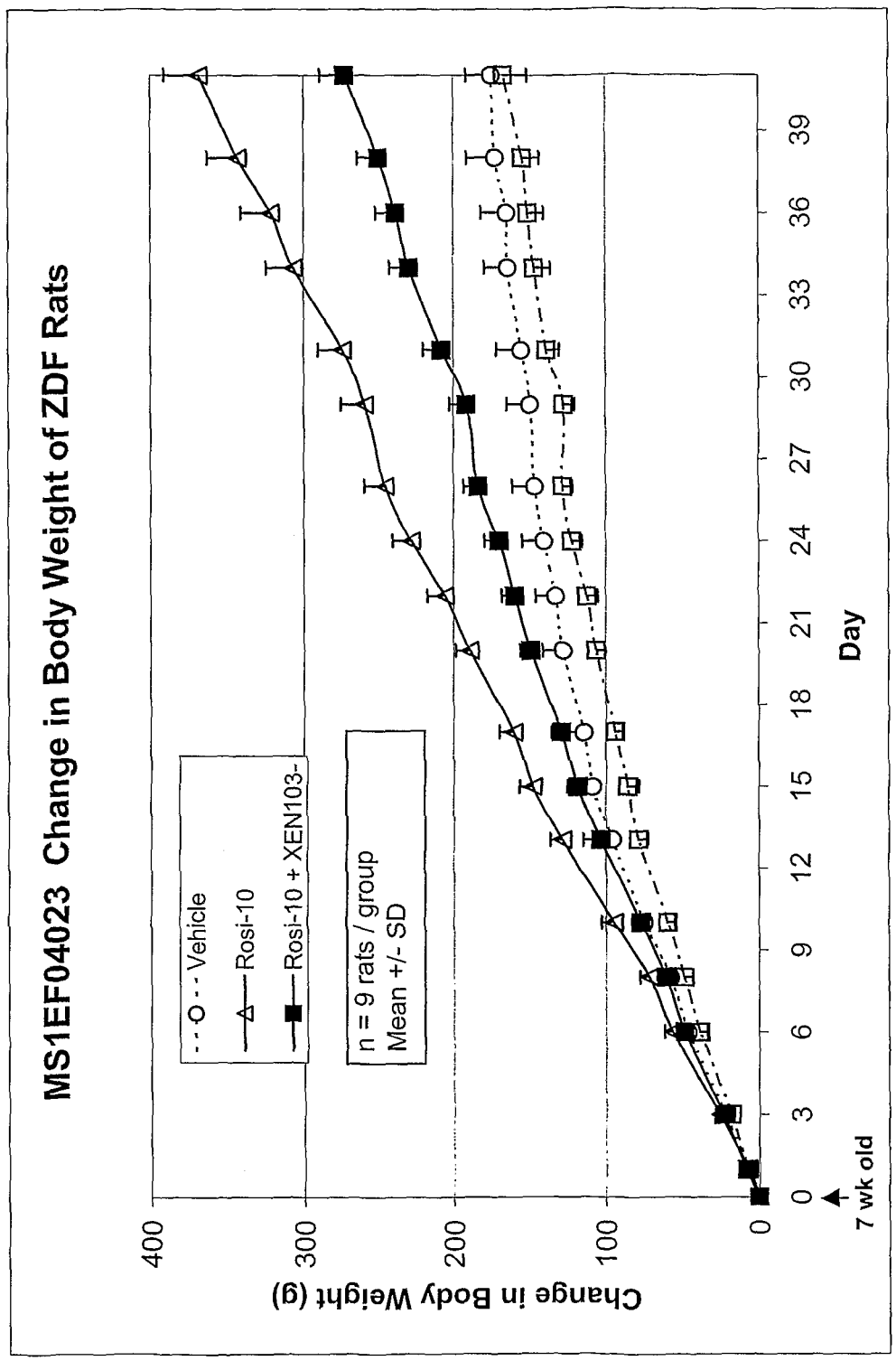
FIG. 1. measures the effect of oral administration of an SCD-1 inhibitor in Zucker Diabetic Fatty Rat (ZDF) ($6^{th}$ week of age) Model. It shows the change in body weight of ZDF Rats according to Example 1.

The present invention provides a method for treating adverse weight gain associated with drug therapy. In particular, the present invention is directed to a novel combination therapy of a therapeutically effective amount of an SCD-1 inhibitor with a drug therapy. The SCD-1 inhibitor is used to treat the side effect of adverse weight gain caused by the drug therapy. As demonstrated in the present specification, the SCD-1 inhibitor was shown to have the beneficial property of reducing the adverse weight gain while still maintaining the efficacy of the drug therapy. The improvement was statistically significant. The methods of this invention are particularly useful for drug therapy for treating diabetes, particularly type 2 diabetes.

DEFINITIONS

The term 'condition' or 'disease' may be used interchangeably and includes incipient disease, and disorder.

The term 'subject' means any mammal, including a human.

The term 'drug' or 'drug therapy' means a course of administration of any therapeutic agent, pharmacological substance or nutrient preparation (whether prescription, over the counter, off-the-shelf, ethical or not) for the treatment of subject having a disease.

The term "side effect" means an effect of drug treatment that may range in severity from barely noticeable, to uncomfortable, to dangerous. Preferably, the effect is "undesired" or "unwanted" such as for example, adverse weight gain.

The term 'therapeutic agent' as used herein covers the active ingredients critical to the proper action of drug and drug therapies. For example, Metformin Hydrochloride; Rosiglitazone Maleate is the active ingredient for the antidiabetic drug Avandia®.

The term 'treat', 'treating' or 'treatment' as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

The term "therapeutically effective amount" refers to that amount of a compound of the invention which, when administered to a mammal, preferably a human, is sufficient to effect treatment, as defined above, of a disease or condition in the mammal, preferably a human. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

Adverse Weight Gain Associated with Drug Therapy

Drug therapy is not without its complications. Many people who suffer from diseases undertake drug therapy only to find that during the course of treatment one or more side effects arise. Drug therapy management by patients and their care-givers is often a contest between the benefits of the treatment and the extent or seriousness of the side effects.

A side effect associated with certain drug treatments is adverse weight gain. Adverse weight gain can range from the relatively insignificant level of a few pounds associated with the antihistamine nasal spray like Azelastine Hydrochloride (e.g. Astelin®), for instance, to the serious complications resulting from treatments with therapeutics such as Olanzapine (e.g. Zyprexa®), where patients who are administered 15 mg/day can expect to gain between 22 and 45 kg over first the year of treatment. (see, Canadian Adverse Drug Reaction Newsletter, Vol. 11, 4, Oct. 2001).

Adverse weight gain may be considered a side effect either subjectively by the patient, subjectively by other people, or objectively according to measures which correlate increases in weight gain with diseases related to weight gain and obesity, such as cardiovascular disease, diabetes, and others of this class. An objective measure of adverse weight gain is any weight gain that results in obesity, which can be defined as a body weight more than 20% above the ideal body weight. Another objective measure of adverse weight gain can be determined, for example, in accordance with the U.S. National Institute of Health ('NIH') classification of overweight and obesity by body mass index ('BMI'), as set out in Table 2 below. (see http://www.nhlbi.nih.gov)

TABLE 2

NIH Classification of Overweight and Obesity by BMI.

| Class | BMI (kg/m$^2$) |
|---|---|
| Underweight | <18.5 |
| Normal | 18.5-24.9 |
| Overweight | 25.0-29.9 |
| Obesity I | 30.0-34.9 |
| Obesity II | 35.0-39.9 |
| Extreme Obesity III | ≧40 |

According to the NIH, overweight and obesity substantially raises the risk of morbidity from hypertension, dyslipidemia, type 2 diabetes, coronary heart disease, stroke, gallbladder disease, osteoarthritis, sleep apnea, and respiratory problems, and endometrial, breast, prostate, and colon cancers. Therefore, any weight gain that results in movement to a class with a BMI of 25 or greater would be considered objectively as adverse weight gain. An example of subjective measure of adverse weight gain is any weight gain that increases BMI as a result of a drug therapy in addition to or in extension of the desired therapeutic effect.

A 'drug therapy having a side effect of adverse weight gain' or "adverse weight gain associated with a drug therapy' is therefore one where treatment with the drug is associated with adverse weight gain that is perceived to be adverse either subjectively by the patient or other people, or objectively according to one or more of the medically accepted standards of measurement, as discussed above. Drug therapies that cause adverse weight gain in only a small percentage of the patient population is captured by this definition, as it is understood by one skilled in the art that drug therapies typically do not cause adverse weight gain in 100% of the patient population. Some examples of such drugs include but are not limited to those set out in Table 3.

TABLE 3

Drugs having the side effect of adverse weight gain.

| Drug | Side Effect | Commonly Prescribed Treatment |
|---|---|---|
| Anti-Depressants | | |
| Selective serotonin reuptake inhibitors - sertraline hydrochloride (e.g. Zoloft ®), as described in U.S. Pat. No. 4,536,518 | Adverse weight gain | 25 mg-100 mg/daily |
| Fluoxetine Hydrochloride (e.g. Prozac ®) as described in U.S. Pat. No. 6,365,633; and PCT Application Nos. WO 01/27060, and WO 01/162341. | | 10 mg-40 mg/daily |
| Monoamine oxidase inhibitors ('MAOIs') - Phenelzine Sulfate (e.g. Nardil ®); Tranylcypromine (e.g. Parnate ®) | Adverse weight gain | 30 mg/daily |
| Tricyclic inhibitors - amitriptyline hydrochloride (e.g. Libitrol ™) | 15 kg-20 kg | 10 mg/daily for 2 to 6 months |
| Lithium Carbonate (e.g. Eskalith ®, Eskalith CR ®, Lithobid ®) | 10 kg or more in 11%-65% of treated patients | 300 mg-450 mg/daily |
| Migraine Prevention | | |
| Calcium channel blockers (e.g. Flunarizine ®) | 4.3 kg in 21% of treated patients | 5 mg/daily for 4 months |
| Anti-epileptics/Anti-convulsants | | |
| Valproate Sodium (e.g. Depacon ®) | 5.8 ± 4.2 kg (71% of treated patient) | 250 mg/daily for 32 weeks |
| Carbamazepine (e.g. Tegretol ®, Carbatrol ®, Epitol ®) | Up to 15 kg, 15-20% of treated patients | 100 mg-400 mg/daily for 3 months |
| Gabapentin (e.g. Neurotonin ®) | Up to 15 kg, 15-20% of treated patients | 100 mg-300 mg/daily |
| Topiramate (e.g. Topamax ®) | Adverse weight gain | 25 mg-200 mg/daily |
| Anti-diabetics | | |
| Insulin or insulin mimectics | 9.5 lbs | 1 year @ multiple shots a day |

TABLE 3-continued

Drugs having the side effect of adverse weight gain.

| Drug | Side Effect | Commonly Prescribed Treatment |
|---|---|---|
| Thiazolidinediones (i.e. PPARγ agonist) - Metformin Hydrocholride; Rosiglitazone Maleate (e.g. Avandia ®) as described in U.S. Pat. No. 5,002,953; and PCT Application Nos. WO97/27857, 97/28115, 97/28137, and 97/27847 | 8.0 kg | 2-8 mg/daily for 3 months |
| Meglitinides - Repaglinide (e.g. Prandin ®), nateglinide. | 0.3-5.5 kg | 0.5-4.0 mg/daily for 4-5 months |
| Sulfonylureas - Glimepiride (e.g. Amaryl ®) | 5 kg | 1-4 mg/daily for 3 to 12 months |
| Anti-psychotics | | |
| Second Generation - Olanzapine (e.g. Zyprexa ®) | 4.45 kg | 5.0-20 mg/daily for 10 weeks |
| Risperidone (e.g. Risperdal ®) | 2.10 kg | 0.25 mg-4.0 mg/daily for 10 weeks |
| Aripiprazole (e.g. Abilify ™) | 1.0 kg | 5.0-30 mg/daily for 4-6 weeks |
| Cancer Therapy | | |
| Chemotherapy - Arsenic trioxide (e.g. Trisenox ™) as described in U.S. Pat. No. 6,723,351. | Adverse weight gain (13% of treated patients) | 0.15 mg/kg/day for 8 weeks |
| Hormone Replacement Therapy - Goserelin Acetate (e.g. Zoladex ®) | Adverse weight gain | 3.6 mg/28 days patch |
| Megestrol acetate (Megace ®) | | 20 mg-40 mg/daily |
| Oral Contraceptives | | |
| Progesterone (e.g. depot medroxyprogesterone acetate - DMPA) | 6.2% increase in body weight | 6 months |
| Endometriosis Therapy | | |
| Anti-estrogens - medroxyprogesterone acetate (e.g. Depo-Provera) | 16 lbs | 150 mg IM dose/3 months for 6 years |
| Osteoporosis Therapy | | |
| Raloxifene Hydrochloride (e.g. Evista ®) | Adverse weight gain | 60 mg/daily |
| Hair Growth Therapy | | |
| Minoxidal (e.g. Rogaine ®) | Adverse weight gain | Topical 1 mL twice daily |
| HIV Therapy | | |
| Protease Inhibitors - Lopinavir; Ritonavir (e.g. Kaletra ®) | Adverse weight gain | 133.3 mg Lopinavir/33.3 Ritonvair/daily |
| Therapy for Systemic Inflammatory Conditions | | |
| Budesonide (e.g. Pulmicort Turbuhaler) | Adverse weight gain | 20 mg/kg/daily |

The instant invention provides a solution for adverse weight gain associated with drug therapies, particularly those identified in Table 3 above, by providing a combination therapy of one or more drug therapies with an SCD-1 inhibitor compound to treat the adverse weight gain. For example, combinations of a therapeutically effective dose of an SCD-1 inhibitor and a drug therapy selected from table 3, where the effective dosage of the SCD-1 inhibitor is in the range of about 0.01 to about 500 mg/kg per day and the effective dosage of the drug therapy as disclosed in table 3 above. A preferred dosage range for the SCD-1 inhibitor is in the range of about 0.05 mg/kg to about 100 mg/kg, preferably in the range of about 0.20 mg/kg to about 50 mg/kg, preferably in the range of about 0.50 mg/kg to about 20 mg/kg, preferably in the range of about 1.0 mg/kg to about 2.0 mg/kg (i.e. for an average human of 70 kg, about 70 mg to about 140 mg per dose.). The SCD-1 inhibitor includes any compounds which inhibit the SCD-1 activity. A relevant test to determine whether or not a compound is an SCD-1 inhibitor is described below. In a preferred embodiment, the SCD-1 inhibitor includes, but not limited to, compounds of formula (I) as disclosed below. In a more preferred embodiment, the SCD-1 inhibitor is a compound selected from the list disclosed below.

These drug therapies are readily available commercially. Other drug therapies that have a side effect of adverse weight gain may also be used in the present invention and one skilled in the art can readily identify them. For example, reference can be made to the FDA website (http://www.fda.gov/default.htm) which lists the side effects of all commercially available drugs in the United States. The combination therapy of the invention can be co-administered to a subject, wherein a first therapeutically effective amount of a drug having the adverse side effect of weight gain, such as those in table 3, and a second amount of an SCD-1 inhibitor compound, examples of which are described below, which is sufficient to treat, ameliorate, reduce, counteract or eliminate the weight gain resulting from or anticipated from the first dose.

The administration of the SCD-1 inhibitor relative to the first medication can occur before, at the same time (e.g. contemporaneously), subsequent to or on an irregular basis. Those skilled in the art are able to identify a suitable temporal relationship between the agents which will achieve the desired treatment result, several examples of which are set out below. Treatment may continue until the disease process is resolved, until the symptoms of the disease are reduced to a satisfactory level or until otherwise determined by the physician and patient. In some cases, treatment may be chronic. As described herein, the present invention encompasses co-administration of an SCD-1 inhibitor and an anti-diabetic to a subject.

When administered non-contemporaneously (e.g. sequentially) the active agents will typically be formulated separately. When administered contemporaneously, it may be advantageous to provide the SCD-1 inhibitor in a dosage form in combination with the first medicament, as disclosed in the compositions listed below. A significant advantage of such a combination will be to improve patient compliance and the effect of the therapy.

SCD-1 Inhibitors

SCD-1 is a key regulatory enzyme in fatty acid metabolism and a novel target for the treatment of obesity and its resulting metabolic consequences, including the metabolic syndrome. SCD-1 introduces a double bond in the $C_9$-$C_{10}$ position of saturated fatty acids. The preferred substrates are palmitoyl-CoA (16:0) and stearoyl-CoA (18:0), which are converted to palmitoleoyl-CoA (16:1) and oleoyl-CoA (18:1), respectively. The resulting mono-unsaturated fatty acids are substrates for incorporation into phospholipids, triglycerides, and cholesteryl esters.

Sterculic acid (8-(2-octylcyclopropenyl)octanoic acid), m.w. 294.5, and malvalic acid (7-(2-octylcyclopropenyl)heptanoic acid), m.w. 280.4, are known to non-specifically inhibit SCD activity. These agents are believed to inhibit SCD enzymatic activity by interaction with the enzyme, thus inhibiting delta-9 desaturation. Other agents that may inhibit SCD activity include thia-fatty acids, such as 9-thiastearic acid (also called 8-nonylthiooctanoic acid) and other fatty acids with a sulfoxy moiety. These known modulators of delta-9 desaturase activity are not useful for treating the diseases and disorders linked to SCD1 biological activity. None of the known SCD inhibitor compounds are selective for SCD or delta-9 desaturases, as they also inhibit other desaturases and enzymes. The thia-fatty acids, conjugated linoleic acids and cyclopropene fatty acids (malvalic acid and sterculic acid) are neither useful at reasonable physiological doses, nor are they specific inhibitors of SCD1 biological activity, rather they demonstrate cross inhibition of other desaturases, in particular the delta-5 and delta-6 desaturases by the cyclopropene fatty acids.

The present invention recognizes that SCD-1 inhibitors are useful in combination with drug therapies having the side effect of adverse weight gain because of their significance in regulating lipid levels, especially plasma lipid levels, and which are useful in the treatment of SCD-mediated diseases such as diseases related to obesity, metabolic syndrome and the like.

According to the present invention, the SCD-1 inhibitor is a compound having the following formula (I):

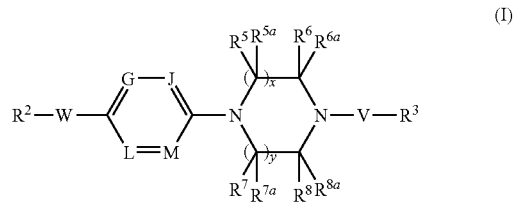

wherein:

x and y are each independently 1, 2 or 3;

W is a direct bond, —N($R^1$)C(O)—, —C(O)N($R^1$)—, —OC(O)N($R^1$)—, —N($R^1$)C(O)N($R^1$)—, —O—, —N($R^1$)—, —S(O)$_t$— (where t is 0, 1 or 2), —N($R^1$)S(O)$_p$— (where p is 1 or 2), —S(O)$_p$N($R^1$)— (where p is 1 or 2), —C(O)—, —OS(O)$_2$N($R^1$)—, —OC(O)—, —C(O)O—, —N($R^1$)C(O)O—, —N$R^1$C(=N$R^{1a}$)N$R^1$—, —N$R^1$C(=S)N$R^1$—, or —C(=N$R^{1a}$)N$R^1$—;

V is —C(O)—, —C(O)O—, —C(S)—, —C(O)N($R^1$)—, —S(O)$_t$— (where t is 0, 1 or 2), —S(O)$_p$N($R^1$)— (where p is 1 or 2), —C($R^{10}$)H—, —N($R^1$)—, —C(=N$R^{1a}$)—, or —O—;

G, J, L and M are each independently selected from —N= or —C($R^4$)=; provided that at most two of G, J, L and M are —N=;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

each $R^{1a}$ is independently selected from the group consisting of hydrogen, $C_1$-$C_{12}$alkyl, $C_4$-$C_{12}$cycloalkylalkyl, $C_7$-$C_{19}$aralkyl, O$R^1$, and cyano;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

each $R^4$ is independently selected from hydrogen, fluoro, chloro, methyl, methoxy, trifluoromethyl, cyano, nitro or —N($R^9$)$_2$;

each $R^5$, $R^{5a}$, $R^6$, $R^{6a}$, $R^7$, $R^{7a}$, $R^8$ and $R^{8a}$ is independently selected from hydrogen or $C_1$-$C_3$alkyl;

or $R^5$ and $R^{5a}$ together, or $R^6$ and $R^{6a}$ together, or $R^7$ and $R^{7a}$ together, or $R^8$ and $R^{8a}$ together are an oxo group, provided that when V is —C(O)—, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

or one of $R^5$, $R^{5a}$, $R^6$, and $R^{6a}$ together with one of $R^7$, $R^{7a}$, $R^8$ and $R^{8a}$ form an alkylene bridge, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

$R^{10}$ is hydrogen or $C_1$-$C_3$alkyl; and each $R^9$ is independently selected from hydrogen or $C_1$-$C_6$alkyl;

provided that when G, J and L are each —$C(R^4)$ where each $R^4$ is hydrogen, and M is —N=, and x is 1 or 2 and y is 1; W cannot be —$N(R^1)C(O)$—;

a stereoisomer, enantiomer or tautomer thereof, a pharmaceutically acceptable salt thereof.

DEFINITIONS

Certain chemical groups named herein are preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Methoxy" refers to the —$OCH_3$ radical.

"Cyano" refers to the —CN radical.

"Nitro" refers to the —$NO_2$ radical.

"Trifluoromethyl" refers to the —$CF_3$ radical.

"Oxo" refers to the =O substituent.

"Thioxo" refers to the =S substituent.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})(S(O)_tR^{16})$ (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and each $R^{16}$ is alkyl, haloalkyl, cycloalkyl, cycloalkylalkyl, aryl, aralkyl, heterocyclyl, heterocylylalkyl, heteroaryl or heteroarylalkyl, and where each of the above substituents is unsubstituted unless otherwise indicated.

"$C_1$-$C_3$alkyl" refers to an alkyl radical as defined above containing one to three carbon atoms. The $C_1$-$C_3$alkyl radical may be optionally substituted as defined for an alkyl group.

"$C_1$-$C_6$alkyl" refers to an alkyl radical as defined above containing one to six carbon atoms. The $C_1$-$C_6$alkyl radical may be optionally substituted as defined for an alkyl group.

"$C_1$-$C_{12}$alkyl" refers to an alkyl radical as defined above containing one to twelve carbon atoms. The $C_1$-$C_{12}$alkyl radical may be optionally substituted as defined for an alkyl group.

"$C_2$-$C_6$alkyl" refers to an alkyl radical as defined above containing two to six carbon atoms. The $C_2$-$C_6$alkyl radical may be optionally substituted as defined for an alkyl group.

"$C_3$-$C_6$alkyl" refers to an alkyl radical as defined above containing three to six carbon atoms. The $C_3$-$C_6$alkyl radical may be optionally substituted as defined for an alkyl group.

"$C_3$-$C_{12}$alkyl" refers to an alkyl radical as defined above containing three to twelve carbon atoms. The $C_3$-$C_{12}$alkyl radical may be optionally substituted as defined for an alkyl group.

"$C_6$-$C_{12}$alkyl" refers to an alkyl radical as defined above containing six to twelve carbon atoms. The $C_6$-$C_{12}$alkyl radical may be optionally substituted as defined for an alkyl group.

"$C_7$-$C_{12}$alkyl" refers to an alkyl radical as defined above containing seven to twelve carbon atoms. The $C_7$-$C_{12}$alkyl radical may be optionally substituted as defined for an alkyl group.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$OR^{14}$, —$C(O)$—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})(S(O)_tR^{16})$ (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocylylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$alkenyl" refers to an alkenyl radical as defined above containing three to 12 carbon atoms. The $C_3$-$C_{12}$alkenyl radical may be optionally substituted as defined for an alkenyl group.

"$C_2$-$C_{12}$alkenyl" refers to an alkenyl radical as defined above containing two to 12 carbon atoms. The $C_2$-$C_{12}$alkenyl radical may be optionally substituted as defined above for an alkenyl group.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkylene bridge" refers to a straight or branched divalent hydrocarbon bridge, linking two different carbons of the same ring structure, consisting solely of carbon and hydrogen, containing no unsaturation and having from one to twelve carbon atoms, preferably having from one to eight carbons, e.g., methylene, ethylene, propylene, n-butylene, and the like. The alkylene bridge may link any two carbons within the ring structure.

"Alkoxy" refers to a radical of the formula —$OR_a$ where $R_a$ is an alkyl radical as defined above. The alkyl part of the alkoxy radical may be optionally substituted as defined above for an alkyl radical.

"$C_1$-$C_6$alkoxy" refers to an alkoxy radical as defined above containing one to six carbon atoms. The alkyl part of the $C_1$-$C_6$alkoxy radical may be optionally substituted as defined above for an alkyl group.

"$C_1$-$C_{12}$alkoxy" refers to an alkoxy radical as defined above containing one to twelve carbon atoms. The alkyl part of the $C_1$-$C_{12}$alkoxy radical may be optionally substituted as defined above for an alkyl group.

"$C_3$-$C_{12}$alkoxy" refers to an alkoxy radical as defined above containing three to twelve carbon atoms. The alkyl part of the $C_3$-$C_{12}$alkoxy radical may be optionally substituted as defined above for an alkyl group.

"Alkoxyalkyl" refers to a radical of the formula —$R_a$—O—$R_a$ where each $R_a$ is independently an alkyl radical as defined above. The oxygen atom may be bonded to any carbon in either alkyl radical. Each alkyl part of the alkoxyalkyl radical may be optionally substituted as defined above for an alkyl group.

"$C_2$-$C_{12}$alkoxyalkyl" refers to an alkoxyalkyl radical as defined above containing two to twelve carbon atoms. Each alkyl part of the $C_2$-$C_{12}$alkoxyalkyl radical may be optionally substituted as defined above for an alkyl group.

"$C_3$alkoxyalkyl" refers to an alkoxyalkyl radical as defined above containing three carbon atoms. Each alkyl part of the $C_3$alkoxyalkyl radical may be optionally substituted as defined above for an alkyl group.

"$C_3$-$C_{12}$alkoxyalkyl" refers to an alkoxyalkyl radical as defined above containing three to twelve carbon atoms. Each alkyl part of the $C_3$-$C_{12}$alkoxyalkyl radical may be optionally substituted as defined above for an alkyl group.

"Alkylsulfonyl" refers to a radical of the formula —$S(O)_2R_a$ where $R_a$ is an alkyl group as defined above. The alkyl part of the alkylsulfonyl radical may be optionally substituted as defined above for an alkyl group.

"$C_1$-$C_6$alkylsulfonyl" refers to an alkylsulfonyl radical as defined above having one to six carbon atoms. The $C_1$-$C_6$alkylsulfonyl group may be optionally substituted as defined above for an alkylsulfonyl group.

"Aryl" refers to aromatic monocyclic or multicyclic hydrocarbon ring system consisting only of hydrogen and carbon and containing from 6 to 19 carbon atoms, preferably 6 to 10 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$ (where t is 1 to 2), —$R^{15}$—$S(O)_tOR^{16}$ (where t is 1 to 2), —$R^{15}$—$S(O)_tR^{16}$ (where t is 0 to 2), and —$R^{15}$—$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Aralkyl" refers to a radical of the formula —$R_aR_b$ where $R_a$ is an alkyl radical as defined above and $R_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"$C_7$-$C_{12}$aralkyl" refers to an aralkyl group as defined above containing seven to twelve carbon atoms. The aryl part of the $C_7$-$C_{12}$aralkyl radical may be optionally substituted as described above for an aryl group. The alkyl part of the $C_7$-$C_{12}$aralkyl radical may be optionally substituted as defined above for an alkyl group.

"$C_{13}$-$C_{19}$aralkyl" refers to an aralkyl group as defined above containing thirteen to nineteen carbon atoms. The aryl part of the $C_{13}$-$C_{19}$aralkyl radical may be optionally substituted as described above for an aryl group. The alkyl part of the $C_{13}$-$C_{19}$aralkyl radical may be optionally substituted as defined above for an alkyl group.

"Aralkenyl" refers to a radical of the formula —$R_cR_b$ where $R_c$ is an alkenyl radical as defined above and $R_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aryloxy" refers to a radical of the formula —$OR_b$ where $R_b$ is an aryl group as defined above. The aryl part of the aryloxy radical may be optionally substituted as defined above.

"Aryl-$C_1$-$C_6$alkyl" refers to a radical of the formula —$R_h$-$R_i$ where $R_h$ is an unbranched alkyl radical having one to six carbons and $R_i$ is an aryl group attached to the terminal carbon of the alkyl radical.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$ (where t is 1 to 2), —$R^{15}$—

S(O)$_t$OR$^{16}$ (where t is 1 to 2), —R$^{15}$—S(O)$_t$R$^{16}$ (where t is 0 to 2), and —R$^{15}$—S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"C$_3$-C$_6$cycloalkyl" refers to a cycloalkyl radical as defined above having three to six carbon atoms. The C$_3$-C$_6$cycloalkyl radical may be optionally substituted as defined above for a cycloalkyl group.

"C$_3$-C$_{12}$cycloalkyl" refers to a cycloalkyl radical as defined above having three to twelve carbon atoms. The C$_3$-C$_{12}$cycloalkyl radical may be optionally substituted as defined above for a cycloalkyl group.

"Cycloalkylalkyl" refers to a radical of the formula —R$_a$R$_d$ where R$_a$ is an alkyl radical as defined above and R$_d$ is a cycloalkyl radical as defined above. The cycloalkyl part of the cycloalkyl radical may be optionally substituted as defined above for an cycloalkyl radical. The alkyl part of the cycloalkyl radical may be optionally substituted as defined above for an alkyl radical.

"C$_4$-C$_{12}$cycloalkylalkyl" refers to a cycloalkylalkyl radical as defined above having four to twelve carbon atoms. The C$_4$-C$_{12}$cycloalkylalkyl radical may be optionally substituted as defined above for a cycloalkylalkyl group.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above, e.g., 2-bromoethenyl, 3-bromoprop-1-enyl, and the like. The alkenyl part of the haloalkenyl radical may be optionally substituted as defined above for an alkyl group.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$ OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)(S(O)$_t$R$^{16}$) (where t is 1 to 2), —R$^{15}$—S(O)$_t$OR$^{16}$ (where t is 1 to 2), —R$^{15}$—S(O)$_t$R$^{16}$ (where t is 0 to 2), and —R$^{15}$—S(O)$_t$N(R$^{14}$)$_2$ (where t is 1 to 2) where each R$^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"C$_3$-C$_{12}$heterocyclyl" refers to a heterocyclyl radical as defined above having three to twelve carbons. The C$_3$-C$_{12}$heterocyclyl may be optionally substituted as defined above for a heterocyclyl group.

"Heterocyclylalkyl" refers to a radical of the formula —R$_a$R$_e$ where R$_a$ is an alkyl radical as defined above and R$_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"C$_3$-C$_{12}$heterocyclylalkyl" refers to a heterocyclylalkyl radical as defined above having three to twelve carbons. The C$_3$-C$_{12}$heterocyclylalkyl radical may be optionally substituted as defined above for a heterocyclylalkyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)(S(O)$_t$R$^{16}$) (where t is 1 to 2), —R$^{15}$—S(O)$_t$OR$^{16}$ (where t is 1 to 2), —R$^{15}$—S(O)$_t$R$^{16}$ (where t is 0 to 2), and —R$^{15}$—S (O)$_t$N(R$^{14}$)$_2$ (where t is 1 to 2) where each R$^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"C$_1$-C$_{12}$heteroaryl" refers to a heteroaryl radical as defined above having one to twelve carbon atoms. The C$_1$-C$_{12}$heteroaryl group may be optionally substituted as defined above for a heteroaryl group.

"C$_5$-C$_{12}$heteroaryl" refers to a heteroaryl radical as defined above having five to twelve carbon atoms. The C$_5$-C$_{12}$heteroaryl group may be optionally substituted as defined above for a heteroaryl group.

"Heteroarylalkyl" refers to a radical of the formula —R$_a$R$_f$ where R$_a$ is an alkyl radical as defined above and R$_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"C$_3$-C$_{12}$heteroarylalkyl" refers to a heteroarylalkyl radical as defined above having three to twelve carbon atoms. The C$_3$-C$_{12}$heteroarylalkyl group may be optionally substituted as defined above for a heteroarylalkyl group.

"Heteroarylcycloalkyl" refers to a radical of the formula —R$_d$R$_f$ where R$_d$ is a cycloalkyl radical as defined above and R$_f$ is a heteroaryl radical as defined above. The cycloalkyl part of the heteroarylcycloalkyl radical may be optionally substituted as defined above for a cycloalkyl group. The heteroaryl part of the heteroarylcycloalkyl radical may be optionally substituted as defined above for a heteroaryl group.

"Heteroarylalkenyl" refers to a radical of the formula —R$_b$R$_f$ where R$_b$ is an alkenyl radical as defined above and R$_f$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Hydroxyalkyl" refers to a radical of the formula —R$_a$—OH where R$_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"C$_2$-C$_{12}$hydroxyalkyl" refers to an hydroxyalkyl radical as defined above containing two to twelve carbon atoms. The alkyl part of the C$_2$-C$_{12}$hydroxyalkyl radical may be optionally substituted as defined above for an alkyl group.

"C$_3$-C$_{12}$hydroxyalkyl" refers to an hydroxyalkyl radical as defined above containing three to twelve carbon atoms. The alkyl part of the C$_3$-C$_{12}$hydroxyalkyl radical may be optionally substituted as defined above for an alkyl group.

"C$_7$-C$_{12}$hydroxyalkyl" refers to an hydroxyalkyl radical as defined above containing seven to twelve carbon atoms. The alkyl part of the C$_7$-C$_{12}$hydroxyalkyl radical may be optionally substituted as defined above for an alkyl group.

"Hydroxyalkenyl" refers to a radical of the formula —R$_c$—OH where R$_c$ is an alkenyl radical as defined above. The hydroxy group may be attached to the alkenyl radical on any carbon within the alkenyl radical. The alkenyl part of the hydroxyalkenyl group may be optionally substituted as defined above for an alkenyl group.

"C$_2$-C$_{12}$hydroxyalkenyl" refers to an hydroxyalkenyl radical as defined above containing two to twelve carbon atoms. The alkenyl part of the C$_2$-C$_{12}$hydroxyalkenyl radical may be optionally substituted as defined above for an alkenyl group.

"C$_3$-C$_{12}$hydroxyalkenyl" refers to an hydroxyalkenyl radical as defined above containing three to twelve carbon atoms. The alkenyl part of the C$_3$-C$_{12}$hydroxyalkenyl radical may be optionally substituted as defined above for an alkenyl group.

"Hydroxyl-C$_1$-C$_6$-alkyl" refers to a radical of the formula —R$_h$—OH where R$_h$ is an unbranched alkyl radical having one to six carbons and the hydroxy radical is attached to the terminal carbon.

"Trihaloalkyl" refers to an alkyl radical, as defined above, that is substituted by three halo radicals, as defined above, e.g., trifluoromethyl. The alkyl part of the trihaloalkyl radical may be optionally substituted as defined above for an alkyl group.

"C$_1$-C$_6$trihaloalkyl" refers to a trihaloalkyl radical as defined above having one to six carbon atoms. The C$_1$-C$_6$trihaloalkyl may be optionally substituted as defined above for a trihaloalkyl group.

"Trihaloalkoxy" refers to a radical of the formula —OR$_g$ where R$_g$ is a trihaloalkyl group as defined above. The trihaloalkyl part of the trihaloalkoxy group may be optionally substituted as defined above for a trihaloalkyl group.

"C$_1$-C$_6$trihaloalkoxy" refers to a trihaloalkoxy radical as defined above having one to six carbon atoms. The C$_1$-C$_6$trihaloalkoxy group may be optionally substituted as defined above for a trihaloalkoxy group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to other through direct bonds or some or all of the rings may be fused to each other. Examples include, but are not limited to a cycloalkyl radical substituted by aryl group; a cycloalkyl group substituted by an aryl group, which, in turn, is substituted by another aryl group; and so forth. The chemical naming protocol and structure diagrams used herein employ and rely the chemical naming features as utilized by Chemdraw version 7.0.1 (available from Cambridgesoft Corp., Cambridge, Mass.). For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms which are assumed to be bonded to sufficient hydrogen atoms to complete the valency. Thus, for example, a compound of formula (I), as set forth above in the Summary of the Invention, wherein x and y are each 1; W is —N(R$^1$)C(O)—; V is —C(O)—; J and L are both —N═; G and M are both —C(R$^4$)═; R$^1$, R$^4$, R$^5$, R$^{5a}$, R$^6$, R$^{6a}$, R$^7$, R$^{7a}$, R$^8$ and R$^{8a}$ are each hydrogen; R$^2$ is 2-phenylethyl (phenethyl) and R$^3$ is 2-trifluoromethylphenyl, i.e., a compound of the following formula:

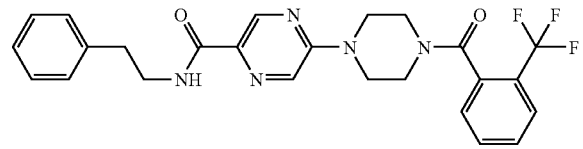

is named herein as 4-(2-Trifluoromethyl-benzoyl)-3,4,5,6-tetrahydro-2H-[1,2']bipyrazinyl-5'-carboxylic acid phenethyl-amide.

Certain radical groups of the compounds of the invention are depicted herein as linkages between two parts of the compounds of the invention. For example, in the following formula (I):

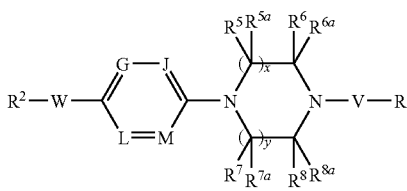

W is described, for example, as being —N($R^1$)C(O)—, —C(O)N($R^1$)—, or —N($R^1$)C(O)N($R^1$)—; and V is described as —C(O)—, —C(S)— or —C($R^{10}$)—. This description is meant to describe a W group attached to the $R^2$ group as follows: $R^2$—N($R^1$)C(O)—, $R^2$—C(O)N($R^1$)— or $R^2$—N($R^1$)C(O)N($R^1$)—; and meant to describe a V group attached to the $R^3$ group as follows: —C(O)—$R^3$, —C($R^{10}$)—$R^3$, or —C(S)—$R^3$. In other words, the description of the W and V linkage groups are meant to be read from left to right in view of formula (I) as depicted above.

EMBODIMENTS OF THE INVENTION

In one embodiment of the invention, the SCD-1 inhibitors are compounds of formula (I) as set forth above in the Summary of the Invention wherein:

G, J and L are each —C($R^4$) and M is —N=;
x and y are each 1;
W is —O—, —N($R^1$)—, —C($R^1$)$_2$—, —C(O)—, —OC(O)—, —S(O)$_t$—; (where t is 0, 1 or 2), —N($R^1$)S(O)$_t$— (where t is 1 or 2), —S(O)$_2$N($R^1$)—, —C(O)N($R^1$)—, —C(S)N($R^1$)—, —OS(O)$_2$N($R^1$)—, —OC(O)N($R^1$)—, —OC(S)N($R^1$)—, —N($R^1$)C(O)N($R^1$)— or —N($R^1$)C(S)N($R^1$)—;
V is —C(O)—, —C(S)—, —C(O)N($R^1$)—, —C(O)O—, —C(S)O—, —S(O)$_t$-(where t is 1 or 2), —S(O)$_t$N($R^1$)— (where t is 1 or 2) or —C($R^{10}$)H;
each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;
$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
each $R^4$ is independently selected from hydrogen, bromo, fluoro, chloro, methyl, methoxy, trifluoromethyl, cyano, nitro or —N($R^9$)$_2$;
$R^5$, $R^{5a}$, $R^6$, $R^{6a}$, $R^7$, $R^{7a}$, $R^8$, and $R^{8a}$ are each independently selected from hydrogen or $C_1$-$C_3$alkyl;
or $R^5$ and $R^{5a}$ together, or $R^6$ and $R^{6a}$ together, or $R^7$ and $R^{7a}$ together, or $R^8$ and $R^{8a}$ together are an oxo group, provided that when V is —C(O)—, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

$R^{10}$ is hydrogen or $C_1$-$C_3$alkyl; and
each $R^9$ is independently selected from hydrogen or $C_1$-$C_6$alkyl.

In another embodiment of the invention, the SCD-1 inhibitors are compounds of formula (I) as set forth above in the Summary of the Invention wherein:

G, J and L are each —C($R^4$) and M is —N=;
W is —C(O)N($R^1$)—;
V is —C(O)—;
x and y are each 1;
$R^1$ is selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_1$-$C_{12}$heteroaryl, $C_3$-$C_{12}$heterocyclylalkyl, $C_3$-$C_{12}$heterocyclyl, and $C_3$-$C_{12}$heteroarylalkyl, provided that $R^2$ is not pyrazinyl, pyridinonyl, pyrrolidinonyl or imidazolyl;
$R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$ heteroaryl and $C_3$-$C_{12}$heteroarylalkyl;
each $R^4$ is independently selected from hydrogen, bromo, fluoro, chloro, methyl, methoxy, trifluoromethyl, cyano, nitro or —N($R^9$)$_2$;
$R^5$, $R^{5a}$, $R^6$, $R^{6a}$, $R^7$, $R^{7a}$, $R^8$ and $R^{8a}$ are each independently selected from hydrogen or $C_1$-$C_3$alkyl;
or $R^7$ and $R^{7a}$ together, or $R^5$ and $R^{5a}$ together form an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl; and
each $R^9$ is independently selected from hydrogen or $C_1$-$C_6$alkyl.

Of this embodiment, a preferred embodiment of a compound of formula (I) is cyclohexanecarboxylic acid [6-(4-cyclohexanecarbonyl-piperazin-1-yl)pyridin-3-yl]amide.

In another embodiment of the invention, the SCD-1 inhibitors are compounds of formula (I) as set forth above in the Summary of the Invention wherein:

G, J and L are each —C($R^4$) and M is —N=;
W is —C(O)N($R^1$)—;
V is —C(O)—;
x and y are each 1;
$R^1$ is selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;
$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{11}$)$_2$, —OC(O)$R^{11}$, —C(O)O$R^{11}$, —S(O)$_2$N($R^{11}$)$_2$, cycloalkyl, heterocyclyl, heteroaryl and heteroarylcycloalkyl, provided that $R^3$ is not phenyl substituted with optionally substituted thienyl;

each $R^4$ is independently selected from hydrogen, bromo, fluoro, chloro, methyl, methoxy, trifluoromethyl, cyano, nitro or —N($R^9$)$_2$;

$R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

or $R^7$ and $R^{7a}$ together, or $R^5$ and $R^{5a}$ together form an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

each $R^{11}$ is independently selected from hydrogen, $C_1$-$C_6$alkyl, $C_3$-$C_6$cycloalkyl, aryl or aralkyl; and each $R^9$ is independently selected from hydrogen or $C_1$-$C_6$alkyl Of this embodiment, a preferred embodiment of a compound of formula (I) is selected from the group consisting of the following:

4-Methylpentanoic acid {6-[4-(2-trifluoromethylbenzoyl)piperazin-1-yl]pyridin-3-yl}amide;
Hexanoic acid {6-[4-(2-trifluoromethylbenzoyl)piperazin-1-yl]pyridin-3-yl}amide;
Heptanoic acid {6-[4-(2-trifluoromethylbenzoyl)piperazin-1-yl]pyridin-3-yl}amide;
Heptanoic acid {6-[4-(2,5-dichlorobenzoyl)piperazin-1-yl]pyridin-3-yl}amide;
Hexanoic acid {6-[4-(2,5-dichlorobenzoyl)piperazin-1-yl]pyridin-3-yl}amide;
Cyclohexanecarboxylic acid {6-[4-(2-trifluoromethylbenzoyl)piperazin-1-yl]pyridin-3-yl}amide;
3-Phenyl-N-{6-[4-(2-trifluoromethylbenzoyl)piperazin-1-yl]-pyridin-3-yl}propionamide;
4-Phenyl-N-{6-[4-(2-trifluoromethylbenzoyl)piperazin-1-yl]-pyridin-3-yl}butyramide; and
N-{6-[2-Oxo-4-(2-trifluoromethylbenzoyl)piperazin-1-yl]-pyridin-3-yl}-4-phenylbutyramide.

In another embodiment of the invention, the SCD-1 inhibitors are compounds of formula (I) as set forth above in the Summary of the Invention wherein:

G, J and L are each —C($R^4$) and M is —N=;
x and y are each 1;
W is —S(O)$_2$N($R^1$)—;
V is —C(O)—, —C(S)—, —C(O)N($R^1$)—, —C(O)O—, —S(O)$_t$-(where t is 1 or 2) or —S(O)$_t$N($R^1$)— (where t is 1 or 2);

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

each $R^4$ is independently selected from hydrogen, bromo, fluoro, chloro, methyl, methoxy, trifluoromethyl, cyano, nitro or —N($R^9$)$_2$;

$R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

or $R^5$ and $R^{5a}$ together, or $R^6$ and $R^{6a}$ together, or $R^7$ and $R^{7a}$ together, or $R^8$ and $R^{8a}$ together are an oxo group, provided that when $V_a$ is —C(O)—, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl; and each $R^9$ is independently selected from hydrogen or $C_1$-$C_6$alkyl.

Of this embodiment, a preferred embodiment of a compound of formula (I) is selected from the group consisting of the following:

Pentane-1-sulfonic acid {6-[4-(2-trifluoromethylbenzoyl)piperazin-1-yl]pyridin-3-yl}amide;
Butane-1-sulfonic acid {6-[4-(2-trifluoromethylbenzoyl)piperazin-1-yl]pyridin-3-yl}amide;
Hexane-1-sulfonic acid {6-[4-(2-trifluoromethylbenzoyl)piperazin-1-yl]pyridin-3-yl}amide;
Pentane-1-sulfonic acid {6-[4-(2-bromobenzoyl)piperazin-1-yl]pyridin-3-yl}amide;
Hexane-1-sulfonic acid {6-[4-(2,5-dichlorobenzoyl)-piperazin-1-yl]pyridin-3-yl}amide;
Pentane-1-sulfonic acid {6-[4-(2,5-dichlorobenzoyl)-piperazin-1-yl]pyridin-3-yl}amide;
Hexane-1-sulfonic acid {6-[4-(naphthalene-1-carbonyl)-piperazin-1-yl]pyridin-3-yl}amide;
Pentane-1-sulfonic acid {6-[4-(naphthalene-1-carbonyl)-piperazin-1-yl]pyridin-3-yl}amide; and
3-Phenylpropane-1-sulfonic acid {6-[4-(2-trifluoromethylbenzoyl)piperazin-1-yl]pyridin-3-yl}amide.

In another embodiment of the invention, the SCD-1 inhibitors are compounds of formula (I) as set forth above in the Summary of the Invention wherein:

G, J and L are each —C($R^4$) and M is —N=;
x and y are each 1;
W is —N($R^1$)C(O)N($R^1$)—;
V is —C(O)—, —C(S)—, —C(O)N($R^1$)—, —C(O)O—, —S(O)$_t$-(where t is 1 or 2) or —S(O)$_t$N($R^1$)— (where t is 1 or 2);

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

each $R^4$ is independently selected from hydrogen, bromo, fluoro, chloro, methyl, methoxy, trifluoromethyl, cyano, nitro or —N($R^9$)$_2$;

$R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

or $R^5$ and $R^{5a}$ together, or $R^6$ and $R^{6a}$ together, or $R^7$ and $R^{7a}$ together, or $R^8$ and $R^{8a}$ together are an oxo group, provided that when $V_a$ is —C(O)—, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl; and each $R^9$ is independently selected from hydrogen or $C_1$-$C_6$alkyl.

Of this embodiment, a preferred embodiment of a compound of formula (I) is selected from the group consisting of the following:

1-[6-(4-Cyclohexanecarbonylpiperazin-1-yl)pyridin-3-yl]-3-pentylurea;
1-[6-(4-Cyclopentanecarbonylpiperazin-1-yl)pyridin-3-yl]-3-pentylurea;
1-Pentyl-3-{6-[4-(2-trifluoromethylbenzoyl)piperazin-1-yl]-pyridin-3-yl}urea;
1-Butyl-3-{6-[4-(2-trifluoromethylbenzoyl)piperazin-1-yl]-pyridin-3-yl}urea;
1-Phenethyl-3-{6-[4-(2-trifluoromethylbenzoyl)piperazin-1-yl]pyridin-3-yl}urea;
1-Benzyl-3-{6-[4-(2-trifluoromethylbenzoyl)piperazin-1-yl]-pyridin-3-yl}urea;
1-(4-Fluorobenzyl)-3-{6-[4-(2-trifluoromethylbenzoyl)-piperazin-1-yl]pyridin-3-yl}urea;
1-Pentyl-3-{6-[4-(pyridine-2-carbonyl)piperazin-1-yl]-pyridin-3-yl}urea; and
1-Pentyl-3-{6-[4-(pyridine-4-carbonyl)piperazin-1-yl]-pyridin-3-yl}urea.

In another embodiment of the invention, the SCD-1 inhibitors are compounds of formula (I) as set forth above in the Summary of the Invention wherein:

G, J and L are each $—C(R^4)—$ and M is $—N=$;
x and y are each 1;
W is $—O—$, $—N(R^1)—$ or $—S(O)_t—$ (where t is 0, 1 or 2);
V is $—C(O)—$, $—C(S)—$, $—C(O)N(R^1)—$, $—C(O)O—$, $—S(O)_t$-(where t is 1 or 2) or $—S(O)_tN(R^1)—$ (where t is 1 or 2);
each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;
$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
each $R^4$ is independently selected from hydrogen, bromo, fluoro, chloro, methyl, methoxy, trifluoromethyl, cyano, nitro or $—N(R^9)_2$;
$R^5$, $R^{5a}$, $R^6$, $R^{6a}$, $R^7$, $R^{7a}$, $R^8$, and $R^{8a}$ are each independently selected from hydrogen or $C_1$-$C_3$alkyl;
or $R^5$ and $R^{5a}$ together, or $R^6$ and $R^{6a}$ together, or $R^7$ and $R^{7a}$ together, or $R^8$ and $R^{8a}$ together are an oxo group, provided that when $V_a$ is $—C(O)—$, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl; and
each $R^9$ is independently selected from hydrogen or $C_1$-$C_6$alkyl.

In another embodiment of the invention, the SCD-1 inhibitors are compounds of formula (I) as set forth above in the Summary of the Invention wherein:

G, J and L are each $—C(R^4)—$ and M is $—N=$;
x and y are each 1;
W is $—N(R^1)S(O)_t—$ (where t is 1 or 2);
V is $—C(O)—$, $—C(S)—$, $—C(O)N(R^1)—$, $—C(O)O—$, $—S(O)_t$-(where t is 1 or 2), $—S(O)_tN(R^1)—$ (where t is 1 or 2) or $—C(R^{10})H$;
each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;
$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
each $R^4$ is independently selected from hydrogen, bromo, fluoro, chloro, methyl, methoxy, trifluoromethyl, cyano, nitro or $—N(R^{13})_2$;
$R^5$, $R^{5a}$, $R^6$, $R^{6a}$, $R^7$, $R^{7a}$, $R^8$, and $R^{8a}$ are each independently selected from hydrogen or $C_1$-$C_3$alkyl;
or $R^5$ and $R^{5a}$ together, or $R^6$ and $R^{6a}$ together, or $R^7$ and $R^{7a}$ together, or $R^8$ and $R^{8a}$ together are an oxo group, provided that when V is $—C(O)—$, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;
$R^{10}$ is hydrogen or $C_1$-$C_3$alkyl; and
each $R^9$ is independently selected from hydrogen or $C_1$-$C_6$alkyl.

Of this embodiment, a preferred embodiment of a compound of formula (I) is selected from the group consisting of the following:

5-Bromo-6-[4-(5-fluoro-2-trifluoromethylbenzoyl)piperazin-1-yl]-pyridine-3-sulfonic acid (2-cyclopropylethyl)amide; and
6-[4-(5-fluoro-2-trifluoromethylbenzoyl)piperazin-1-yl]pyridine-3-sulfonic acid (2-cyclopropylethyl)amide.

In another embodiment of the invention, the SCD-1 inhibitors are compounds of formula (I) as set forth above in the Summary of the Invention wherein:

L and M are each $—N=$;
G and J are each $—C(R^4)—$;
x and y are each 1;
W is $—C(O)N(R^1)—$; $—C(O)N[C(O)R^{1a}]—$, $—N(R^1)C(O)N(R^1)—$ or $—N(R^1)C(O)—$;
V is $—C(O)—$, $—C(S)—$, or $—C(R^{10})H$;
each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxyl;
$R^{1a}$ is selected from the group consisting of hydrogen, $C_1$-$C_6$alkyl and cycloalkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

R³ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

each R⁴ is independently selected from hydrogen, fluoro, chloro, methyl, methoxy, trifluoromethyl, cyano, nitro or —N(R⁹)₂;

R⁵, R⁵ᵃ, R⁶, R⁶ᵃ, R⁷, R⁷ᵃ, R⁸, and R⁸ᵃ are each independently selected from hydrogen or $C_1$-$C_3$alkyl;

or R⁵ and R⁵ᵃ together, or R⁶ and R⁶ᵃ together, or R⁷ and R⁷ᵃ together, or R⁸ and R⁸ᵃ together are an oxo group, provided that when V is —C(O)—, R⁶ and R⁶ᵃ together or R⁸ and R⁸ᵃ together do not form an oxo group, while the remaining R⁵, R⁵ᵃ, R⁶, R⁶ᵃ, R⁷, R⁷ᵃ, R⁸, and R⁸ᵃ are each independently selected from hydrogen or $C_1$-$C_3$alkyl;

R¹⁰ is hydrogen or $C_1$-$C_3$alkyl; and each R⁹ is independently selected from hydrogen or $C_1$-$C_6$alkyl.

In another embodiment of the invention, the SCD-1 inhibitors are compounds of formula (I) as set forth above in the Summary of the Invention wherein:

L and M are each —N=;
G and J are each —C(R⁴)=;
x and y are each 1;
W is selected from —C(O)N(R¹)— and —N(R¹)C(O)—;
V is —C(O)—;

each R¹ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxy;

R² is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_3$-$C_{12}$heterocyclylalkyl, and $C_3$-$C_{12}$heteroarylalkyl;

R³ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_5$-$C_{12}$ heteroaryl and $C_3$-$C_{12}$heteroarylalkyl;

each R⁴ is independently selected from hydrogen, fluoro, chloro, methyl, methoxy and trifluoromethyl; and R⁵, R⁵ᵃ, R⁶, R⁶ᵃ, R⁷, R⁷ᵃ, R⁸, and R⁸ᵃ are each independently selected from hydrogen or $C_1$-$C_3$alkyl;

or R⁵ and R⁵ᵃ together or R⁷ and R⁷ᵃ together are an oxo group, while the remaining R⁵, R⁵ᵃ, R⁶, R⁶ᵃ, R⁷, R⁷ᵃ, R⁸, and R⁸ᵃ are each independently selected from hydrogen or $C_1$-$C_3$alkyl.

Of this embodiment, a preferred embodiment of a compound of formula (I) is selected from the group consisting of the following:

6-[4-(2-Ethylbutyryl)piperazin-1-yl]pyridazine-3-carboxylic acid (2-cyclopropylethyl)amide;
6-[4-(3,3,3-Trifluoro-2-methyl-2-trifluoromethylpropionyl)piperazin-1-yl]pyridazine-3-carboxylic acid (2-cyclopropylethyl)amide;
6-[4-(2,2-Dimethylpropionyl)piperazin-1-yl]pyridazine-3-carboxylic acid (2-cyclopropylethyl)amide;
6-[4-(2,2-Dimethylbutyryl)piperazin-1-yl]pyridazine-3-carboxylic acid (2-cyclopropylethyl)amide;
6-[4-(2,2-Dimethylpentanoyl)piperazin-1-yl]pyridazine-3-carboxylic acid (2-cyclopropylethyl)amide;
6-[4-(4,4,4-Trifluorobut-2-enoyl)piperazin-1-yl]pyridazine-3-carboxylic acid (2-cyclopropylethyl)amide;
6-[4-(4,4,4-Trifluoro-3-trifluoromethylbut-2-enoyl)-piperazin-1-yl]pyridazine-3-carboxylic acid (2-cyclopropylethyl)amide;
6-[4-(1-Hydroxycyclopropanecarbonyl)piperazin-1-yl]pyridazine-3-carboxylic acid (2-cyclopropylethyl)amide;
6-(4-Cyclobutanecarbonylpiperazin-1-yl)pyridazine-3-carboxylic acid (2-cyclopropylethyl)amide;
6-[4-(2-Trifluoromethylcyclopropanecarbonyl)piperazin-1-yl]pyridazine-3-carboxylic acid (2-cyclopropylethyl)amide;
6-(4-Cyclohexanecarbonylpiperazin-1-yl)pyridazine-3-carboxylic acid (2-cyclopropylethyl)amide;
6-[4-(2-Methylcyclohexanecarbonyl)piperazin-1-yl]pyridazine-3-carboxylic acid (2-cyclopropylethyl)amide;
6-[4-(3-Methylcyclohexanecarbonyl)piperazin-1-yl]pyridazine-3-carboxylic acid (2-cyclopropylethyl)amide;
6-[4-(4-Methylcyclohexanecarbonyl)piperazin-1-yl]pyridazine-3-carboxylic acid (2-cyclopropylethyl)amide;
6-[4-(2-Methylcyclopropanecarbonyl)piperazin-1-yl]pyridazine-3-carboxylic acid (2-cyclopropylethyl)amide;
6-[4-(2,2,3,3-Tetramethylcyclopropanecarbonyl)piperazin-1-yl]pyridazine-3-carboxylic acid (2-cyclopropylethyl)amide;
6-[4-(4,4,4-Trifluoro-3-hydroxy-3-trifluoromethylbutyryl)piperazin-1-yl]pyridazine-3-carboxylic acid (2-cyclopropylethyl)amide;
6-[4-(4,4,4-Trifluoro-3-hydroxy-3-methylbutyryl)piperazin-1-yl]pyridazine-3-carboxylic acid (2-cyclopropylethyl)amide;
6-[4-(3,3,3-Trifluoro-2-hydroxy-2-methylpropionyl)piperazin-1-yl]pyridazine-3-carboxylic acid (2-cyclopropylethyl)amide;
4-[6-(3-Methylbutylcarbamoyl)pyridazin-3-yl]piperazine-1-carboxylic acid t-butyl ester;
4-[6-(2-Cyclopropylethylcarbamoyl)pyridazin-3-yl]piperazine-1-carboxylic acid t-butyl ester;
6-{4-[2-(2-Trifluoromethylphenyl)acetyl]piperazin-1-yl}pyridazine-3-carboxylic acid (2-cyclopropylethyl)amide;
6-[4-(Pyridine-2-carbonyl)piperazin-1-yl]pyridazine-3-carboxylic acid (2-cyclopropylethyl)amide;
6-[4-(2-Ttrifluoromethylfuran-3-carbonyl)piperazin-1-yl]pyridazine-3-carboxylic acid (2-cyclopropylethyl)amide;
6-[4-(2-Chloro-4-trifluoromethylpyrimidine-5-carbonyl)piperazin-1-yl]pyridazine-3-carboxylic acid (2-cyclopropylethyl)amide;
6-[4-(5-Methyl-2-trifluoromethylfuran-3-carbonyl)piperazin-1-yl]pyridazine-3-carboxylic acid (2-cyclopropylethyl)amide;
6-[4-(2-Chloropyridine-3-carbonyl)piperazin-1-yl]pyridazine-3-carboxylic acid (2-cyclopropylethyl)amide;
6-[4-(2-Methyl-5-trifluoromethyloxazole-4-carbonyl)piperazin-1-yl]-pyridazine-3-carboxylic acid (2-cyclopropylethyl)amide;
6-[4-(2,6-Dichloropyridine-3-carbonyl)piperazin-1-yl]pyridazine-3-carboxylic acid (2-cyclopropylethyl)amide;
6-[4-(Pyrrolidine-1-carbonyl)piperazin-1-yl]pyridazine-3-carboxylic acid (2-cyclopropylethyl)amide;
6-[4-(1-Methyl-1H-pyrrole-2-carbonyl)piperazin-1-yl]pyridazine-3-carboxylic acid (2-cyclopropylethyl)amide; and
6-[4-(Tetrahydrofuran-2-carbonyl)piperazin-1-yl]pyridazine-3-carboxylic acid (2-cyclopropylethyl)amide.

In another embodiment of the invention, the SCD-1 inhibitors are compounds of formula (I) as set forth above in the Summary of the Invention wherein:

L and M are each —N═;
G and J are each —C(R⁴)═;
x and y are each 1;
V is —C(O)— or —C(S)—;
W is selected from —C(O)N(R¹)— and —N(R¹)C(O)—;
each R¹ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxy;
R² is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
R³ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N(R¹¹)₂, —OC(O)R¹¹, —C(O)OR¹¹, —S(O)₂N(R¹¹)₂, cycloalkyl, heterocyclyl, heteroaryl and heteroarylcycloalkyl, provided that R³ is not phenyl substituted with optionally substituted thienyl;
each R⁴ is independently selected from hydrogen, fluoro, chloro, methyl, methoxy and trifluoromethyl;
R⁵, R⁵ᵃ, R⁶, R⁶ᵃ, R⁷, R⁷ᵃ, R⁸, and R⁸ᵃ are each independently selected from hydrogen or $C_1$-$C_3$alkyl;
or R⁵ and R⁵ᵃ together, or R⁶ and R⁶ᵃ together, or R⁷ and R⁷ᵃ together, or R⁸ and R⁸ᵃ together are an oxo group, provided that when V is —C(O)—, R⁸ and R⁸ᵃ together or R⁷ and R⁷ᵃ together do not form an oxo group, while the remaining R⁵, R⁵ᵃ, R⁶, R⁶ᵃ, R⁷, R⁷ᵃ, R⁸, and R⁸ᵃ are each independently selected from hydrogen or $C_1$-$C_3$alkyl; and
each R¹¹ is independently selected from hydrogen, $C_1$-$C_6$alkyl, $C_3$-$C_6$cycloalkyl, aryl or aralkyl.

Of this embodiment, a preferred embodiment of a compound of formula (I) is selected from the group consisting of the following:

6-(4-Benzoylpiperazin-1-yl)pyridazine-3-carboxylic acid (2-cyclopropylethyl)amide;
6-[4-(2-Chloro-5-fluorobenzoyl)piperazin-1-yl]pyridazine-3-carboxylic acid (2-cyclopropylethyl)amide;
6-[4-(5-Chloro-2-trifluoromethylbenzoyl)piperazin-1-yl]pyridazine-3-carboxylic acid (2-cyclopropylethyl)amide;
6-[4-(2,6-Difluorobenzoyl)piperazin-1-yl]pyridazine-3-carboxylic acid (2-cyclopropylethyl)amide;
6-[4-(2,5-Bis-trifluoromethylbenzoyl)piperazin-1-yl]pyridazine-3-carboxylic acid (2-cyclopropylethyl)amide
6-[4-(2,4-Bis-trifluoromethylbenzoyl)piperazin-1-yl]pyridazine-3-carboxylic acid (2-cyclopropylethyl)amide;
6-[4-(2,5-Difluorobenzoyl)piperazin-1-yl]pyridazine-3-carboxylic acid (2-cyclopropylethyl)amide;
6-[4-(5-Fluoro-2-trifluoromethylbenzoyl)piperazin-1-yl]pyridazine-3-carboxylic acid (3-cyclopropylpropyl)amide;
6-[4-(2-Fluorobenzoyl)piperazin-1-yl]pyridazine-3-carboxylic acid (2-cyclopropylethyl)amide;
6-[4-(3-Fluoro-2-trifluoromethylbenzoyl)piperazin-1-yl]pyridazine-3-carboxylic acid (2-cyclopropylethyl)amide;
6-[4-(4-Fluoro-2-trifluoromethylbenzoyl)piperazin-1-yl]pyridazine-3-carboxylic acid (3-cyclopropylpropyl)amide;
6-[4-(2-Trifluoromethylbenzoyl)piperazin-1-yl]pyridazine-3-carboxylic acid (2-methylcyclopropylmethyl)amide;
6-[4-(5-Fluoro-2-methoxybenzoyl)piperazin-1-yl]pyridazine-3-carboxylic acid (2-cyclopropylethyl)amide;
6-[4-(2-Dimethylaminobenzoyl)piperazin-1-yl]pyridazine-3-carboxylic acid (2-cyclopropylethyl)amide;
6-[4-(2-Chloro-5-dimethylaminobenzoyl)piperazin-1-yl]pyridazine-3-carboxylic acid (2-cyclopropylethyl)amide;
6-[4-(2,5-Dimethylbenzoyl)piperazin-1-yl]pyridazine-3-carboxylic acid (2-cyclopropylethyl)amide;
6-[4-(2,5-Dichlorobenzoyl)piperazin-1-yl]pyridazine-3-carboxylic acid (2-cyclopropylethyl)amide;
6-[4-(2-Trifluoromethylbenzoyl)piperazin-1-yl]pyridazine-3-carboxylic acid cyclobutylmethylamide;
Acetic acid 2-{4-[6-(2-cyclopropylethylcarbamoyl)-pyridazin-3-yl]piperazine-1-carbonyl}phenyl ester;
6-[4-(2-Trifluoromethylbenzoyl)piperazin-1-yl]pyridazine-3-carboxylic acid (2-cyclopropyl-2-hydroxyethyl)amide;
6-[4-(2-Trifluoromethylbenzoyl)piperazin-1-yl]pyridazine-3-carboxylic acid (2-phenylcyclopropylmethyl)amide;
6-[4-(2-Trifluoromethylbenzoyl)piperazin-1-yl]pyridazine-3-carboxylic acid (3-cyclopropylpropyl)amide;
6-[4-(2-Cyanobenzoyl)piperazin-1-yl]pyridazine-3-carboxylic acid (2-cyclopropylethyl)amide;
6-{4-[2-(2-Trifluoromethylphenyl)acetyl]piperazin-1-yl}pyridazine-3-carboxylic acid (2-cyclopropylethyl)amide;
6-[4-(4-Fluoro-2-trifluoromethylbenzoyl)piperazin-1-yl]pyridazine-3-carboxylic acid (2-cyclopropylethyl)amide;
6-[4-(5-Chloro-2-trifluoromethylbenzoyl)piperazin-1-yl]pyridazine-3-carboxylic acid (3-cyclopropylpropyl)amide;
6-[3,5-Dimethyl-4-(2-trifluoromethylbenzoyl)piperazin-1-yl]pyridazine-3-carboxylic acid (2-cyclopropylethyl)amide;
2-{4-[6-(2-Cyclopropylethylcarbamoyl)pyridazin-3-yl]piperazine-1-carbonyl}benzoic acid methyl ester;
6-[4-(2-Trifluoromethyl-benzoyl)-piperazin-1-yl]-pyridazine-3-carboxylic acid (2-cyclobutyl-ethyl)-amide;
2-{4-[6-(2-Cyclopropyl-ethylcarbamoyl)-pyridazin-3-yl]-piperazine-1-carbonyl}-benzoic acid;
6-[4-(5-Chloro-2-trifluoromethyl-benzoyl)-piperazin-1-yl]-pyridazine-3-carboxylic acid (2-cyclobutyl-ethyl)-amide;
6-[4-(5-Fluoro-2-trifluoromethyl-benzoyl)-piperazin-1-yl]-pyridazine-3-carboxylic acid (2-cyclobutyl-ethyl)-amide;
6-[4-(2-Trifluoromethyl-benzoyl)-piperazin-1-yl]-pyridazine-3-carboxylic acid (3-cyclobutyl-propyl)-amide;
6-[4-(5-Fluoro-2-trifluoromethyl-benzoyl)-[1,4]diazepan-1-yl]-pyridazine-3-carboxylic acid (2-cyclopropyl-ethyl)-amide;
6-[4-(2-Trifluoromethyl-thiobenzoyl)-piperazin-1-yl]-pyridazine-3-carboxylic acid (2-cyclopropyl-ethyl)-amide;
6-[4-(2-Trifluoromethyl-benzoyl)-piperazin-1-yl]-pyridazine-3-carboxylic acid (4-cyclopropyl-butyl)-amide;
6-[4-(2-Trifluoromethyl-benzoyl)-piperazin-1-yl]-pyridazine-3-carboxylic acid (2,2-dimethyl-cyclopropylmethyl)-amide;
6-[4-(2-Nitrobenzoyl)piperazin-1-yl]pyridazine-3-carboxylic acid (3-methylbutyl)amide;
6-[4-(2-Chlorobenzoyl)piperazin-1-yl]pyridazine-3-carboxylic acid (3-methylbutyl)amide;
6-[4-(2,4-Dichlorobenzoyl)piperazin-1-yl]pyridazine-3-carboxylic acid (3-methylbutyl)amide;
6-[4-(2-Aminobenzoyl)piperazin-1-yl]pyridazine-3-carboxylic acid (3-methylbutyl)amide;
6-[4-(2-Trifluoromethylbenzoyl)piperazin-1-yl]pyridazine-3-carboxylic acid [2-(4-chlorophenoxy)ethyl]amide;
6-[4-(2-Trifluoromethylbenzoyl)piperazin-1-yl]pyridazine-3-carboxylic acid [2-(4-fluorophenoxy)ethyl]amide;

6-[4-(2-Trifluoromethylbenzoyl)piperazin-1-yl]pyridazine-3-carboxylic acid (3,3-dimethylbutyl)amide;
6-[4-(2-Trifluoromethylbenzoyl)piperazin-1-yl]pyridazine-3-carboxylic acid pentylamide;
4-({6-[4-(2-Trifluoromethylbenzoyl)piperazin-1-yl]pyridazine-3-carbonyl}amino)butyric acid ethyl ester;
6-[4-(5-Fluoro-2-trifluoromethylbenzoyl)piperazin-1-yl]pyridazine-3-carboxylic acid pentylamide;
6-[4-(2-Trifluoromethylbenzoyl)piperazin-1-yl]pyridazine-3-carboxylic acid (4-methylpentyl)amide;
6-[4-(2-Fluoro-6-trifluoromethylbenzoyl)piperazin-1-yl]pyridazine-3-carboxylic acid (3-methylbutyl)amide;
6-[4-(2,6-Difluorobenzoyl)piperazin-1-yl]pyridazine-3-carboxylic acid (3-methylbutyl)amide;
6-[4-(2-Trifluoromethylbenzoyl)piperazin-1-yl]pyridazine-3-carboxylic acid (2-oxo-2-phenylethyl)amide;
Acetic acid 1,1-dimethyl-3-({6-[4-(2-trifluoromethyl-benzoyl)piperazin-1-yl]pyridazine-3-carbonyl}amino)propyl ester;
6-[4-(2-Trifluoromethylbenzoyl)piperazin-1-yl]pyridazine-3-carboxylic acid (2-phenoxyethyl)amide;
6-[4-(2-Trifluoromethylbenzoyl)piperazin-1-yl]pyridazine-3-carboxylic acid hexylamide;
6-[4-(2-Trifluoromethylbenzoyl)piperazin-1-yl]pyridazine-3-carboxylic acid (4-methylpentyl)amide;
6-[4-(5-Fluoro-2-trifluoromethylbenzoyl)piperazin-1-yl]pyridazine-3-carboxylic acid (4-methylpentyl)amide;
6-[2,5-Dimethyl-4-(2-trifluoromethylbenzoyl)piperazin-1-yl]pyridazine-3-carboxylic acid pentylamide;
6-[4-(2-Trifluoromethyl-benzoyl)-piperazin-1-yl]-pyridazine-3-carboxylic acid heptylamide;
6-[4-(2-Sulfamoyl-benzoyl)-piperazin-1-yl]-pyridazine-3-carboxylic acid (3-methyl-butyl)-amide;
6-[4-(5-Chloro-2-trifluoromethyl-benzoyl)-piperazin-1-yl]-pyridazine-3-carboxylic acid hexylamide;
6-[4-(2-Trifluoromethyl-benzoyl)-piperazin-1-yl]-pyridazine-3-carboxylic acid (2-cyclopropyl-2-oxo-ethyl)-amide;
4-Trifluoromethyl-6-[4-(2-trifluoromethyl-benzoyl)-piperazin-1-yl]-pyridazine-3-carboxylic acid (3-methyl-butyl)-amide;
6-[4-(5-Fluoro-2-trifluoromethylbenzoyl)piperazin-1-yl]pyridazine-3-carboxylic acid pentyl-4-enylamide;
6-[4-(2-Trifluoromethylbenzoyl)piperazin-1-yl]pyridazine-3-carboxylic acid (4-hydroxybutyl)amide;
6-[4-(2-Trifluoromethylbenzoyl)piperazin-1-yl]pyridazine-3-carboxylic acid (3-hydroxy-4,4-dimethylpentyl)amide;
6-[4-(2-Trifluoromethylbenzoyl)piperazin-1-yl]pyridazine-3-carboxylic acid (3-hydroxy-3-methylbutyl)amide;
6-[4-(2-Trifluoromethylbenzoyl)piperazin-1-yl]pyridazine-3-carboxylic acid (2-hydroxy-3,3-dimethylbutyl)amide;
6-[4-(5-Fluoro-2-trifluoromethylbenzoyl)piperazin-1-yl]pyridazine-3-carboxylic acid (2-hydroxy-3,3-dimethylbutyl)amide;
6-[4-(2-Trifluoromethylbenzoyl)piperazin-1-yl]pyridazine-3-carboxylic acid [2-(2,4-fluorophenyl)ethyl]amide;
6-[4-(2-Trifluoromethylbenzoyl)piperazin-1-yl]pyridazine-3-carboxylic acid [2-(2-fluorophenyl)ethyl]amide;
6-[4-(2-Trifluoromethylbenzoyl)piperazin-1-yl]pyridazine-3-carboxylic acid [2-(4-chlorophenyl)ethyl]amide;
6-[4-(2-Trifluoromethylbenzoyl)piperazin-1-yl]pyridazine-3-carboxylic acid [2-(3-chlorophenyl)ethyl]amide;
6-[4-(2-Trifluoromethylbenzoyl)piperazin-1-yl]pyridazine-3-carboxylic acid (2-phenylpropyl)amide;
6-[4-(2-Trifluoromethylbenzoyl)piperazin-1-yl]pyridazine-3-carboxylic acid (2-biphenyl-4-ylethyl)amide;
(R)-6-[4-(2-Trifluoromethylbenzoyl)piperazin-1-yl]pyridazine-3-carboxylic acid (2-hydroxy-2-phenylethyl)amide;
(S)-6-[4-(2-Trifluoromethylbenzoyl)piperazin-1-yl]pyridazine-3-carboxylic acid (2-hydroxy-2-phenylethyl)amide;
Acetic acid 1-phenyl-2-({6-[4-(2-trifluoromethyl-benzoyl)-piperazin-1-yl]pyridazine-3-carbonyl}amino)ethyl ester;
6-[4-(2-Trifluoromethylbenzoyl)piperazin-1-yl]pyridazine-3-carboxylic acid [3-(4-fluorophenyl)propyl]amide;
6-[4-(2-Trifluoromethylbenzoyl)piperazin-1-yl]pyridazine-3-carboxylic acid (2,2-difluoro-2-phenylethyl)amide;
6-[4-(2-Trifluoromethylbenzoyl)piperazin-1-yl]pyridazine-3-carboxylic acid [2-(3-fluorophenyl)-2-hydroxyethyl]amide;
6-[4-(2-Trifluoromethylbenzoyl)piperazin-1-yl]pyridazine-3-carboxylic acid (2-ethoxyethyl)amide;
6-[4-(2-Trifluoromethylbenzoyl)piperazin-1-yl]pyridazine-3-carboxylic acid (2-methoxy-3,3-dimethylbutyl)amide;
2-(2-Cyclopropyl-ethoxy)-N-{6-[4-(2-trifluoromethyl-benzoyl)-piperazin-1-yl]-pyridazin-3-yl}-acetamide;
6-[4-(2-Trifluoromethylbenzoyl)piperazin-1-yl]pyridazine-3-carboxylic acid (4-chloro-phenyl)amide;
6-[4-(2-Trifluoromethylbenzoyl)piperazin-1-yl]pyridazine-3-carboxylic acid (4-carbamoyl-phenyl)amide;
6-[4-(2-Trifluoromethylbenzoyl)piperazin-1-yl]pyridazine-3-carboxylic acid (3-carbamoyl-phenyl)amide;
6-[4-(2-Trifluoromethylbenzoyl)piperazin-1-yl]pyridazine-3-carboxylic acid m-tolylamide;
6-[4-(2-Trifluoromethylbenzoyl)piperazin-1-yl]pyridazine-3-carboxylic acid p-tolylamide;
6-[4-(2-Trifluoromethylbenzoyl)piperazin-1-yl]pyridazine-3-carboxylic acid o-tolylamide;
6-[4-(2-Trifluoromethylbenzoyl)piperazin-1-yl]pyridazine-3-carboxylic acid (2-propylphenyl)amide;
6-[4-(2-Trifluoromethylbenzoyl)piperazin-1-yl]-pyridazine-3-carboxylic acid (4-propylphenyl)amide;
6-[4-(2-Trifluoromethyl-benzoyl)piperazin-1-yl]pyridazine-3-carboxylic acid (4-isopropylphenyl)amide;
6-[4-(2-Trifluoromethyl-benzoyl)piperazin-1-yl]pyridazine-3-carboxylic acid (2-isopropylphenyl)amide;
6-[4-(2-Trifluoromethylbenzoyl)piperazin-1-yl]pyridazine-3-carboxylic acid (2-chloro-phenyl)amide;
6-[4-(2-Trifluoromethylbenzoyl)piperazin-1-yl]pyridazine-3-carboxylic acid (2-cyano-3-fluorophenyl)amide;
6-[4-(2-Trifluoromethylbenzoyl)piperazin-1-yl]pyridazine-3-carboxylic acid (2,4-dimethyl-phenyl)amide;
6-[4-(2-Trifluoromethylbenzoyl)piperazin-1-yl]pyridazine-3-carboxylic acid (2,5-dimethyl-phenyl)amide;
6-[4-(2-Trifluoromethylbenzoyl)piperazin-1-yl]pyridazine-3-carboxylic acid (2,6-dimethyl-phenyl)amide;
6-[4-(2-Trifluoromethylbenzoyl)piperazin-1-yl]pyridazine-3-carboxylic acid (2,3-dimethyl-phenyl)amide;
6-[4-(2-Trifluoromethylbenzoyl)piperazin-1-yl]pyridazine-3-carboxylic acid (3,5-dimethyl-phenyl)amide;
6-[4-(2-Trifluoromethyl-benzoyl)piperazin-1-yl]pyridazine-3-carboxylic acid (3,4-dimethyl-phenyl)amide;
6-[4-(2-Trifluoromethyl-benzoyl)piperazin-1-yl]pyridazine-3-carboxylic acid (4-ethyl-phenyl)amide;
6-[4-(2-Trifluoromethyl-benzoyl)piperazin-1-yl]pyridazine-3-carboxylic acid (2-ethyl-phenyl)amide;
6-[4-(2-Trifluoromethylbenzoyl)piperazin-1-yl]pyridazine-3-carboxylic acid (3-fluoro-2-methylphenyl)amide;
6-[4-(2-Trifluoromethylbenzoyl)piperazin-1-yl]pyridazine-3-carboxylic acid (2-fluoro-4-methylphenyl)amide;
6-[4-(2-Trifluoromethylbenzoyl)piperazin-1-yl]pyridazine-3-carboxylic acid (4-fluoro-2-methylphenyl)amide;

6-[4-(2-Trifluoromethylbenzoyl)piperazin-1-yl]pyridazine-3-carboxylic acid (2-fluoro-5-methylphenyl)amide;
6-[4-(2-Trifluoromethylbenzoyl)piperazin-1-yl]-pyridazine-3-carboxylic acid (3-fluoro-5-methylphenyl)amide;
6-[4-(2-Trifluoromethylbenzoyl)piperazin-1-yl]-pyridazine-3-carboxylic acid (3-fluoro-phenyl)-amide;
6-[4-(2-Trifluoromethylbenzoyl)piperazin-1-yl]-pyridazine-3-carboxylic acid (2-fluoro-phenyl)amide;
6-[4-(2-Trifluoromethylbenzoyl)piperazin-1-yl]pyridazine-3-carboxylic acid (4-fluoro-phenyl)amide;
6-[4-(2-Trifluoromethylbenzoyl)piperazin-1-yl]pyridazine-3-carboxylic acid (2,4-difluoro-phenyl)amide;
6-[4-(2-Trifluoromethylbenzoyl)piperazin-1-yl]pyridazine-3-carboxylic acid (2,5-difluoro-phenyl)amide;
6-[4-(2-Trifluoromethylbenzoyl)piperazin-1-yl]-pyridazine-3-carboxylic acid (3,4-difluoro-phenyl)amide;
6-[4-(2-Trifluoromethylbenzoyl)piperazin-1-yl]-pyridazine-3-carboxylic acid (2,3-difluoro-phenyl)amide;
6-[4-(2-Trifluoromethylbenzoyl)piperazin-1-yl]pyridazine-3-carboxylic acid (2,6-difluoro-phenyl)amide;
6-[4-(2-Trifluoromethylbenzoyl)piperazin-1-yl]pyridazine-3-carboxylic acid (4-cyano-phenyl)-amide;
6-[4-(2-Trifluoromethylbenzoyl)piperazin-1-yl]pyridazine-3-carboxylic acid (2-cyano-phenyl)-amide;
6-[4-(2-Trifluoromethylbenzoyl)piperazin-1-yl]pyridazine-3-carboxylic acid (3-cyano-phenyl)amide;
6-[4-(2-Trifluoromethylbenzoyl)piperazin-1-yl]pyridazine-3-carboxylic acid (3-chloro-phenyl)amide;
6-[4-(2-Trifluoromethylbenzoyl)piperazin-1-yl]pyridazine-3-carboxylic acid (3-chloro-2-methylphenyl)amide;
6-[4-(2-Trifluoromethylbenzoyl)piperazin-1-yl]pyridazine-3-carboxylic acid (2-chloro-3-methylphenyl)amide;
6-[4-(2-Trifluoromethylbenzoyl)piperazin-1-yl]pyridazine-3-carboxylic acid (2,5-dichlorophenyl)amide;
6-[4-(2-Trifluoromethylbenzoyl)piperazin-1-yl]pyridazine-3-carboxylic acid (2-chloro-5-methylphenyl)amide;
6-[4-(2-Trifluoromethylbenzoyl)piperazin-1-yl]pyridazine-3-carboxylic acid (2-chloro-6-methylphenyl)amide;
6-[4-(2-Trifluoromethylbenzoyl)piperazin-1-yl]pyridazine-3-carboxylic acid (4-chloro-2-methylphenyl)amide;
6-[4-(2-Trifluoromethylbenzoyl)piperazin-1-yl]pyridazine-3-carboxylic acid (4-chloro-3-methylphenyl)amide;
6-[4-(2-Trifluoromethylbenzoyl)piperazin-1-yl]pyridazine-3-carboxylic acid (3-chloro-4-methylphenyl)amide;
6-[4-(2-Trifluoromethylbenzoyl)piperazin-1-yl]pyridazine-3-carboxylic acid (2-chloro-4-methylphenyl)amide;
6-[4-(2-Trifluoromethylbenzoyl)piperazin-1-yl]pyridazine-3-carboxylic acid (2-chloro-5-fluorophenyl)amide;
6-[4-(2-Trifluoromethylbenzoyl)piperazin-1-yl]pyridazine-3-carboxylic acid (5-chloro-2-fluorophenyl)amide;
6-[4-(2-Trifluoromethylbenzoyl)piperazin-1-yl]pyridazine-3-carboxylic acid (2,5-difluorophenyl)amide;
6-[4-(2-Trifluoromethylbenzoyl)piperazin-1-yl]pyridazine-3-carboxylic acid (2,6-dichlorophenyl)amide;
6-[4-(2-Trifluoromethylbenzoyl)piperazin-1-yl]pyridazine-3-carboxylic acid (2-trifluoromethylphenyl)amide;
6-[4-(2-Trifluoromethylbenzoyl)piperazin-1-yl]pyridazine-3-carboxylic acid (4-trifluoromethylphenyl)amide;
6-[4-(2-Trifluoromethylbenzoyl)-piperazin-1-yl]pyridazine-3-carboxylic acid (3-trifluoromethylphenyl)amide;
6-[4-(2-Trifluoromethylbenzoyl)piperazin-1-yl]pyridazine-3-carboxylic acid phenylamide;
6-[4-(2-Trifluoromethylbenzoyl)piperazin-1-yl]pyridazine-3-carboxylic acid (5-chloro-2-methoxyphenyl)amide;
6-[4-(2-Trifluoromethylbenzoyl)piperazin-1-yl]pyridazine-3-carboxylic acid (2,5-dimethoxyphenyl)amide;
6-[4-(2-Trifluoromethylbenzoyl)piperazin-1-yl]pyridazine-3-carboxylic acid (2-chloro-4-methoxyphenyl)amide;
6-[4-(2-Trifluoromethylbenzoyl)-piperazin-1-yl]pyridazine-3-carboxylic acid (4-methoxy-phenyl)amide;
6-[4-(2-Trifluoromethylbenzoyl)piperazin-1-yl]pyridazine-3-carboxylic acid (2-methoxyphenyl)amide;
6-[4-(2-Trifluoromethylbenzoyl)piperazin-1-yl]pyridazine-3-carboxylic acid (3-methoxyphenyl)amide;
4-({6-[4-(2-Trifluoromethylbenzoyl)piperazin-1-yl]pyridazine-3-carbonyl}amino)-benzoic acid methyl ester;
4-({6-[4-(2-Trifluoromethylbenzoyl)piperazin-1-yl]pyridazine-3-carbonyl}amino)-benzoic acid;
2-({6-[4-(2-Trifluoromethylbenzoyl)piperazin-1-yl]pyridazine-3-carbonyl}amino)-benzoic acid methyl ester;
2-({6-[4-(2-Trifluoromethylbenzoyl)piperazin-1-yl]pyridazine-3-carbonyl}amino)-benzoic acid;
6-[4-(2-Trifluoromethylbenzoyl)piperazin-1-yl]pyridazine-3-carboxylic acid (3,4-dichlorophenyl)amide;
6-[4-(2-Trifluoromethylbenzoyl)piperazin-1-yl]pyridazine-3-carboxylic acid (5-chloro-pyridin-2-yl)amide;
6-[4-(2-Trifluoromethylbenzoyl)piperazin-1-yl]pyridazine-3-carboxylic acid (5-trifluoromethylpyridin-2-yl)amide;
6-[4-(2-Trifluoromethylbenzoyl)piperazin-1-yl]pyridazine-3-carboxylic acid (7H-purin-6-yl)amide;
6-[4-(2-Trifluoromethylbenzoyl)piperazin-1-yl]pyridazine-3-carboxylic acid pyrazin-2-ylamide;
6-[4-(2-Trifluoromethylbenzoyl)piperazin-1-yl]-pyridazine-3-carboxylic acid (1H-tetrazol-5-yl)amide;
6-[4-(2-Trifluoromethylbenzoyl)piperazin-1-yl]pyridazine-3-carboxylic acid (2H-[1,2,4]triazol-3-yl)amide;
6-[4-(2-Trifluoromethylbenzoyl)piperazin-1-yl]pyridazine-3-carboxylic acid (3-methyl-isoxazol-5-yl)amide;
6-[4-(2-Trifluoromethylbenzoyl)piperazin-1-yl]-pyridazine-3-carboxylic acid (5-methyl-isoxazol-3-yl)amide;
6-[4-(2-Trifluoromethylbenzoyl)piperazin-1-yl]-pyridazine-3-carboxylic acid (1H-pyrazol-3-yl)amide;
6-[4-(2-Trifluoromethylbenzoyl)piperazin-1-yl]-pyridazine-3-carboxylic acid (5-methyl-1H-pyrazol-3-yl)amide;
6-[4-(2-Trifluoromethylbenzoyl)piperazin-1-yl]-pyridazine-3-carboxylic acid pyrimidin-2-ylamide;
6-[4-(2-Trifluoromethylbenzoyl)piperazin-1-yl]-pyridazine-3-carboxylic acid pyrazin-2-ylamide;
6-[4-(2-Trifluoromethylbenzoyl)piperazin-1-yl]-pyridazine-3-carboxylic acid (4-methyl-pyrimidin-2-yl)amide;
6-[4-(2-Trifluoromethylbenzoyl)piperazin-1-yl]-pyridazine-3-carboxylic acid (2-oxo-2,3-dihydro-pyrimidin-4-yl)amide;
6-[4-(2-Trifluoromethylbenzoyl)piperazin-1-yl]-pyridazine-3-carboxylic acid (6-oxo-1,6-dihydro-pyrimidin-2-yl)amide;
6-[4-(2-Trifluoromethylbenzoyl)piperazin-1-yl]-pyridazine-3-carboxylic acid [1,3,4]thiadiazol-2-ylamide;
6-[4-(2-Trifluoromethylbenzoyl)piperazin-1-yl]-pyridazine-3-carboxylic acid thiazol-2-ylamide;
6-[4-(2-Trifluoromethyl-benzoyl)piperazin-1-yl]pyridazine-3-carboxylic acid pyridin-2-ylamide;
6-[4-(2-Trifluoromethyl-benzoyl)piperazin-1-yl]pyridazine-3-carboxylic acid pyridazin-3-ylamide;
6-[4-(2-Trifluoromethyl-benzoyl)piperazin-1-yl]pyridazine-3-carboxylic acid pyridin-3-ylamide;
6-[4-(2-Trifluoromethylbenzoyl)piperazin-1-yl]pyridazine-3-carboxylic acid pyridin-4-ylamide;
6-[4-(2-Trifluoromethylbenzoyl)piperazin-1-yl]pyridazine-3-carboxylic acid (6-oxo-1,6-dihydro-[1,3,5]triazin-2-yl)amide;
6-[4-(2-Trifluoromethylbenzoyl)piperazin-1-yl]pyridazine-3-carboxylic acid (5-fluoro-pyridin-2-yl)-amide;

6-[4-(2-Trifluoromethyl-benzoyl)-piperazin-1-yl]-pyridazine-3-carboxylic acid (5-cyano-pyridin-2-yl)-amide;
6-[4-(2-Trifluoromethyl-benzoyl)-piperazin-1-yl]-pyridazine-3-carboxylic acid (4,6-dimethyl-pyrimidin-2-yl)-amide;
6-[4-(2-Trifluoromethyl-benzoyl)-piperazin-1-yl]-pyridazine-3-carboxylic acid (2-chloro-pyridin-4-yl)-amide;
6-[4-(2-Trifluoromethyl-benzoyl)-piperazin-1-yl]-pyridazine-3-carboxylic acid (1H-indol-6-yl)-amide;
6-[4-(2-Trifluoromethyl-benzoyl)-piperazin-1-yl]-pyridazine-3-carboxylic acid (1H-indol-4-yl)-amide;
6-[4-(2-Trifluoromethyl-benzoyl)-piperazin-1-yl]-pyridazine-3-carboxylic acid (1H-indazol-5-yl)-amide;
6-[4-(2-Trifluoromethyl-benzoyl)-piperazin-1-yl]-pyridazine-3-carboxylic acid (1H-indazol-6-yl)-amide;
6-[4-(2-Trifluoromethyl-benzoyl)-piperazin-1-yl]-pyridazine-3-carboxylic acid (4-methyl-thiazol-2-yl)-amide;
6-[4-(2-Trifluoromethyl-benzoyl)-piperazin-1-yl]-pyridazine-3-carboxylic acid (5-methyl-thiazol-2-yl)-amide;
6-[4-(2-Trifluoromethyl-benzoyl)-piperazin-1-yl]-pyridazine-3-carboxylic acid (5-thioxo-4,5-dihydro-1H-[1,2,4]triazol-3-yl)-amide;
6-[4-(2-Trifluoromethylbenzoyl)piperazin-1-yl]-pyridazine-3-carboxylic acid (1H-benzoimidazol-2-yl)-amide;
6-[4-(2-Trifluoromethylbenzoyl)piperazin-1-yl]pyridazine-3-carboxylic acid (6-methylpyridazin-3-yl)amide;
6-[4-(2-Trifluoromethylbenzoyl)piperazin-1-yl]pyridazine-3-carboxylic acid (6-methoxypyridazin-3-yl)amide;
6-[4-(2-Trifluoromethylbenzoyl)-piperazin-1-yl]-pyridazine-3-carboxylic acid (6-chloro-pyridazin-3-yl)-amide;
6-[4-(2-Trifluoromethylbenzoyl)piperazin-1-yl]-pyridazine-3-carboxylic acid indan-1-ylamide;
6-[4-(2-Trifluoromethylbenzoyl)piperazin-1-yl]-pyridazine-3-carboxylic acid (2-oxo-1,3-diaza-bicyclo[3.1.0]hex-3-en-4-yl)amide;
6-[4-(2-Trifluoromethylbenzoyl)piperazin-1-yl]-pyridazine-3-carboxylic acid (5-oxo-4,5-dihydro-1H-pyrazol-3-yl)amide;
6-[4-(2-Trifluoromethylbenzoyl)piperazin-1-yl]-pyridazine-3-carboxylic acid indan-5-ylamide;
5-[1,2]Dithiolan-3-yl-pentanoic acid {6-[4-(2-trifluoromethyl-benzoyl)-piperazin-1-yl]-pyridazin-3-yl}-amide;
6-[4-(2-Trifluoromethylbenzoyl)-piperazin-1-yl]-pyridazine-3-carboxylic acid (2-thiophen-2-yl-ethyl)-amide;
6-[4-(2-Trifluoromethylbenzoyl)piperazin-1-yl]pyridazine-3-carboxylic acid (2-benzo[1,3]dioxol-5-yl-ethyl)amide;
6-[4-(2-Trifluoromethylbenzoyl)piperazin-1-yl]pyridazine-3-carboxylic acid (2,2-difluoro-2-pyridin-2-ylethyl)amide;
6-[4-(2-Trifluoromethylbenzoyl)piperazin-1-yl]pyridazine-3-carboxylic acid (2-pyridin-2-ylethyl)amide;
6-[4-(2-Trifluoromethylbenzoyl)piperazin-1-yl]pyridazine-3-carboxylic acid (pyridin-2-yl-methyl)amide;
4-Cyclohexyl-N-{6-[4-(2-trifluoromethylbenzoyl)piperazin-1-yl]pyridazin-3-yl}butyramide;
2,2,3,3-Tetramethylcyclopropanecarboxylic acid {6-[4-(2-trifluoromethylbenzoyl)piperazin-1-yl]pyridazin-3-yl}amide;
Cyclopropanecarboxylic acid {6-[4-(2-trifluoromethyl-benzoyl)piperazin-1-yl]pyridazin-3-yl}amide;
1-Trifluoromethylcyclopropanecarboxylic acid {6-[4-(2-trifluoromethylbenzoyl)piperazin-1-yl]pyridazin-3-yl}amide;
2-Phenylcyclopropanecarboxylic acid {6-[4-(2-trifluoromethylbenzoyl)piperazin-1-yl]pyridazin-3-yl}amide;
2-Benzyloxy-N-{6-[4-(2-trifluoromethylbenzoyl)piperazin-1-yl]pyridazin-3-yl}acetamide;
2-Ethoxy-N-{6-[4-(2-trifluoromethylbenzoyl)piperazin-1-yl]pyridazin-3-yl}acetamide;
2-Cyclopropylmethoxy-N-{6-[4-(2-trifluoromethylbenzoyl)-piperazin-1-yl]pyridazin-3-yl}acetamide;
2-(2-Methoxyethoxy)-N-{6-[4-(2-trifluoromethylbenzoyl)-piperazin-1-yl]pyridazin-3-yl}acetamide;
N-{6-[4-(2-Trifluoromethylbenzoyl)piperazin-1-yl]pyridazin-3-yl}-2-(3,3,3-trifluoropropoxy)acetamide;
3-Methoxy-N-{6-[4-(2-trifluoromethylbenzoyl)piperazin-1-yl]pyridazin-3-yl}propionamide;
3-Phenoxy-N-{6-[4-(2-trifluoromethylbenzoyl)piperazin-1-yl]-pyridazin-3-yl}propionamide;
2-Butoxy-N-{6-[4-(2-trifluoromethylbenzoyl)piperazin-1-yl]pyridazin-3-yl}acetamide;
2-Methyl-1-{6-[4-(2-trifluoromethylbenzoyl)piperazin-1-yl]pyridazin-3-ylcarbamoyl}propylamine;
2-Phenoxy-N-{6-[4-(2-trifluoromethylbenzoyl)piperazin-1-yl]pyridazin-3-yl}acetamide;
{6-[4-(2-Trifluoromethylbenzoyl)piperazin-1-yl]pyridazin-3-yl}carbamic acid butyl ester;
{6-[4-(2-Trifluoromethylbenzoyl)piperazin-1-yl]pyridazin-3-yl}carbamic acid propyl ester;
{6-[4-(2-Trifluoromethylbenzoyl)piperazin-1-yl]pyridazin-3-yl}carbamic acid isobutyl ester;
{6-[4-(2-Trifluoromethylbenzoyl)piperazin-1-yl]pyridazin-3-yl}carbamic acid ethyl ester;
Hexanoic Acid {6-[4-(2-trifluoromethylbenzoyl)piperazin-1-yl]-pyridazin-3-yl}amide;
4-Fluoro-N-{6-[4-(2-trifluoromethylbenzoyl)piperazin-1-yl]-pyridazin-3-yl}benzamide;
{6-[4-(2-Trifluoromethylbenzoyl)piperazin-1-yl]pyridazin-3-yl}carbamic acid 3,3-dimethylbutyl ester;
{6-[4-(2-Trifluoromethylbenzoyl)piperazin-1-yl]pyridazin-3-yl}carbamic acid 2-cyclopropylethyl ester;
4-(4-Methoxyphenyl)-N-{6-[4-(2-trifluoromethylbenzoyl)-piperazin-1-yl]pyridazin-3-yl}butyramide;
3-(4-Fluorophenyl)-N-{6-[4-(2-trifluoromethylbenzoyl)-piperazin-1-yl]-pyridazin-3-yl}propionamide;
6-[4-(2-Trifluoromethylbenzoyl)piperazin-1-yl]pyridazine-3-carboxylic acid (2-cyclopropylethyl)amide;
6-[4-(5-Fluoro-2-trifluoromethylbenzoyl)piperazin-1-yl]pyridazine-3-carboxylic acid (2-cyclopropylethyl)amide;
6-[4-(2-Trifluoromethylbenzoyl)piperazin-1-yl]pyridazine-3-carboxylic acid cyclopropylmethylamide;
4-Methyl-2-({6-[4-(2-trifluoromethylbenzoyl)piperazin-1-yl]-pyridazine-3-carbonyl}amino)pentanoic acid methyl ester;
6-[4-(2-Trifluoromethylbenzoyl)piperazin-1-yl]pyridazine-3-carboxylic acid (3-methylbutyl)amide;
6-[4-(5-Fluoro-2-trifluoromethylbenzoyl)piperazin-1-yl]pyridazine-3-carboxylic acid (3-methylbutyl)amide;
6-[4-(4-Fluoro-2-trifluoromethylbenzoyl)piperazin-1-yl]pyridazine-3-carboxylic acid (3-methylbutyl)amide;
4-Methyl-2-({6-[4-(2-trifluoromethylbenzoyl)piperazin-1-yl]pyridazine-3-carbonyl}amino)pentanoic acid;
6-[4-(2-Trifluoromethylbenzoyl)piperazin-1-yl]pyridazine-3-carboxylic acid phenethylamide;
6-[4-(2-Trifluoromethylbenzoyl)piperazin-1-yl]pyridazine-3-carboxylic acid [2-(4-methoxyphenyl)ethyl]amide;
6-[4-(2-Trifluoromethylbenzoyl)piperazin-1-yl]pyridazine-3-carboxylic acid [2-(3-fluorophenyl)ethyl]amide;
6-[4-(2-Trifluoromethylbenzoyl)piperazin-1-yl]pyridazine-3-carboxylic acid (3-phenylpropyl)amide;
6-[4-(2-Trifluoromethylbenzoyl)piperazin-1-yl]pyridazine-3-carboxylic acid [2-(4-fluorophenyl)ethyl]amide;

3-Cyclopentyl-N-{6-[4-(2-trifluoromethylbenzoyl)piper-azin-1-yl]pyridazin-3-yl}propionamide;
4-Methylpentanoic acid {6-[4-(2-trifluoromethylbenzoyl)-piperazin-1-yl]pyridazin-3-yl}amide; and
4-Phenyl-N-{6-[4-(2-trifluoromethylbenzoyl)piperazin-1-yl]pyridazin-3-yl}butyramide.

In another embodiment of the invention, the SCD-1 inhibitors are compounds of formula (I) as set forth above in the Summary of the Invention wherein:

L and M are each —N═;
G and J are each —C($R^4$)═;
x and y are each 1;
W is —N($R^1$)C(O)N($R^1$)—;
V is —C(O)—;

each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxy;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, aryl, $C_7$-$C_{12}$aralkyl, $C_1$-$C_{12}$heteroaryl, and $C_3$-$C_{12}$heteroarylalkyl;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$ hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

$R^4$ and $R^5$ are each independently selected from hydrogen, fluoro, chloro, methyl, methoxy and trifluoromethyl; and $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

or $R^5$ and $R^{5a}$ together or $R^7$ and $R^{7a}$ together are an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl.

Of this embodiment, a preferred embodiment of a compound of formula (I) is selected from the group consisting of the following:

1-(2-Phenylcyclopropyl)-3-{6-[4-(2-trifluoromethylbenzoyl)piperazin-1-yl]pyridazin-3-yl}urea;
1-Cyclopentyl-3-{6-[4-(2-trifluoromethylbenzoyl)piperazin-1-yl]-pyridazin-3-yl}urea;
1-(3-Cyclopropylpropyl)-3-{6-[4-(2-trifluoromethylbenzoyl)piperazin-1-yl]pyridazin-3-yl}urea;
1-Cyclopropylmethyl-3-{6-[4-(2-trifluoromethylbenzoyl)piperazin-1-yl]pyridazin-3-yl}urea;
1-(2-Cyclopropylethyl)-3-{6-[4-(2-trifluoromethylbenzoyl)piperazin-1-yl]pyridazin-3-yl}urea;
1-(2-Cyclopropylethyl)-3-{6-[4-(2-fluoro-6-trifluoromethylbenzoyl)piperazin-1-yl]pyridazin-3-yl}urea;
1-(2-Cyclopropylethyl)-3-{6-[4-(5-fluoro-2-trifluoromethylbenzoyl)piperazin-1-yl]pyridazin-3-yl}urea;
1-Cyclohexyl-3-{6-[4-(2-trifluoromethylbenzoyl)piperazin-1-yl]pyridazin-3-yl}urea
1-(2-Cyclopropylethyl)-3-{6-[4-(2,6-difluorobenzoyl)piperazin-1-yl]pyridazin-3-yl}urea;
1-(3-Cyclopropylpropyl)-3-{6-[4-(5-fluoro-2-trifluoromethylbenzoyl)piperazin-1-yl]pyridazin-3-yl}urea;
1-[1-(4-Fluorophenyl)ethyl]-3-{6-[4-(2-trifluoromethylbenzoyl)piperazin-1-yl]pyridazin-3-yl}urea;
1-[1-(4-Fluorophenyl)ethyl]-3-{6-[4-(2-trifluoromethylbenzoyl)piperazin-1-yl]pyridazin-3-yl}urea;
1-[3-(4-Fluorophenyl)propyl]-3-{6-[4-(2-trifluoromethylbenzoyl)piperazin-1-yl]pyridazin-3-yl}urea;
1-Phenethyl-3-{6-[4-(2-trifluoromethylbenzoyl)piperazin-1-yl]-pyridazin-3-yl}urea;
1-(4-Fluorobenzyl)-3-{6-[4-(2-trifluoromethylbenzoyl)piperazin-1-yl]pyridazin-3-yl}urea;
1-(3,4-Dichlorobenzyl)-3-{6-[4-(2-trifluoromethylbenzoyl)piperazin-1-yl]pyridazin-3-yl}urea;
1-(4-Fluorophenyl)-3-{6-[4-(2-trifluoromethylbenzoyl)piperazin-1-yl]-pyridazin-3-yl}urea; and
1-(2-Fluorophenyl)-3-{6-[4-(2-trifluoromethylbenzoyl)piperazin-1-yl]pyridazin-3-yl}urea;
3-(3-{6-[4-(2-Trifluoromethylbenzoyl)piperazin-1-yl]-pyridazin-3-yl}ureido)propionic acid ethyl ester;
1-Butyl-3-{6-[4-(2-trifluoromethylbenzoyl)piperazin-1-yl]pyridazin-3-yl}urea;
1-(2-chloroethyl)-3-{6-[4-(2-trifluoromethylbenzoyl)-piperazin-1-yl]pyridazin-3-yl}urea;
1-{6-[4-(2,6-Difluorobenzoyl)piperazin-1-yl]pyridazin-3-yl}-3-(3-methylbutyl)urea;
1-(3,3-Dimethylbutyl)-3-{6-[4-(2-trifluoromethylbenzoyl)piperazin-1-yl]pyridazin-3-yl}urea;
1-(2-Isopropoxyethyl)-3-{6-[4-(2-trifluoromethylbenzoyl)-piperazin-1-yl]pyridazin-3-yl}urea;
1-(3-Hydroxy-4,4-dimethylpentyl)-3-{6-[4-(2-trifluoromethylbenzoyl)piperazin-1-yl]pyridazin-3-yl}urea;
1-Hexyl-3-{6-[4-(2-trifluoromethylbenzoyl)piperazin-1-yl]pyridazin-3-yl}urea;
1-Heptyl-3-{6-[4-(2-trifluoromethylbenzoyl)piperazin-1-yl]pyridazin-3-yl}urea;
1-(4-Methylpentyl)-3-{6-[4-(2-trifluoromethylbenzoyl)piperazin-1-yl]pyridazin-3-yl}urea;
1-Benzyl-3-{6-[4-(2-trifluoromethylbenzoyl)piperazin-1-yl]pyridazin-3-yl}urea; and
1-Pentyl-3-{6-[4-(2-trifluoromethylbenzoyl)piperazin-1-yl]pyridazin-3-yl}urea.

In another embodiment of the invention, the SCD-1 inhibitors are compounds of formula (I) as set forth above in the Summary of the Invention wherein:

L and M are each —N═;
G and J are each —C($R^4$)═;
x and y are each 1;
W is —C(O)N($R^1$)—; —N($R^1$)C(O)N($R^1$)— or —N($R^1$)C(O)—;
V is —C($R^{10}$)—;

each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxy;

$R^2$ is selected from the group consisting of $C_7$-$C_{12}$alkyl, $C_2$-$C_{12}$alkenyl, $C_7$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, $C_{13}$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

each $R^4$ is independently selected from hydrogen, fluoro, chloro, methyl, methoxy, trifluoromethyl, cyano, nitro or $-N(R^9)_2$;

$R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

or $R^5$ and $R^{5a}$ together, or $R^6$ and $R^{6a}$ together, or $R^7$ and $R^{7a}$ together, or $R^8$ and $R^{8a}$ together are an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

$R^{10}$ is hydrogen or $C_1$-$C_3$alkyl; and each $R^9$ is independently selected from hydrogen or $C_1$-$C_6$alkyl;

provided, however, that $R^2$ can not be pyrazinyl, pyridinonyl, pyrrolidinonyl or imidazolyl.

Of this embodiment, a preferred embodiment of a compound of formula (I) is selected from the group consisting of the following:

6-[4-(2-Trifluoromethylbenzyl)piperazin-1-yl]pyridazine-3-carboxylic acid (2-cyclopropylethyl)amide;

6-[4-(5-Fluoro-2-trifluoromethylbenzyl)piperazin-1-yl]pyridazine-3-carboxylic acid (2-cyclopropylethyl)amide;

6-[4-(4-Fluoro-2-trifluoromethylbenzyl)-piperazin-1-yl]pyridazine-3-carboxylic acid (2-cyclopropylethyl)amide;

6-[4-(5-Chloro-2-trifluoromethylbenzyl)piperazin-1-yl]pyridazine-3-carboxylic acid (2-cyclopropylethyl)amide;

6-[4-(2-Chloro-4-fluorobenzyl)piperazin-1-yl]pyridazine-3-carboxylic acid (2-cyclopropylethyl)amide;

6-[4-(2,5-Dichlorobenzyl)piperazin-1-yl]pyridazine-3-carboxylic acid (2-cyclopropylethyl)amide;

6-[4-(2,4-Dichlorobenzyl)piperazin-1-yl]pyridazine-3-carboxylic acid (2-cyclopropylethyl)amide;

6-[4-(5-Fluoro-2-trifluoromethylbenzyl)piperazin-1-yl]pyridazine-3-carboxylic acid (3-cyclopropylpropyl)amide; and 6-{4-[1-(2-Trifluoromethylphenyl)ethyl]piperazin-1-yl}-pyridazine-3-carboxylic acid (2-cyclopropylethyl)amide.

In another embodiment of the invention, the SCD-1 inhibitors are compounds of formula (I) as set forth above in the Summary of the Invention wherein:

L and M are each $-N=$;
G and J are each $-C(R^4)-$;
x and y are each 1;
W is $-C(O)N(R^1)-$; $-N(R^1)C(O)N(R^1)-$ or $-N(R^1)C(O)-$;
V is $-C(R^{10})-$;

each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxy;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

$R^3$ is selected from the group consisting of $C_7$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy or $C_2$-$C_{12}$alkoxyalkyl each $R^4$ is independently selected from hydrogen, fluoro, chloro, methyl, methoxy, trifluoromethyl, cyano, nitro or $-N(R^9)_2$;

$R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

or $R^5$ and $R^{5a}$ together, or $R^6$ and $R^{6a}$ together, or $R^7$ and $R^{7a}$ together, or $R^8$ and $R^{8a}$ together are an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

$R^{10}$ is hydrogen or $C_1$-$C_3$alkyl; and each $R^9$ is independently selected from hydrogen or $C_1$-$C_6$alkyl.

In another embodiment of the invention, the SCD-1 inhibitors are compounds of formula (I) as set forth above in the Summary of the Invention wherein:

x and y are each 1;
G, J and M are each $-C(R^4)-$;
L is $-N=$;
W is $-O-$, $-N(R^1)-$, $-C(O)-$, $-S(O)_t-$; (where t is 0, 1 or 2), $-N(R^1)S(O)_2-$, $-S(O)_2N(R^1)-$, $-OS(O)_2N(R^1)-$, $-C(O)N(R^1)-$, $-OC(O)N(R^1)-$, $-C(S)N(R^1)-$, $-OC(S)N(R^1)-$, $-N(R^1)C(O)-$ or $-N(R^1)C(O)N(R^1)-$;

V is $-C(O)-$, $-C(S)-$, $-C(O)N(R^1)-$, $-C(O)O-$, $-S(O)_2-$, $-S(O)_2N(R^1)-$ or $-C(R^{10})H-$;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

each $R^4$ is independently selected from hydrogen, fluoro, chloro, methyl, methoxy, trifluoromethyl, cyano, nitro or $-N(R^9)_2$;

$R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

or $R^5$ and $R^{5a}$ together, or $R^6$ and $R^{6a}$ together, or $R^7$ and $R^{7a}$ together, or $R^8$ and $R^{8a}$ together are an oxo group, provided that when V is $-C(O)-$, $R^8$ and $R^{8a}$ together or $R^6$ and $R^{6a}$ together do not form an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

$R^{10}$ is hydrogen or $C_1$-$C_3$alkyl; and each $R^9$ is independently selected from hydrogen or $C_1$-$C_6$alkyl.

In another embodiment of the invention, the SCD-1 inhibitors are compounds of formula (I) as set forth above in the Summary of the Invention wherein:

x and y are each 1;
G, J and M are each $-C(R^4)-$;
L is $-N=$;
W is $-C(O)N(R^1)-$;
V is $-C(O)-$;

$R^1$ is selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_7$-$C_{12}$alkyl, $C_3$-$C_{12}$alkenyl, $C_7$-$C_{12}$hydroxyalkyl, $C_1$-$C_{12}$alkoxy, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_1$-$C_{12}$heteroaryl, $C_3$-$C_{12}$heterocyclylalkyl and $C_3$-$C_{12}$heteroarylalkyl, provided that $R^2$ is not pyrazinyl, pyridinonyl, pyrrolidinone or imidazolyl;

$R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$ heteroaryl and $C_3$-$C_{12}$heteroarylalkyl;

each $R^4$ is independently selected from hydrogen, fluoro, chloro, methyl, methoxy, trifluoromethyl, cyano, nitro or —N($R^9$)$_2$;

$R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

or $R^7$ and $R^{7a}$ together or $R^5$ and $R^{5a}$ together form an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl; and each $R^9$ is independently selected from hydrogen or $C_1$-$C_6$alkyl.

In another embodiment of the invention, the SCD-1 inhibitors are compounds of formula (I) as set forth above in the Summary of the Invention wherein:

x and y are each 1;
G, J and M are each —C($R^4$)—;
L is —N=;
W is —C(O)N($R^1$)—;
V is —C(O)—;

$R^1$ is selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

or $R^2$ is phenyl optionally substituted with one or more substituents selected from halo and $C_1$-$C_6$trihaloalkyl;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{11}$)$_2$, —OC(O)$R^{11}$, —C(O)O$R^{11}$, —S(O)$_2$N($R^{11}$)$_2$, cycloalkyl, heterocyclyl, heteroaryl and heteroarylcycloalkyl, provided that $R^3$ is not phenyl substituted with optionally substituted thienyl;

each $R^4$ is independently selected from hydrogen, fluoro, chloro, methyl, methoxy, trifluoromethyl, cyano, nitro or —N($R^9$)$_2$;

$R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

or $R^7$ and $R^{7a}$ together or $R^5$ and $R^{5a}$ together form an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

each $R^{11}$ is independently selected from hydrogen, $C_1$-$C_6$alkyl, $C_3$-$C_6$cycloalkyl, aryl or aralkyl; and each $R^9$ is independently selected from hydrogen or $C_1$-$C_6$alkyl.

Of this embodiment, a preferred embodiment of a compound of formula (I) is selected from the group consisting of the following:

3-(4-Fluoro-phenyl)-N-{5-[4-(2-trifluoromethyl-benzoyl)-piperazin-1-yl]-pyridin-2-yl}-propionamide;
4-Phenyl-N-{5-[4-(2-trifluoromethyl-benzoyl)-piperazin-1-yl]-pyridin-2-yl}-butyramide;
4-(4-Fluoro-phenyl)-N-{5-[4-(2-trifluoromethyl-benzoyl)-piperazin-1-yl]-pyridin-2-yl}-butyramide;
3-Phenyl-N-{5-[4-(2-trifluoromethyl-benzoyl)-piperazin-1-yl]-pyridin-2-yl}-propionamide;
Hexanoic acid {5-[4-(2-trifluoromethyl-benzoyl)-piperazin-1-yl]-pyridin-2-yl}-amide;
Heptanoic acid {5-[4-(2-trifluoromethyl-benzoyl)-piperazin-1-yl]-pyridin-2-yl}-amide;
5-Methylpentanoic acid {5-[4-(2-trifluoromethyl-benzoyl)-piperazin-1-yl]-pyridin-2-yl}-amide;
3-Pyridin-3-yl-N-{5-[4-(2-trifluoromethyl-benzoyl)-piperazin-1-yl]-pyridin-2-yl}-propionamide; and
4-Fluoro-N-{5-[4-(2-trifluoromethylbenzoyl)piperazin-1-yl]pyridin-2-yl}benzamide.

In another embodiment of the invention, the SCD-1 inhibitors are compounds of formula (I) as set forth above in the Summary of the Invention wherein:

x and y are each 1;
G, J and M are each —C($R^4$)—;
L is —N=;
W is —S(O)$_2$N($R^1$)—;
V is —C(O)—, —C(S)—, —C(O)N($R^1$)—, —C(O)O—, —S(O)$_2$— or —S(O)$_2$N($R^1$)—;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

each $R^4$ is independently selected from hydrogen, fluoro, chloro, methyl, methoxy, trifluoromethyl, cyano, nitro or —N($R^9$)$_2$;

$R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

or $R^5$ and $R^{5a}$ together, or $R^6$ and $R^{6a}$ together, or $R^7$ and $R^{7a}$ together, or $R^8$ and $R^{8a}$ together are an oxo group, provided that when $V_a$ is —C(O)—, $R^8$ and $R^{8a}$ together or $R^6$ and $R^{6a}$ together do not form an oxo group, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl; and each $R^9$ is independently selected from hydrogen or $C_1$-$C_6$alkyl.

Of this embodiment, a preferred embodiment of a compound of formula (I) is selected from the group consisting of the following:

Pentane-1-sulfonic acid {5-[4-(2-trifluoromethyl-benzoyl)-piperazin-1-yl]-pyridin-2-yl}-amide;
Hexane-1-sulfonic acid {5-[4-(2-trifluoromethyl-benzoyl)-piperazin-1-yl]-pyridin-2-yl}-amide; and
3-Phenyl-propane-1-sulfonic acid {5-[4-(2-trifluoromethyl-benzoyl)-piperazin-1-yl]-pyridin-2-yl}-amide.

In another embodiment of the invention, the SCD-1 inhibitors are compounds of formula (I) as set forth above in the Summary of the Invention wherein:

x and y are each 1;
G, J and M are each —C($R^4$)—;

L is —N=;

W is —N(R$^1$)C(O)N(R$^1$)—;

V is —C(O)—, —C(S)—, —C(O)N(R$^1$)—, —C(O)O—, —S(O)$_2$— or —S(O)$_2$N(R$^1$)—;

each R$^1$ is independently selected from the group consisting of hydrogen, C$_1$-C$_{12}$alkyl, C$_2$-C$_{12}$hydroxyalkyl, C$_4$-C$_{12}$cycloalkylalkyl and C$_7$-C$_{19}$aralkyl;

R$^2$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_3$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$ heterocyclyl, C$_3$-C$_{12}$heterocyclylalkyl, C$_1$-C$_{12}$heteroaryl and C$_3$-C$_{12}$heteroarylalkyl;

R$^3$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl and C$_3$-C$_{12}$heteroarylalkyl;

each R$^4$ is independently selected from hydrogen, fluoro, chloro, methyl, methoxy, trifluoromethyl, cyano, nitro or —N(R$^9$)$_2$;

R$^5$, R$^{5a}$, R$^6$, R$^{6a}$, R$^7$, R$^{7a}$, R$^8$, and R$^{8a}$ are each independently selected from hydrogen or C$_1$-C$_3$alkyl;

or R$^5$ and R$^{5a}$ together, or R$^6$ and R$^{6a}$ together, or R$^7$ and R$^{7a}$ together, or R$^8$ and R$^{8a}$ together are an oxo group, provided that when V$_a$ is —C(O)—, R$^8$ and R$^{8a}$ together or R$^6$ and R$^{6a}$ together do not form an oxo group, while the remaining R$^5$, R$^{5a}$, R$^6$, R$^{6a}$, R$^7$, R$^{7a}$, R$^8$, and R$^{8a}$ are each independently selected from hydrogen or C$_1$-C$_3$alkyl; and each R$^9$ is independently selected from hydrogen or C$_1$-C$_6$alkyl.

Of this embodiment, a preferred embodiment of a compound of formula (I) is selected from the group consisting of the following:

1-(3-Methyl-butyl)-3-{5-[4-(2-trifluoromethyl-benzoyl)-piperazin-1-yl]-pyridin-2-yl}-urea;

1-Pentyl-3-{5-[4-(2-trifluoromethyl-benzoyl)-piperazin-1-yl]-pyridin-2-yl}-urea;

1-Butyl-3-{5-[4-(2-trifluoromethyl-benzoyl)-piperazin-1-yl]-pyridin-2-yl}-urea;

1-[3-(4-Fluoro-phenyl)-propyl]-3-{5-[4-(2-trifluoromethyl-benzoyl)-piperazin-1-yl]-pyridin-2-yl}-urea;

1-Phenethyl-3-{5-[4-(2-trifluoromethyl-benzoyl)-piperazin-1-yl]-pyridin-2-yl}-urea; and 1-Benzyl-3-{5-[4-(2-trifluoromethyl-benzoyl)-piperazin-1-yl]-pyridin-2-yl}-urea.

In another embodiment of the invention, the SCD-1 inhibitors are compounds of formula (I) as set forth above in the Summary of the Invention wherein:

x and y are each 1;

G, J and M are each —C(R$^4$)—;

L is —N=;

W is —O—, —N(R$^1$)— or —S(O)$_t$— (where t is 0, 1 or 2);

V is —C(O)—, —C(S)—, —C(O)N(R$^1$)—, —C(O)O—, —S(O)$_2$— or —S(O)$_2$N(R$^1$)—;

each R$^1$ is independently selected from the group consisting of hydrogen, C$_1$-C$_{12}$alkyl, C$_2$-C$_{12}$hydroxyalkyl, C$_4$-C$_{12}$cycloalkylalkyl and C$_7$-C$_{19}$aralkyl;

R$^2$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_3$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$ heterocyclyl, C$_3$-C$_{12}$heterocyclylalkyl, C$_1$-C$_{12}$heteroaryl and C$_3$-C$_{12}$heteroarylalkyl;

R$^3$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl and C$_3$-C$_{12}$heteroarylalkyl;

each R$^4$ is independently selected from hydrogen, fluoro, chloro, methyl, methoxy, trifluoromethyl, cyano, nitro or —N(R$^9$)$_2$;

R$^5$, R$^{5a}$, R$^6$, R$^{6a}$, R$^7$, R$^{7a}$, R$^8$, and R$^{8a}$ are each independently selected from hydrogen or C$_1$-C$_3$alkyl;

or R$^5$ and R$^{5a}$ together, or R$^6$ and R$^{6a}$ together, or R$^7$ and R$^{7a}$ together, or R$^8$ and R$^{8a}$ together are an oxo group, provided that when V$_a$ is —C(O)—, R$^8$ and R$^{8a}$ together or R$^6$ and R$^{6a}$ together do not form an oxo group, while the remaining R$^5$, R$^{5a}$, R$^6$, R$^{6a}$, R$^7$, R$^{7a}$, R$^8$, and R$^{8a}$ are each independently selected from hydrogen or C$_1$-C$_3$alkyl; and each R$^9$ is independently selected from hydrogen or C$_1$-C$_6$alkyl.

In another embodiment of the invention, the SCD-1 inhibitors are compounds of formula (I) as set forth above in the Summary of the Invention wherein:

x and y are each 1;

G, J and M are each —C(R$^4$)—;

L is —N=;

W is —N(R$^1$)C(O)—;

V is —C(O)—;

R$^1$ is selected from the group consisting of hydrogen, C$_1$-C$_{12}$alkyl, C$_2$-C$_{12}$hydroxyalkyl, C$_4$-C$_{12}$cycloalkylalkyl and C$_7$-C$_{19}$aralkyl;

R$^2$ is selected from the group consisting of C$_7$-C$_{12}$alkyl, C$_3$-C$_{12}$alkenyl, C$_7$-C$_{12}$hydroxyalkyl, C$_2$-C$_{12}$alkoxyalkyl, C$_3$-C$_{12}$hydroxyalkenyl, C$_3$-C$_{12}$cycloalkyl, C$_4$-C$_{12}$cycloalkylalkyl, C$_{13}$-C$_{19}$aralkyl, C$_3$-C$_{12}$heterocyclylalkyl, and C$_3$-C$_{12}$heteroarylalkyl;

R$^3$ is selected from the group consisting of C$_3$-C$_{12}$alkyl, C$_3$-C$_{12}$alkenyl, C$_3$-C$_{12}$hydroxyalkyl, C$_3$-C$_{12}$hydroxyalkenyl, C$_3$-C$_{12}$alkoxy, C$_3$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_5$-C$_{12}$ heteroaryl and C$_3$-C$_{12}$heteroarylalkyl;

each R$^4$ is independently selected from hydrogen, fluoro, chloro, methyl, methoxy, trifluoromethyl, cyano, nitro or —N(R$^9$)$_2$;

R$^5$, R$^{5a}$, R$^6$, R$^{6a}$, R$^7$, R$^{7a}$, R$^8$, and R$^{8a}$ are each independently selected from hydrogen or C$_1$-C$_3$alkyl;

or R$^5$ and R$^{5a}$ together or R$^7$ and R$^{7a}$ together are an oxo group, while the remaining R$^5$, R$^{5a}$, R$^6$, R$^{6a}$, R$^7$, R$^{7a}$, R$^8$, and R$^{8a}$ are each independently selected from hydrogen or C$_1$-C$_3$alkyl; and each R$^9$ is independently selected from hydrogen or C$_1$-C$_6$alkyl.

In another embodiment of the invention, the SCD-1 inhibitors are compounds of formula (I) as set forth above in the Summary of the Invention wherein:

x and y are each 1;

G, J and M are each —C(R$^4$)—;

L is —N=;

W is —N(R$^1$)C(O)—;

V is —C(O)—;

each R¹ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

R² is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

R³ is naphthyl or phenyl, each optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N(R¹¹)₂, —OC(O)R¹¹, —C(O)OR¹¹, —S(O)₂N(R¹¹)₂, cycloalkyl, heterocyclyl, heteroaryl and heteroarylcycloalkyl, provided that R³ is not phenyl substituted with optionally substituted thienyl, and provided that when R³ is naphthyl, R² can not be $C_1$-$C_6$alkyl, $C_2$-$C_6$hydroxyalkyl or phenyl substituted by amino;

each R⁴ is independently selected from hydrogen, fluoro, chloro, methyl, methoxy, trifluoromethyl, cyano, nitro or —N(R⁹)₂;

R⁵, R⁵ᵃ, R⁶, R⁶ᵃ, R⁷, R⁷ᵃ, R⁸, and R⁸ᵃ are each independently selected from hydrogen or $C_1$-$C_3$alkyl;

or R⁵ and R⁵ᵃ together or R⁷ and R⁷ᵃ together are an oxo group, while the remaining R⁵, R⁵ᵃ, R⁶, R⁶ᵃ, R⁷, R⁷ᵃ, R⁸, and R⁸ᵃ are each independently selected from hydrogen or $C_1$-$C_3$alkyl;

each R¹¹ is independently selected from hydrogen, $C_1$-$C_6$alkyl, $C_3$-$C_6$cycloalkyl, aryl or aralkyl; and each R⁹ is independently selected from hydrogen or $C_1$-$C_6$alkyl.

Of this embodiment, a preferred embodiment of a compound of formula (I) is selected from the group consisting of the following:

5-[4-(2-Trifluoromethyl-benzoyl)-piperazin-1-yl]-pyridine-2-carboxylic acid (3-phenyl-propyl)-amide;

5-[4-(2-Trifluoromethyl-benzoyl)-piperazin-1-yl]-pyridine-2-carboxylic acid phenethyl-amide;

5-[4-(2-Trifluoromethylbenzoyl)piperazin-1-yl]pyridine-2-carboxylic acid [2-(4-fluoro-phenyl)ethyl]amide;

5-[4-(2-Trifluoromethyl-benzoyl)-piperazin-1-yl]-pyridine-2-carboxylic acid [3-(4-fluoro-phenyl)-propyl]-amide;

5-[4-(2-Trifluoromethyl-benzoyl)-piperazin-1-yl]-pyridine-2-carboxylic acid 4-trifluoromethyl-benzylamide;

5-[4-(2-Trifluoromethyl-benzoyl)-piperazin-1-yl]-pyridine-2-carboxylic acid [3-(4-trifluoromethyl-phenyl)-propyl]-amide;

5-[4-(2-Trifluoromethyl-benzoyl)-piperazin-1-yl]-pyridine-2-carboxylic acid [2-(4-trifluoromethyl-phenyl)-ethyl]-amide;

5-[4-(2-Trifluoromethyl-benzoyl)-piperazin-1-yl]-pyridine-2-carboxylic acid (3-methyl-butyl)-amide;

5-[4-(2-Trifluoromethyl-benzoyl)-piperazin-1-yl]-pyridine-2-carboxylic acid hexylamide;

5-[4-(2-Trifluoromethyl-benzoyl)-piperazin-1-yl]-pyridine-2-carboxylic acid pentylamide;

5-[4-(4-Fluoro-2-trifluoromethyl-benzoyl)-piperazin-1-yl]-pyridine-2-carboxylic acid (3-methyl-butyl)-amide;

5-[4-(5-Fluoro-2-trifluoromethyl-benzoyl)-piperazin-1-yl]-pyridine-2-carboxylic acid (3-methyl-butyl)-amide;

5-[4-(2-Trifluoromethylbenzoyl)piperazin-1-yl]pyridine-2-carboxylic acid (3-cyclohexyl-propyl)amide;

5-[4-(6-Trifluoromethyl-cyclohexa-1,3-dienecarbonyl)-piperazin-1-yl]-pyridine-2-carboxylic acid (2-cyclohexyl-ethyl)-amide;

5-[4-(2-Trifluoromethyl-benzoyl)-piperazin-1-yl]-pyridine-2-carboxylic acid cyclohexylmethyl-amide;

4-[2-({5-[4-(2-Trifluoromethyl-benzoyl)-piperazin-1-yl]-pyridine-2-carbonyl}-amino)-ethyl]-piperazine-1-carboxylic acid tert-butyl ester;

5-[4-(Naphthalene-1-carbonyl)-piperazin-1-yl]-pyridine-2-carboxylic acid (3-phenyl-propyl)-amide; and 5-[4-(Naphthalene-1-carbonyl)piperazin-1-yl]pyridine-2-carboxylic acid phenethylamide.

In another embodiment of the invention, the SCD-1 inhibitors are compounds of formula (I) as set forth above in the Summary of the Invention wherein:

x and y are each 1;

G and J each —C(R⁴)—;

L and M are each —N=;

W is —O—, —C(O)O—, —N(R¹)—, —S(O)ₜ— (where t is 0, 1 or 2), —N(R¹)S(O)₂—, —OC(O)— or —C(O)—;

V is —C(O)—, —C(S)—, —C(O)N(R¹)—, —C(O)O—, —S(O)₂—, —S(O)₂N(R¹)— or —C(R¹⁰)H—;

each R¹ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

R² is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

R³ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

each R⁴ is independently selected from hydrogen, fluoro, chloro, methyl, methoxy, trifluoromethyl, cyano, nitro or —N(R⁹)₂;

R⁵, R⁵ᵃ, R⁶, R⁶ᵃ, R⁷, R⁷ᵃ, R⁸ and R⁸ᵃ are each independently selected from hydrogen or $C_1$-$C_3$alkyl;

or R⁶ and R⁶ᵃ together, or R⁷ and R⁷ᵃ together, or R⁸ and R⁸ᵃ together, or R⁵ and R⁵ᵃ together are an oxo group, provided that when V is —C(O)—, R⁶ and R⁶ᵃ together or R⁸ and R⁸ᵃ together do not form an oxo group, while the remaining R⁶, R⁶ᵃ, R⁷, R⁷ᵃ, R⁸, R⁸ᵃ, R⁵ and R⁵ᵃ are each independently selected from hydrogen or $C_1$-$C_3$alkyl;

R¹⁰ is hydrogen or $C_1$-$C_3$alkyl; and each R⁹ is independently selected from hydrogen or $C_1$-$C_6$alkyl.

Of this embodiment, a preferred embodiment of a compound of formula (I) is selected from the group consisting of the following:

[4-(6-Phenethyloxy-pyridazin-3-yl)-piperazin-1-yl]-(2-trifluoromethyl-phenyl)-methanone;

{4-[6-(2-Cyclopropyl-ethoxy)-pyridazin-3-yl]-piperazin-1-yl}-(2-trifluoromethyl-phenyl)-methanone;

[4-(6-Phenethylsulfanyl-pyridazin-3-yl)-piperazin-1-yl]-(2-trifluoromethyl-phenyl)-methanone;

{4-[6-(2-Phenyl-ethanesulfinyl)-pyridazin-3-yl]-piperazin-1-yl}-(2-trifluoromethyl-phenyl)-methanone;

{4-[6-(2-Phenyl-ethanesulfonyl)-pyridazin-3-yl]-piperazin-1-yl}-(2-trifluoromethyl-phenyl)-methanone;

{4-[6-(3-Methyl-butylsulfanyl)-pyridazin-3-yl]-piperazin-1-yl}-(2-trifluoromethyl-phenyl)-methanone;

[4-(6-Phenethylamino-pyridazin-3-yl)-piperazin-1-yl]-(2-trifluoromethyl-phenyl)-methanone;

{4-[6-(Methyl-phenethyl-amino)-pyridazin-3-yl]-piperazin-1-yl}-(2-trifluoromethyl-phenyl)-methanone; and
Propane-1-sulfonic acid {6-[4-(2-trifluoromethyl-benzoyl)-piperazin-1-yl]-pyridazin-3-yl}-amide.

In another embodiment of the invention, the SCD-1 inhibitors are compounds of formula (I) as set forth above in the Summary of the Invention wherein:

x and y are each 1;
J and M are each independently selected from —N═ or —C($R^4$)═;
G and L are each —N═;
W is —N($R^1$)C(O)—, —C(O)N($R^1$)—, —OC(O)N($R^1$)—, —N($R^1$)C(O)N($R^1$)—, —O—, —N($R^1$)—, —S(O)$_t$— (where t is 0, 1 or 2), —N($R^1$)S(O)$_2$—, —S(O)$_2$N($R^1$)—, —C(O)—, —OS(O)$_2$N($R^1$)—, —OC(O)—, —C(O)O— or —N($R^1$)C(O)O—;
V is —C(O)—, —C(O)O—, —C(S)—, —C(O)N($R^1$)—, —S(O)$_2$—, —S(O)$_2$N($R^1$)— or —C($R^{10}$)H—;
each $R^1$ is independently selected from the group consisting of hydrogen, $C_1$-$C_2$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;
$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
each $R^4$ is independently selected from hydrogen, fluoro, chloro, methyl, methoxy, trifluoromethyl, cyano, nitro or —N($R^9$)$_2$;
each $R^5$, $R^{5a}$, $R^6$, $R^{6a}$, $R^7$, $R^{7a}$, $R^8$ and $R^{8a}$ is independently selected from hydrogen or $C_1$-$C_3$alkyl;
or $R^5$ and $R^{5a}$ together, or $R^6$ and $R^{6a}$ together, or $R^7$ and $R^{7a}$ together, or $R^8$ and $R^{8a}$ together are an oxo group, provided that when V is —C(O)—, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;
$R^{10}$ is hydrogen or $C_1$-$C_3$alkyl; and
each $R^9$ is independently selected from hydrogen or $C_1$-$C_6$alkyl.

Of this embodiment, a preferred embodiment of a compound of formula (I) is selected from the group consisting of the following:

5-[4-(2-Trifluoromethyl-benzoyl)-piperazin-1-yl]-pyrimidine-2-carboxylic acid phenethyl-amide;
5-[4-(2-Trifluoromethyl-benzoyl)-piperazin-1-yl]-pyrimidine-2-carboxylic acid (3-phenyl-propyl)-amide;
5-[4-(2-Trifluoromethyl-benzoyl)-piperazin-1-yl]-pyrimidine-2-carboxylic acid benzylamide; and
5-[4-(2-Trifluoromethyl-benzoyl)-piperazin-1-yl]-pyrimidine-2-carboxylic acid hexylamide.

In another embodiment of the invention, the SCD-1 inhibitors are compounds of formula (I) as set forth above in the Summary of the Invention wherein:

x and y are each 1;
J and L are each —N═;
G and M are each —C($R^4$)═;
W is —N($R^1$)C(O)—, —C(O)N($R^1$)— or —OC(O)N($R^1$)—;
V is —C(O)—;
each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{11}$)$_2$, —OC(O)$R^{11}$, —C(O)O$R^{11}$, —S(O)$_2$N($R^{11}$)$_2$, cycloalkyl, heterocyclyl, heteroaryl and heteroarylcycloalkyl, provided that $R^3$ is not phenyl substituted with optionally substituted thienyl;
each $R^4$ is independently selected from hydrogen, fluoro, chloro, methyl, methoxy, trifluoromethyl, cyano, nitro or —N($R^9$)$_2$;
each $R^5$, $R^{5a}$, $R^6$, $R^{6a}$, $R^7$, $R^{7a}$, $R^8$ and $R^{8a}$ is independently selected from hydrogen or $C_1$-$C_3$alkyl;
or $R^5$ and $R^{5a}$ together or $R^7$ and $R^{7a}$ together form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;
each $R^9$ is independently selected from hydrogen or $C_1$-$C_6$alkyl; and
each $R^{11}$ is independently selected from hydrogen, $C_1$-$C_6$alkyl, $C_3$-$C_6$cycloalkyl, aryl or aralkyl.

Of this embodiment, a preferred embodiment of a compound of formula (I) is selected from the group consisting of the following:

4-(2-Trifluoromethyl-benzoyl)-3,4,5,6-tetrahydro-2H-[1,2']bipyrazinyl-5'-carboxylic acid (3-methyl-butyl)-amide;
4-(2-Trifluoromethyl-benzoyl)-3,4,5,6-tetrahydro-2H-[1,2']bipyrazinyl-5'-carboxylic acid (2-phenoxy-ethyl)-amide;
4-(2-Trifluoromethyl-benzoyl)-3,4,5,6-tetrahydro-2H-[1,2']bipyrazinyl-5'-carboxylic acid pentylamide;
4-(2-Trifluoromethyl-benzoyl)-3,4,5,6-tetrahydro-2H-[1,2']bipyrazinyl-5'-carboxylic acid phenethyl-amide;
4-(2-Trifluoromethyl-benzoyl)-3,4,5,6-tetrahydro-2H-[1,2']bipyrazinyl-5'-carboxylic acid (3-phenyl-propyl)-amide;
4-(2-Trifluoromethyl-benzoyl)-3,4,5,6-tetrahydro-2H-[1,2']bipyrazinyl-5'-carboxylic acid [2-(4-fluoro-phenyl)-ethyl]-amide;
4-(2-Trifluoromethyl-benzoyl)-3,4,5,6-tetrahydro-2H-[1,2']bipyrazinyl-5'-carboxylic acid [3-(4-fluoro-phenyl)-propyl]-amide; and
4-(2-Trifluoromethyl-benzoyl)-3,4,5,6-tetrahydro-2H-[1,2']bipyrazinyl-5'-carboxylic acid [3-(4-fluoro-phenyl)-propyl]-amide.

In another embodiment of the invention, the SCD-1 inhibitors are compounds of formula (I) as set forth above in the Summary of the Invention wherein:

x and y are each 1;
J and M are each —N═;
G and L are each —C($R^4$)═;
W is —N($R^1$)C(O)—, —C(O)N($R^1$)— or —OC(O)N($R^1$)—;
V is —C(O)—;
each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

R² is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

R³ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N(R¹¹)₂, —OC(O)R¹¹, —C(O)OR¹¹, —S(O)₂N(R¹¹)₂, cycloalkyl, heterocyclyl, heteroaryl and heteroarylcycloalkyl, provided that R³ is not phenyl substituted with optionally substituted thienyl;

each R⁴ is independently selected from hydrogen, fluoro, chloro, methyl, methoxy, trifluoromethyl, cyano, nitro or —N(R⁹)₂;

each R⁵, R⁵ᵃ, R⁶, R⁶ᵃ, R⁷, R⁷ᵃ, R⁸ and R⁸ᵃ is independently selected from hydrogen or $C_1$-$C_3$alkyl;

or R⁵ and R⁵ᵃ together or R⁷ and R⁷ᵃ together form an oxo group, while the remaining R⁵, R⁵ᵃ, R⁶, R⁶ᵃ, R⁷, R⁷ᵃ, R⁸ and R⁸ᵃ are each independently selected from hydrogen or $C_1$-$C_3$alkyl;

each R⁹ is independently selected from hydrogen or $C_1$-$C_6$alkyl; and each R¹¹ is independently selected from hydrogen, $C_1$-$C_6$alkyl, $C_3$-$C_6$cycloalkyl, aryl or aralkyl.

Of this embodiment, a preferred embodiment of a compound of formula (I) is selected from the group consisting of the following:

4-trifluoromethyl-2-[4-(2-trifluoromethylbenzoyl)piperazin-1-yl]-pyrimidine-5-carboxylic acid (3-methylbutyl) amide; and 2-[4-(2-Trifluoromethylbenzoyl)piperazin-1-yl]pyrimidine-5-carboxylic acid (3-methylbutyl)amide.

In another embodiment of the invention, the SCD-1 inhibitors are compounds of formula (I) as set forth above in the Summary of the Invention wherein:

x and y are each 1;

W is —N(R¹)C(O)N(R¹)—, —O—, —N(R¹)—, —S(O)$_t$— (where t is 0, 1 or 2), —N(R¹)S(O)₂—, —S(O)₂N(R¹)—, —C(O)O— or —N(R¹)C(O)O—;

V is —C(O)—, —C(O)O—, —C(S)—, —C(O)N(R¹)—, —S(O)₂— or —S(O)₂N(R¹)—;

G, J, L and M are each independently selected from —N= or —C(R⁴)=; provided that at least two of G, J, L and M are —N=, and provided that when G and J are both —C(R⁴)=, L and M can not both be —N=, and when L and M are both —C(R⁴)=, G and J can not both be —N=;

each R¹ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

R² is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

R³ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

each R⁴ is independently selected from hydrogen, fluoro, chloro, methyl, methoxy, trifluoromethyl, cyano, nitro or —N(R⁹)₂;

each R⁵, R⁵ᵃ, R⁶, R⁶ᵃ, R⁷, R⁷ᵃ, R⁸ and R⁸ᵃ is independently selected from hydrogen or $C_1$-$C_3$alkyl;

or R⁵ and R⁵ᵃ together, or R⁶ and R⁶ᵃ together, or R⁷ and R⁷ᵃ together, or R⁸ and R⁸ᵃ together are an oxo group, provided that when V is —C(O)—, R⁶ and R⁶ᵃ together or R⁸ and R⁸ᵃ together do not form an oxo group, while the remaining R⁵, R⁵ᵃ, R⁶, R⁶ᵃ, R⁷, R⁷ᵃ, R⁸ and R⁸ᵃ are each independently selected from hydrogen or $C_1$-$C_3$alkyl; and each R⁹ is independently selected from hydrogen or $C_1$-$C_6$alkyl.

The compounds disclosed above in the embodiment section and the compounds specifically named in the embodiment section were or can be made by the methods disclosed herein, or similar methods thereto.

Preparation of the Compounds of the Invention

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1999), 3rd Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following Reaction Schemes illustrate methods to make compounds of this invention. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry Reactions, Mechanisms, and Structure, 5th edition (Wiley, December 2000)) or prepared as described in this invention.

Unless specifically indicated otherwise in the following descriptions, x, y, W, V, R¹, R², R³, R⁴, R⁵, R⁵ᵃ, R⁶, R⁶ᵃ, R⁷, R⁷ᵃ, R⁸, R⁸ᵃ, R⁹ and R¹⁰ are as defined above in the Summary of the Invention for compounds of formula (I). It is understood that compounds of formula (I) not specifically disclosed in the following reaction schemes can be prepared in methods similar to those described below.

The compounds that are the SCD-1 inhibitors disclosed herein, can be prepared by the following methods or the methods disclosed in PCT Application Nos PCT/US2004/024657, PCT/US2004/024542, PCT/US2004/024548, PCT/

US2004/024541, PCT/US2004/021792, and PCT/US2004/024658, the disclosures of which are incorporated in full in their entirety by reference.

In general, the compounds of formula (I) of this invention where G and J are C($R^4$), L and M are N and W is —N($R^1$)C(O)— can be synthesized following the general procedure as described in Reaction Scheme 1.

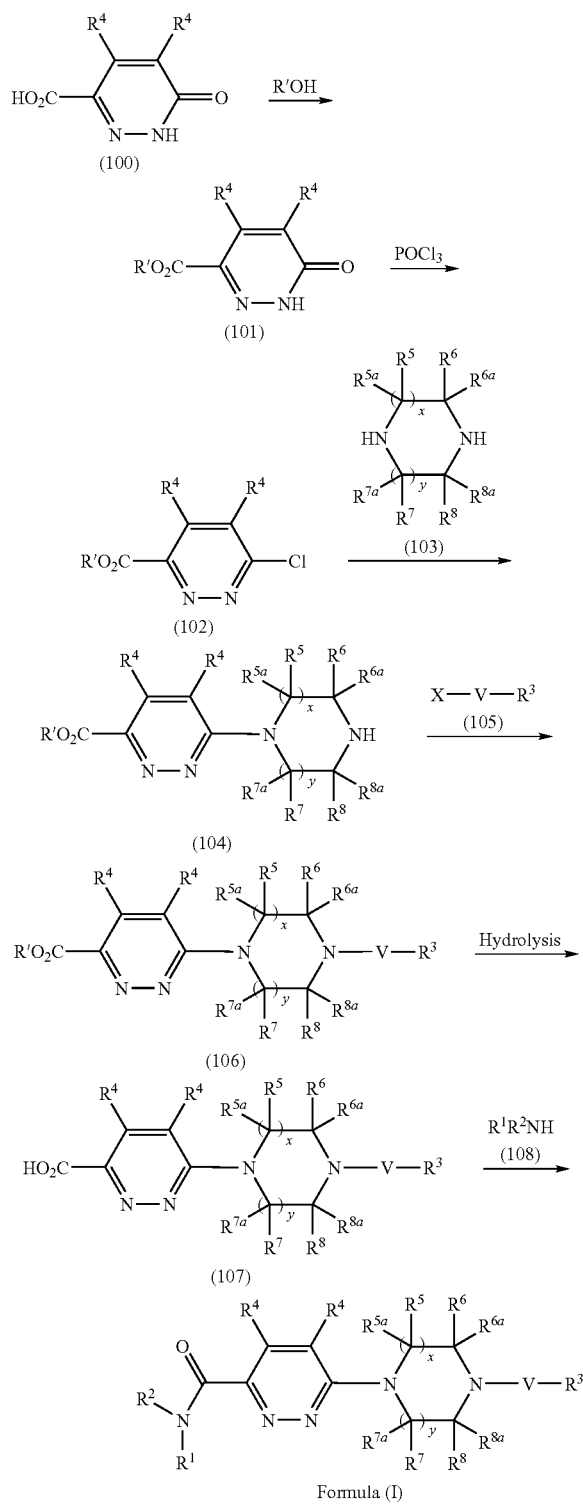

The starting materials for the above reaction scheme are commercially available or can be prepared according to methods known to one skilled in the art or by methods disclosed herein. In general, the compounds of the invention are prepared in the above reaction scheme as follows:

Compound 101. A carboxylic acid of formula (100) can easily be converted to an ester of formula (101) following a standard procedure in the literature known to one skilled in the art.

Compound 102. A mixture of a compound of formula (101) obtained above and phosphorous oxychloride is carefully heated to reflux for 2-8 hours. The reaction mixture is then cooled and excess phosphorous oxychloride is removed. The residue is then poured into ice water. The precipitate obtained is collected by filtration, washed with saturated $NaHCO_3$ and water, and then dried to yield the compound of formula (102).

Compound 104. A mixture of the compound of formula (102) (1 equivalent) and the compound of formula (103) (3 equivalent) in a solvent such as N,N-dimethylformamide or acetonitrile but not limited to is refluxed for 1-4 hours. The solvent is then removed in vacuo. The residue is dissolved in a solvent such as dichloromethane or ethyl acetate but not limited to. The resulting solution is washed with water, brine, and then dried. The organic phase was concentrated in vacuo to afford the compound of formula (104).

Compound 106. To a stirred solution of the compound of formula (104) (1 equivalent) in a solvent such as dichloromethane, toluene or THF but not limited to is added the solution of a chloride or bromide of formula (105) (1 equivalent) in the presence of a base such as triethylamine or Hunigs base but not limited to at 0° C. The resulting mixture is stirred at ambient temperature for 6-18 hours and then quenched with water. The organic phase is washed with water, brine, dried and then concentrated in vacuo to afford the product of formula (106) which is further purified by chromatography or crystallization.

Compound 107. A solution of a compound of formula (106) obtained above is dissolved in an adequate solvent and the ester is converted to a carboxylic acid under a standard condition known to one skilled in the art to obtain the carboxylic acid of formula (107).

Compound of formula (I). To a solution of a compound of formula (107) (1 equivalent) in a solvent such as dichloromethane, toluene or THF but not limited to is added a base such as triethylamine or Hunigs base but not limited to (2.5 equivalent), followed by the addition of a coupling agent such as N-(3-dimethylaminopropyl)-N'-ethylcarbodiimide (1.1 equivalent). The resulting mixture is stirred for 15 minutes to an hour and an amine of formula (108) (1.1 equivalent) is added. The mixture is stirred for 8-24 hours, then washed with water, dried and concentrated in vacuo. Purification by column chromatography or crystallization from a suitable solvent affords the compound of formula (I).

Alternatively, compounds of formula (I) of this invention where G and J are C($R^4$), L and M are N and W is —N($R^1$)C(O)— can be synthesized following the general procedure as described in Reaction Scheme 2.

REACTION SCHEME 2

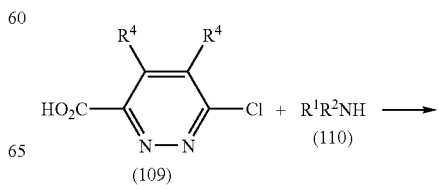

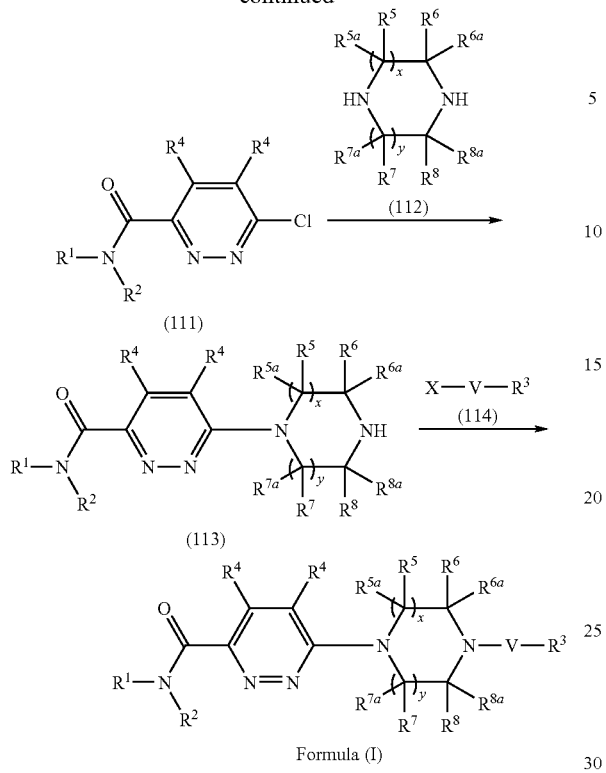

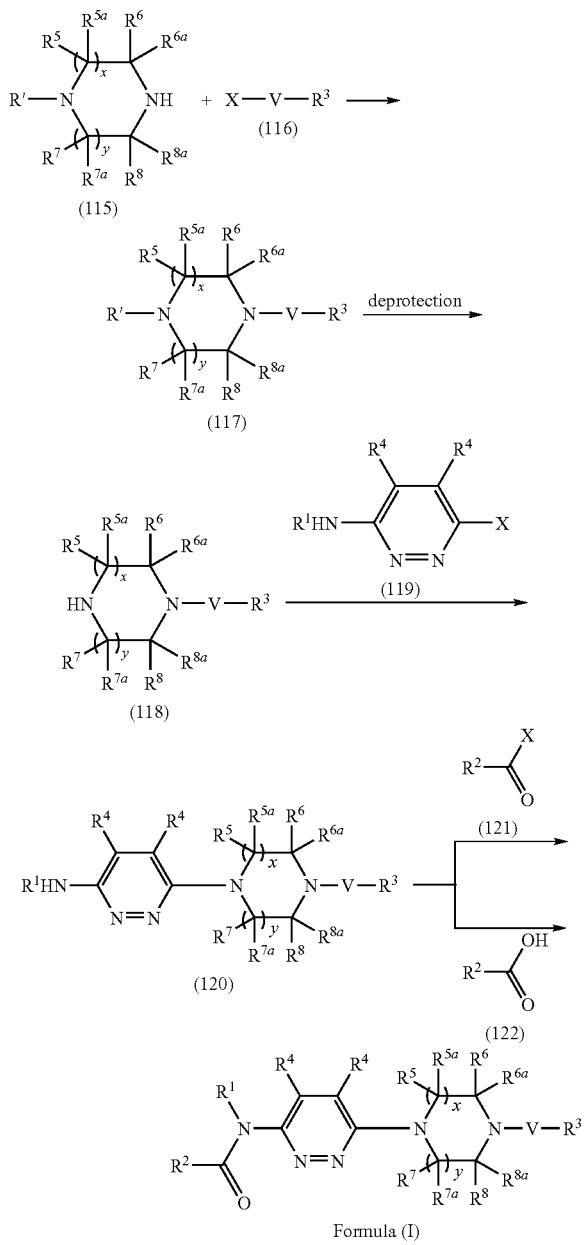

The starting materials for the above reaction scheme are commercially available or can be prepared according to methods known to one skilled in the art or by methods disclosed herein. In general, the compounds of the invention are prepared in the above reaction scheme as follows:

Compound 111. To a solution of substituted 6-chloropyridazinyl-3-carboxylic acid of formula (109) (1 equivalent) in a solvent such as dichloromethane, toluene or THF but not limited to is added a base such as triethylamine or Hunigs base but not limited to (2.5 equivalent), followed by the addition of a coupling agent such as N-(3-dimethylaminopropyl)-N'-ethylcarbodiimide (1.1 equivalent). The resulting mixture is stirred for 15 minutes to an hour and an amine of formula (110) (1.1 equivalent) is added. The mixture is stirred for 8-24 hours, then washed with water, dried and concentrated in vacuo. Purification by column chromatography or crystallization from a suitable solvent affords the compound of formula (111).

Compound 113. A mixture of the compound of formula (111) (1 equivalent) and the compound of formula (112) (3 equivalent) in a solvent such as N,N-dimethylformamide or acetonitrile but not limited to is refluxed for 1-4 hours. The solvent is then removed in vacuo. The residue is dissolved in a solvent such as dichloromethane or ethyl acetate but not limited to. The resulting solution is washed with water, brine, and then dried. The organic phase was concentrated in vacuo to afford the compound of formula (113).

Compound of Formula (I). To a stirred solution of the compound of formula (113) (1 equivalent) in a solvent such as dichloromethane, toluene or THF but not limited to is added the solution of a chloride or bromide of formula (114) (1 equivalent) in the presence of a base such as triethylamine or Hunigs base but not limited to at 0° C. The resulting mixture is stirred at ambient temperature for 6-18 hours and then quenched with water. The organic phase is washed with water, brine, dried and then concentrated in vacuo to afford the compound of formula (I) which is further purified by chromatography or crystallization.

Alternatively, compounds of formula (I) of this invention where G and J are C(R$^4$), L and M are N and W is —C(O)N(R$^1$)— can be synthesized following the general procedure as described in Reaction Scheme 3.

The starting materials for the above reaction scheme are commercially available or can be prepared according to methods known to one skilled in the art or by methods disclosed herein. In general, the compounds of the invention are prepared in the above reaction scheme as follows:

Compound 117. To a stirred solution of the amine of formula (115) (1 equivalent) in a solvent such as dichloromethane or toluene but not limited to is added the solution of a chloride or bromide of formula (116) (1 equivalent) in a solvent such as dichloromethane or toluene but not limited to in the presence of a base such as triethylamine or Hunigs base but not limited to. The resulting mixture is stirred at ambient temperature for an adequate time period and then quenched with water. The organic phase is washed with water, brine, dried and then concentrated in vacuo to afford the product of formula (117).

Compound 118. A solution of compound of formula (117) obtained above is dissolved in an adequate solvent and the protecting group R' is removed under standard deprotection conditions such as hydrolysis or hydrogenation to obtain the amine of formula (118).

Compound 120. A mixture of a chloropyridazine of formula (119) (1 equivalent) and the amine of formula (118) obtained above (1.5 equivalent) in an adequate solvent is heated at reflux for 4-24 hours. To the reaction mixture is added a basic solution such as NaOH solution. The aqueous layer is extracted by an organic solvent such as dichloromethane or ethyl acetate. The combined organic phase is dried, then evaporated to dryness. The crude compound is purified by column chromatography or crystallization to afford the compound of formula (120).

Compound of Formula (I).

Method A. To a stirred solution of compound of formula (120) (1 equivalent) in a solvent such as dichloromethane, acetonitrile or toluene is added the solution of a compound of formula (121) (1 equivalent) in the presence of a base such as triethylamine or Hunigs base (1 equivalent) at 0° C. The resulting mixture is stirred at ambient temperature for 8-24 hours and then quenched with water. The organic phase is washed with water, brine, dried and then concentrated in vacuo. Further purification by column chromatography or crystallization from a suitable solvent affords the compound of formula (I).

Method B. To a solution of a carboxylic acid of formula (122) (1 equivalent) in a solvent such as dichloromethane, toluene or THF is added a base such as triethylamine or Hunigs base (2.5 equivalent), followed by the addition of a coupling agent such as (3-dimethylaminopropyl)ethyl carbodiimide (1.1 equivalent). The resulting mixture is stirred for 15 minutes to an hour and an amine of formula (120) (1.1 equivalent) is added. The mixture is stirred at ambient temperature for 8-24 hours, then washed with water, dried and concentrated in vacuo. Purification by column chromatography or crystallization from a suitable solvent affords the compound of formula (I).

Alternatively, compounds of formula (I) of this invention where G and J are $C(R^4)$, L and M are N and W is —$N(R^1)$ $C(O)N(R^1)$— can be synthesized following the general procedure as described in Reaction Scheme 4.

REACTION SCHEME 4

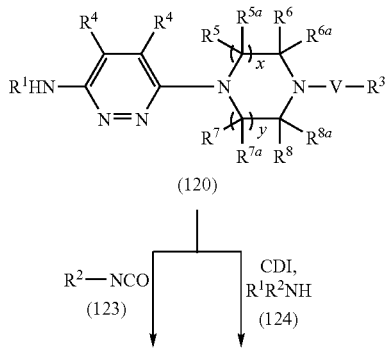

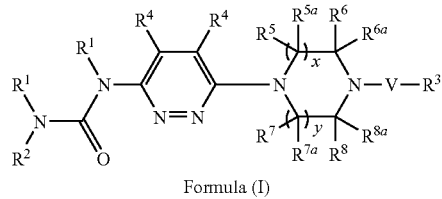

Formula (I)

The starting materials for the above reaction scheme are commercially available or can be prepared according to methods known to one skilled in the art or by methods disclosed herein. In general, the compounds of the invention are prepared in the above reaction scheme as follows:

Compound of Formula (I):

Method C. To a stirred solution of the compound of formula of (120) (1 equivalent) in an anhydrous solvent such as DMF but not limited to is added an isocyanate of formula (123) (3 equivalent), and the mixture is then heated to 60-80° C. for 4-24 hours. The mixture is concentrated in vacuo. Purification of the crude product by column chromatography or crystallization from a suitable solvent affords the compound of Formula (I).

Method D. A compound of formula (120) (1 equivalent) is slowly added to an ice cold solution of 1,1'-carbonyldiimidazole (1.5 to 2.5 equivalent) in an anhydrous solvent such as dichloromethane. The temperature is then raised to ambient temperature and the reaction mixture is stirred for another 2-8 hours. An amine of formula (124) (1 equivalent) is then added to the reaction mixture which is stirred at ambient temperature overnight under nitrogen atmosphere. The reaction mixture is then washed with saturated sodium bicarbonate and brine solution, concentrated and purified by flash column chromatography to afford the compound of formula (I)

Alternatively, the compounds of formula (I) of the invention where G, J and L are $C(R^4)$, M is N, W is —$C(O)N(R^1)$— and V is —$C(O)$—, —$S(O)_2$— or —$C(R^{11})H$— can be synthesized following the general procedure as described in Reaction Scheme 5.

REACTION SCHEME 5

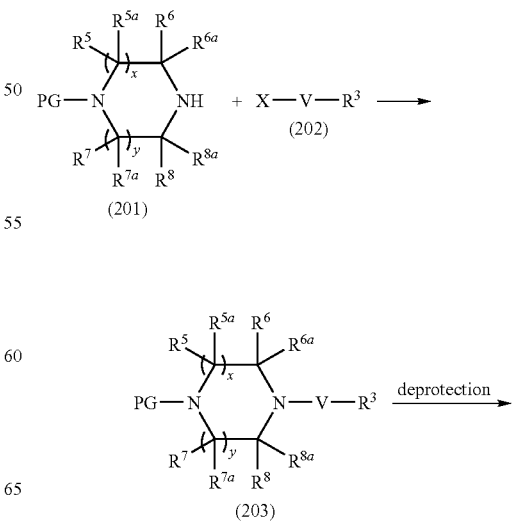

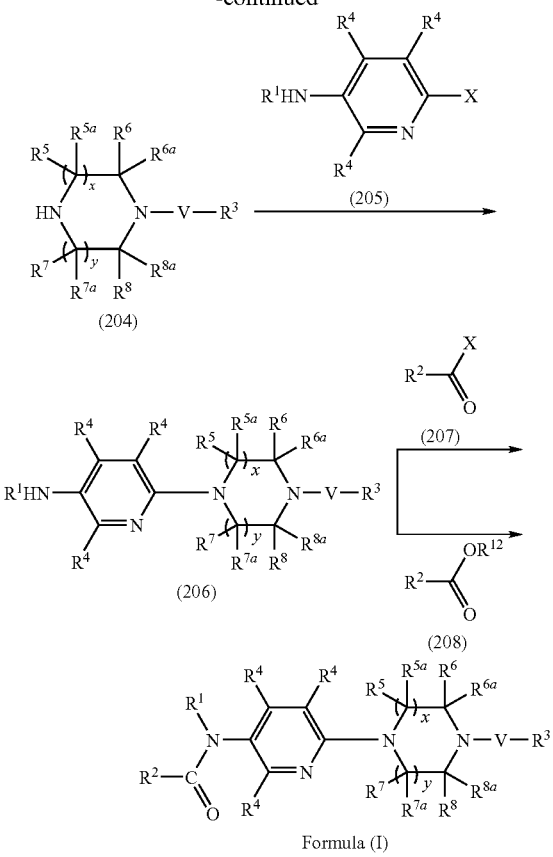

Formula (I)

The starting materials for the above reaction scheme are commercially available or can be prepared according to methods known to one skilled in the art or by methods disclosed herein. In general, the compounds of the invention are prepared in the above reaction scheme as follows:

Compound 203. To a stirred solution of the amine of formula (201) (1 equivalent) in a solvent such as dichloromethane or toluene is added the solution of a compound of formula (202) (1 equivalent) in a solvent such as dichloromethane or toluene in the presence of a base such as triethylamine or Hunigs base. The resulting mixture is stirred at ambient temperature for an adequate time period and then quenched with water. The organic phase is washed with $H_2O$, brine, dried over and then concentrated in vacuo to afford the product of formula (203).

Compound 204. A solution of compound of formula of (203) obtained above is dissolved in an adequate solvent and the protecting group PG is removed under standard deprotection conditions such as hydrolysis or hydrogenation to obtain the amine of formula (204).

Compound 206. The mixture of a pyridine compound of formula (205) (1 equivalent) and the compound of formula (204) obtained above (1.5 equivalent) in an adequate solvent is heated at reflux for 4-24 hours. To the reaction mixture is added a basic solution such as NaOH solution. The aqueous layer is extracted by an organic solvent such as dichloromethane or ethyl acetate. The combined organic phase is dried, then evaporated to dryness. The crude compound is purified by column chromatography or crystallization to afford the compound of formula (206).

Compound of formula (I):

Method A: To a stirred solution of compound of formula (206) (1 equivalent) in a solvent such as dichloromethane, acetonitrile or toluene is added the solution of a compound of formula (207) (1 equivalent) in the presence of a base such as triethylamine or Hunigs base (1 equivalent) at 0° C. The resulting mixture is stirred at ambient temperature for 8-24 hours and then quenched with water. The organic phase is washed with $H_2O$, brine, dried and then concentrated in vacuo to afford the compound of formula (I).

Method B: To a solution of the compound of formula (208) (1 equivalent) ($R^{12}$=H) in a solvent such as dichloromethane, toluene or THF is added a base such as triethylamine or Hunigs base (2.5 equivalent), followed by the addition of a coupling agent such as (3-dimethylaminopropyl) ethyl carbodiimide (1.1 equivalent). The resulting mixture is stirred for 15 minutes to an hour and an amine of formula (206) (1.1 equivalent) is added. The mixture is stirred at ambient temperature for 8-24 hours, then washed with water, dried and concentrated in vacuo. Purification by column chromatography or crystallization from a suitable solvent affords the compound of formula (I).

Alternatively, the compounds of formula (I) of the invention where G, J and L are $C(R^4)$, M is N, W is —NHC(O)N($R^1$)— and V is —C(O)—, —S(O)$_2$— or —C($R^{11}$)H— can be synthesized following the general procedure as described in Reaction Scheme 6.

REACTION SCHEME 6

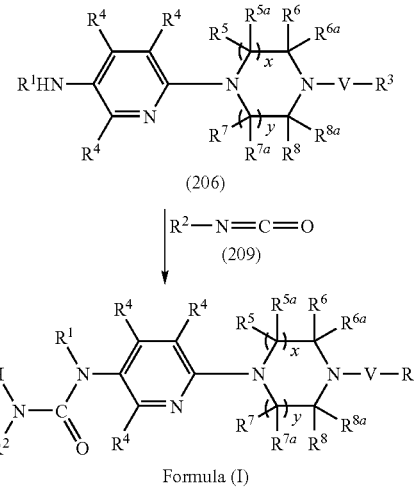

Formula (I)

The starting materials for the above reaction scheme are commercially available or can be prepared according to methods known to one skilled in the art or by methods disclosed herein. In general, the compounds of the invention are prepared in the above reaction scheme as follows:

Compound of formula (I). To a stirred solution of the compound of formula (206) (1 equivalent) in an anhydrous solvent such as dimethylformamide is added an isocyanate of formula (209) (3 equivalent), and the mixture is then heated to 60-80° C. for 4-24 hours. The mixture is concentrated in vacuo. Purification of the crude product by column chromatography or crystallization from a suitable solvent affords the compound of formula (I)

Alternatively, the compounds of formula (I) of the invention where G, J and L are $C(R^4)$, M is N, W is —S(O)$_2$N ($R^1$)— and V is —C(O)—, —S(O)$_2$— or —C($R^{11}$)H— can be synthesized following the general procedure as described in Reaction Scheme 7.

REACTION SCHEME 7

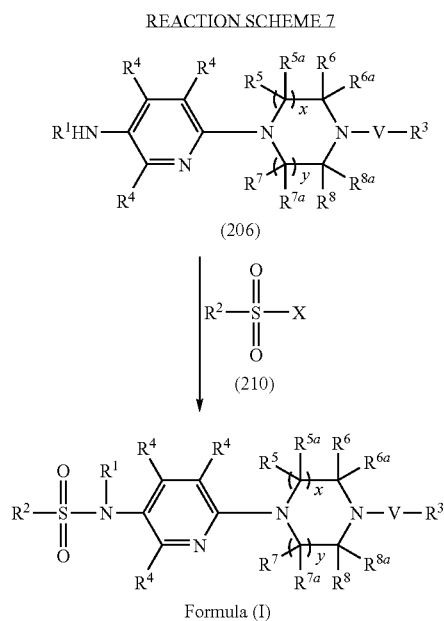

Formula (I)

The starting materials for the above reaction scheme are commercially available or can be prepared according to methods known to one skilled in the art or by methods disclosed herein. In general, the compounds of the invention are prepared in the above reaction scheme as follows:

Compound of formula (I): To a solution of compound of formula (206) (1 equivalent) in a solvent such as dichloromethane, acetonitrile or toluene is added slowly a compound of formula (210) (1 equivalent) at 0° C. The resulting mixture is stirred at ambient temperature for 8-24 hours and then quenched with water. After removal of solvent, the product was purified by chromatography to afford the compound of formula (I).

Alternatively, the intermediate compound of formula (206) can be prepared following the general procedure as described in Reaction Scheme 8.

REACTION SCHEME 8

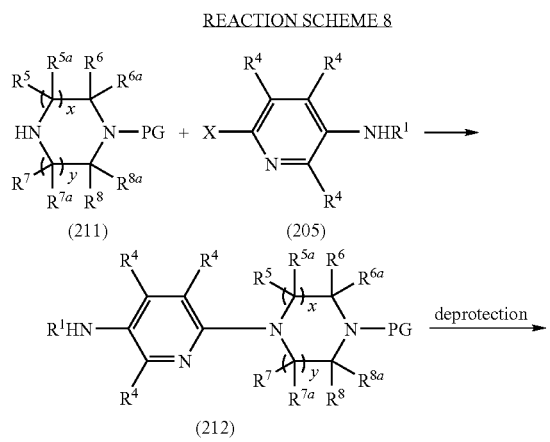

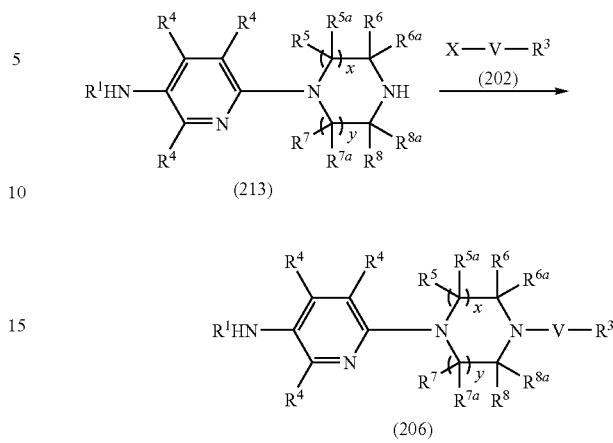

Compound 212. The mixture of a pyridine compound of formula (205) (1 equivalent) and the compound of formula (211) (1.5 equivalent) in an adequate solvent is heated at reflux for 4-24 hours. To the reaction mixture is added a basic solution such as NaOH solution. The aqueous layer is extracted by an organic solvent such as dichloromethane or ethyl acetate. The combined organic phase is dried, then evaporated to dryness. The crude compound is purified by column chromatography or crystallization to afford the compound of formula (212).

Compound 213. A solution of compound of formula of (212) obtained above is dissolved in an adequate solvent and the protecting group PG is removed under standard deprotection conditions such as hydrolysis or hydrogenation to obtain the amine of formula (213).

Compound 206. To a stirred solution of the amine of formula (213) (1 equivalent) in a solvent such as dichloromethane or toluene is added the solution of a compound of formula (202) (1 equivalent) in a solvent such as dichloromethane or toluene in the presence of a base such as triethylamine or Hunigs base. The resulting mixture is stirred at ambient temperature for an adequate time period and then quenched with water. The organic phase is washed with H$_2$O, brine, dried over and then concentrated in vacuo to afford the product of formula (I).

Alternatively, the compounds of formula (I) of the invention where G, J and L are C($R^4$), M is N, W is —C(O)NH— and V is —C(O)—, —S(O)$_2$— or —C($R^{11}$)H— can be synthesized following the general procedure as described in Reaction Scheme 9.

REACTION SCHEME 9

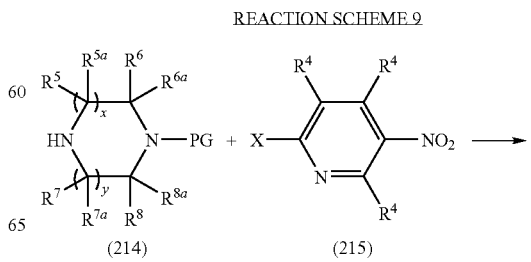

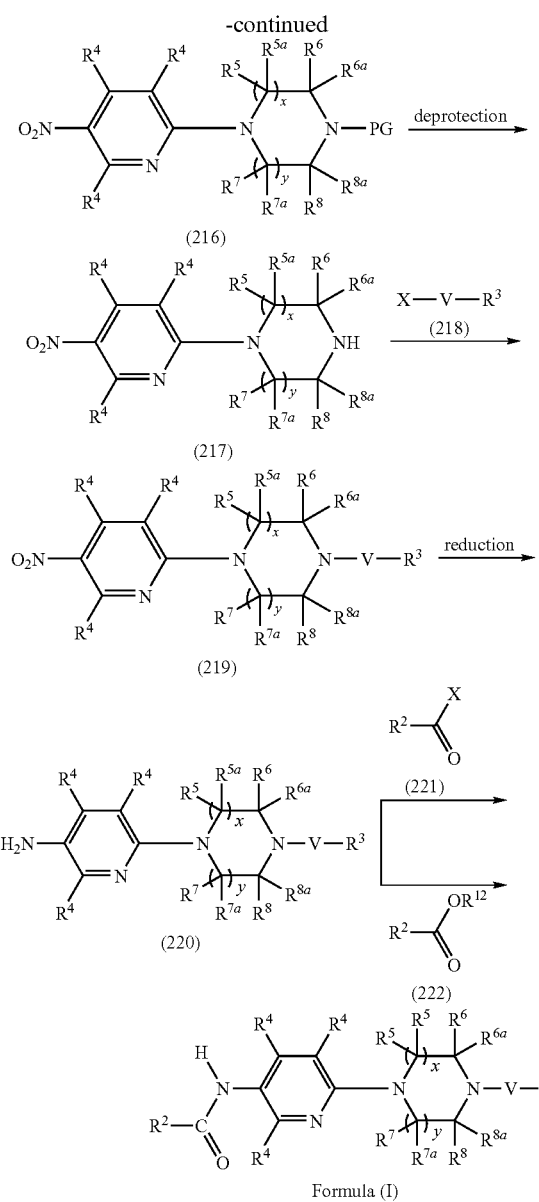

Compound 219. The mixture of a pyridine compound of formula (217) (1 equivalent) and the compound of formula (218) (1.5 equivalent) in an adequate solvent is heated at reflux for 4-24 hours. To the reaction mixture is added a basic solution such as NaOH solution. The aqueous layer is extracted by an organic solvent such as dichloromethane or ethyl acetate. The combined organic phase is dried, then evaporated to dryness. The crude compound is purified by column chromatography or crystallization to afford the compound of formula (219).

Compound 220. The nitro compound of formula (219) can be reduced to the corresponding amine compound of formula (220) using a standard hydrogenation process known to one skilled in the art.

Compound of formula (I):

Method A: To a stirred solution of compound of formula (220) (1 equivalent) in a solvent such as dichloromethane, acetonitrile or toluene is added the solution of a compound of formula (221) (1 equivalent) in the presence of a base such as triethylamine or Hunigs base (1 equivalent) at 0° C. The resulting mixture is stirred at ambient temperature for 8-24 hours and then quenched with water. The organic phase is washed with $H_2O$, brine, dried and then concentrated in vacuo to afford the compound of formula (I).

Method B: To a solution of the compound of formula (222) (1 equivalent) in a solvent such as dichloromethane, toluene or THF is added a base such as triethylamine or Hunigs base (2.5 equivalent), followed by the addition of a coupling agent such as (3-dimethylaminopropyl)-ethyl carbodiimide (1.1 equivalent). The resulting mixture is stirred for 15 minutes to an hour and an amine of formula (220) (1.1 equivalent) is added. The mixture is stirred at ambient temperature for 8-24 hours, then washed with water, dried and concentrated in vacuo. Purification by column chromatography or crystallization from a suitable solvent affords the compound of formula (I).

Alternatively, the compounds of formula (I) of the invention where G, J and L are $C(R^4)$, M is N, W is —NHC(O)NH— and V is —C(O)—, —$S(O)_2$— or —$C(R^{11})H$— can be synthesized following the general procedure as described in Reaction Scheme 10.

REACTION SCHEME 10

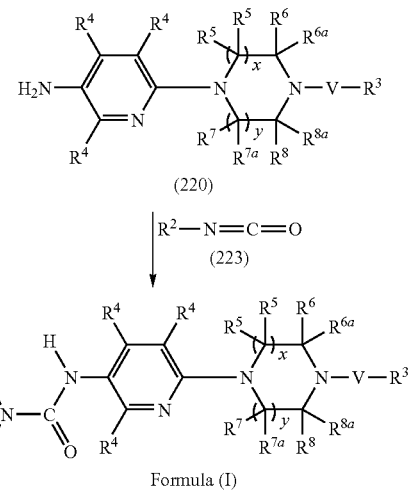

The starting materials for the above reaction scheme are commercially available or can be prepared according to methods known to one skilled in the art or by methods disclosed herein. In general, the compounds of the invention are prepared in the above reaction scheme as follows:

Compound 216. To a stirred solution of the amine of formula (214) (1 equivalent) in a solvent such as dichloromethane or toluene is added the solution of a compound of formula (215) (1 equivalent) in a solvent such as dichloromethane or toluene in the presence of a base such as triethylamine or Hunigs base. The resulting mixture is stirred at ambient temperature for an adequate time period and then quenched with water. The organic phase is washed with $H_2O$, brine, dried over and then concentrated in vacuo to afford the product of formula (216).

Compound 217. A solution of compound of formula of (216) obtained above is dissolved in an adequate solvent and the protecting group PG is removed under standard deprotection conditions such as hydrolysis or hydrogenation to obtain the amine of formula (217).

ods known to one skilled in the art or by methods disclosed herein. In general, the compounds of the invention are prepared in the above reaction scheme as follows:

Compound of formula (I). To a stirred solution of the compound of formula (220) (1 equivalent) in an anhydrous solvent such as dimethylformamide is added an isocyanate of formula (223) (3 equivalent), and the mixture is then heated to 60-80° C. for 4-24 hours. The mixture is concentrated in vacuum. Purification of the crude product by column chromatography or crystallization from a suitable solvent affords the compound of formula (I).

Alternatively, the compounds of formula (I) of the invention where G, J and L are C($R^4$), M is N, W is —S(O)$_2$NH— and V is —C(O)—, —S(O)$_2$— or —C($R^{11}$)H— can be synthesized following the general procedure as described in Reaction Scheme 11.

REACTION SCHEME 11

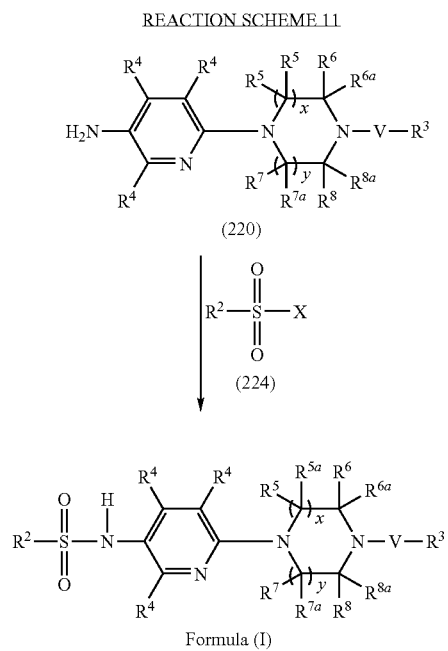

Formula (I)

The starting materials for the above reaction scheme are commercially available or can be prepared according to methods known to one skilled in the art or by methods disclosed herein. In general, the compounds of the invention are prepared in the above reaction scheme as follows:

Compound of formula (I): To a solution of compound of formula (220) (1 equivalent) in a solvent such as dichloromethane, acetonitrile or toluene is added slowly the solution of compound of formula (224) (1 equivalent) at 0° C. The resulting mixture is stirred at ambient temperature for 8-24 hours and then quenched with water. After removal of solvent, the product was purified by chromatography to afford the compound of formula (I).

Alternatively, the compounds of formula (I) of the invention where G, J and L are C($R^4$), M is N, W is —NH— and V is —C(O)—, —S(O)$_2$— or —C($R^{11}$)H— can be synthesized following the general procedure as described in Reaction Scheme 12.

REACTION SCHEME 12

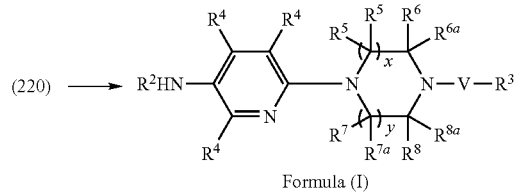

Formula (I)

Reaction of amine (220) with an appropriate aldehyde in the presence of a reducing agent such as, but not limited to, sodium borohydride in a solvent such as, but not limited, ethanol produces compound of formula (I).

Alternatively, the compounds of formula (I) of the invention where G, J and L are C($R^4$), M is N, W is —O— and V is —C(O)—, —S(O)$_2$— or —C($R^{11}$)H— can be synthesized following the general procedure as described in Reaction Scheme 13.

REACTION SCHEME 13

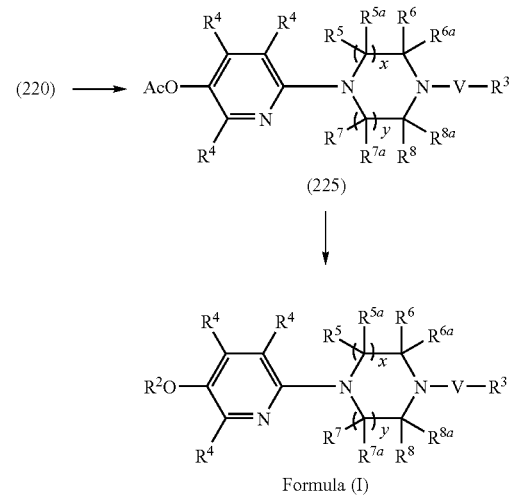

Formula (I)

Reaction of amine (220) with sodium nitrite in the presence of a Lewis acid such as, but not limited to, boron trifluoride diethyl etherate in a solvent such as, but not limited to, N,N-dimethylformamide, generates a diazonium intermediate that can be converted into the acetoxy compound (225) by quenching the above reaction mixture with acetic anhydride. Hydrolysis of the ester compound (225) in the presence of a base such as, but not limited to, sodium hydroxide, produces a hydroxy intermediate that can be converted into the desired product of formula (I) (W=—O—) with an appropriate $R^2$X in the presence of a base such as, but not limited to, sodium hydride in a solvent such as, but not limited to, tetrahydrofuran or N,N-dimethylformamide.

Alternatively, the compounds of formula (I) of the invention where G, J and L are C($R^4$), M is N, W is —S(O)$_t$— (where t is 0, 1 or 2) and V is —C(O)—, —S(O)$_2$— or —C($R^{11}$)H— can be synthesized following the general procedure as described in Reaction Scheme 14.

REACTION SCHEME 14

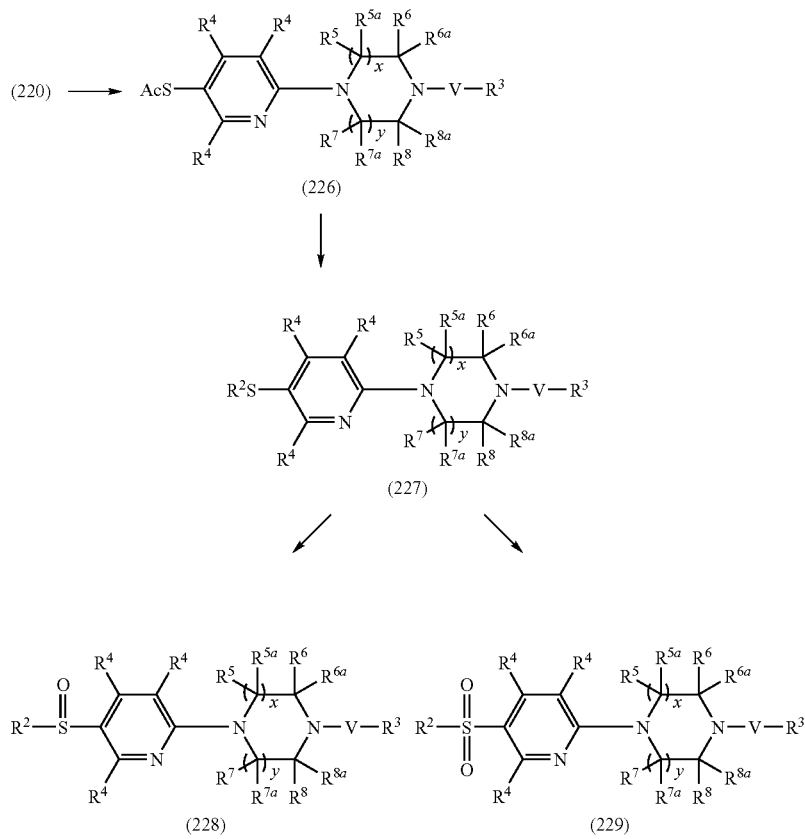

Reaction of amine (220) with sodium nitrite in the presence of a Lewis acid such as, but not limited to, boron trifluoride diethyl etherate in a solvent such as, but not limited to, N,N-dimethylformamide, generates a diazonium intermediate that can be converted into compound (226) by quenching the above reaction mixture with acetyl sulfide. Hydrolysis of the thioester compound (226) in the presence of a base such as, but not limited to, sodium hydroxide, produces a thiol intermediate that can be converted into the desired sulfide product (227) (formula (I), W=—S—) with an appropriate $R^2X$ in the presence of a base such as, but not limited to, sodium hydride in a solvent such as, but not limited to, tetrahydrofuran, 1,4-dioxane or N,N-dimethylformamide. Treatment of compound (227) with an oxidizing agent such as, but not limited to, sodium periodate in a mixture of methanol and water affords the sulfoxide compound (228) (formula (I), W=—S(O)—).

Alternatively, the sulfide compound (227) can be treated with trifluoro acetic anhydride and hydrogen peroxide in a solvent such as, but not limited to, dichloromethane to give the sulfone product (229) (formula (I), W=—S(O)$_2$—).

Alternatively, the compounds of formula (I) of the invention where G, J and L are C(R$^4$), M is N, W is —NHS(O)$_2$— and V is —C(O)—, —S(O)$_2$— or —C(R$^{11}$)H— can be synthesized following the general procedure as described in Reaction Scheme 15.

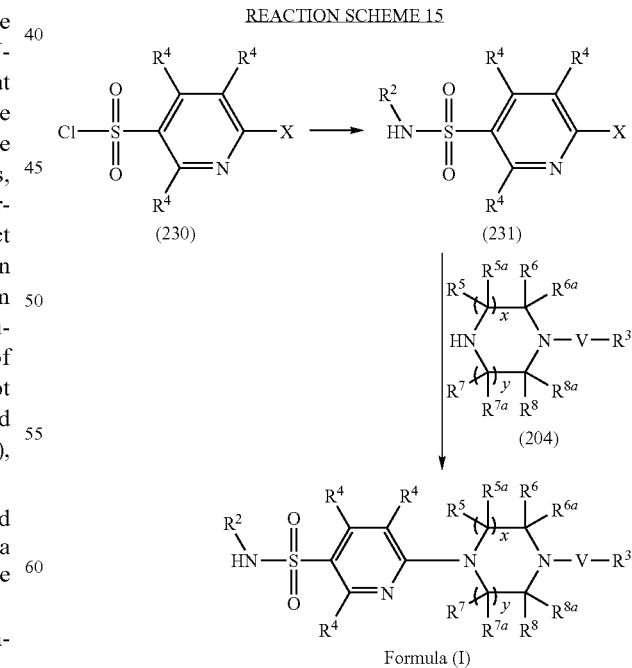

REACTION SCHEME 15

Reaction of the pyridyl sulfonyl chloride (230) with an appropriate amine (R$^2$NH$_2$) in the presence of a base such as, but not limited to, triethylamine and catalytical amount of N,N-dimethylformamide in a solvent such as, but not limited to, dichloromethane produces the sulfonamide compound (231). Treatment of (231) with a piperazine compound (204) in the presence of a base such as, but not limited to, potassium carbonate and tetrabutyl ammonium bromide in a solvent such as, but not limited to, dioxane leads to the formation of compound of formula (I) (W=—NHS(O)$_2$—). Alternatively, the chloride or bromide compound (231, X=Cl or Br) can react with a piperazine compound (204) under Buchwald amination reaction conditions (*J. Org. Chem.* 1997, 62, 4197) to form the desired product of formula (I).

Alternatively, the compounds of formula (I) of the invention where G, J and M are C(R$^4$), L is N, W is —C(O)N(R$^1$)— and V is —C(O)—, —S(O)$_2$— or —C(R$^{11}$)H— can be synthesized following the general procedure as described in Reaction Scheme 16.

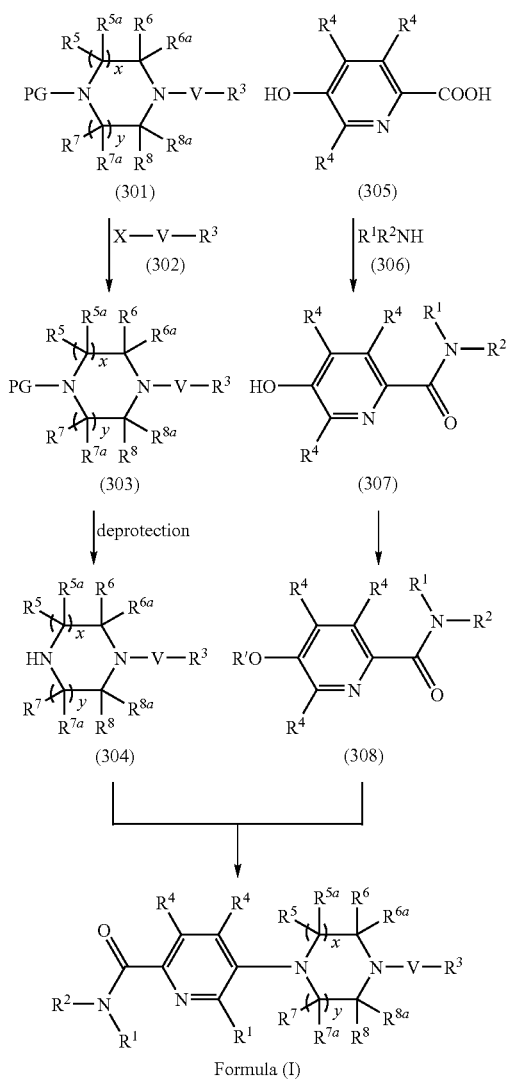

Compound (303): To a stirred solution of a compound of formula (301) (1 equivalent) in a solvent, such as dichloromethane, chloroform or toluene, but not limited to, at 0° C. in the presence of a base such as diisopropylethylamine, is added a solution of a compound of formula 102 (1 equivalent). The resulting mixture is stirred at ambient temperature for 8-24 h. The reaction is quenched with water. The organic phase is washed with water, dried over a drying agent such as anhydrous Na$_2$SO$_4$, filtered and concentrated in vacuo to yield compound (303).

Compound (304): A solution of compound of formula of (303) obtained above is dissolved in an adequate solvent and the protection group PG is removed under standard deprotection conditions such as hydrolysis or hydrogenation to obtain the amine of formula (304).

Compound (307): To a solution of 5-hydroxypyridine-2-carboxylic acid (1 equivalent) in a solvent such as dichloromethane, chloroform or toluene, is added a base such as triethylamine, diisopropylethylamine, followed by 1-hydroxybenzotriazole monohydrate (1 equivalent) and a coupling agent (1 equivalent) such as EDCI. The resulting mixture is stirred for 15-60 min and the amine of formula (306) (1 equivalent) is added. After stirring for 18-24 hours, the reaction mixture is diluted with dichloromethane, washed with water, dried over anhydrous Na$_2$SO$_4$, filtered and concentrated in vacuo. Purification by flash chromatography yields compound (307).

Compound (308): To a solution of compound of formula (307) obtained above (1 equivalent) at 0° C. in a solvent such as dichloromethane is added triethylamine (1.5 to 2.5 equivalent) followed by dropwise addition of a solution of trifluoromethanesulfonic anhydride (1.1 to 1.5 equivalent) in a solvent such as dichloromethane. The resulting mixture is stirred at 0° C. for 3-8 h and then quenched with water. The organic layer is separated, dried over anhydrous MgSO$_4$, filtered and concentrated in vacuo. Purification by flash column chromatography affords compound (308).

Compound of Formula (I): This compound is obtained using Buchwald reaction. In general, a flask under argon atmosphere is charged with a base such as cesium carbonate or potassium carbonate, palladium catalyst, such as palladium diacetate and a ligand such as BINAP. A solution of compound (308) and compound (304) in toluene is added via syringe. The reaction mixture is then heated at 100° C. for 26 h, cooled to ambient temperature, diluted with toluene, filtered and concentrated in vacuo. The crude product was purified via flash column chromatography affords compound of Formula (I).

Alternatively, the compounds of formula (I) of the invention where G, J and M are C(R$^4$), L is N, W is —C(O)NH— and V is —C(O)—, —S(O)$_2$— or —C(R$^{11}$)H— can be synthesized following the general procedure as described in Reaction Scheme 17.

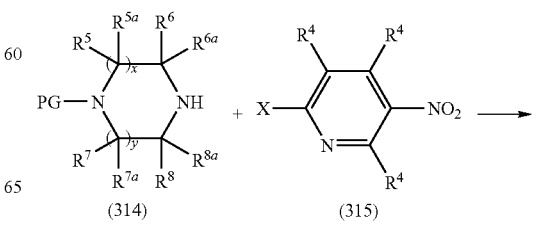

The starting materials for the above reaction scheme are commercially available or can be prepared according to methods known to one skilled in the art or by methods disclosed herein. In general, the compounds of the invention are prepared in the above reaction scheme as follows:

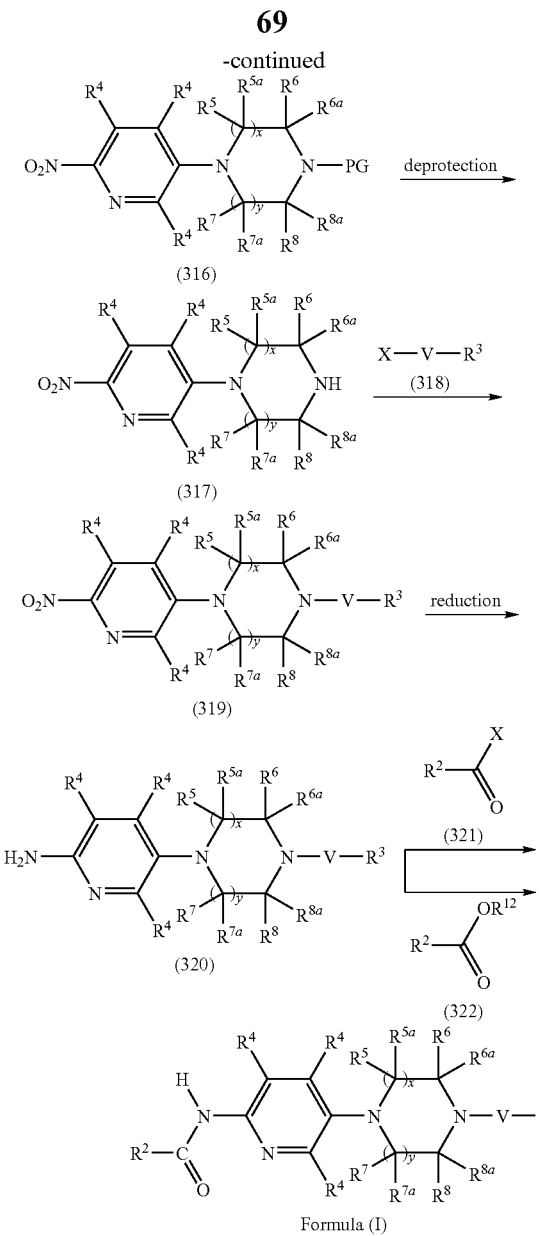

The starting materials for the above reaction scheme are commercially available or can be prepared according to methods known to one skilled in the art or by methods disclosed herein. In general, the compounds of the invention are prepared in the above reaction scheme as follows:

Compound 316. To a stirred solution of the amine of formula (314) (1 equivalent) in a solvent such as dichloromethane or toluene is added the solution of a chloride of formula (315) (1 equivalent) in a solvent such as dichloromethane or toluene in the presence of a base such as triethylamine or Hunigs base. The resulting mixture is stirred at ambient temperature for an adequate time period and then quenched with water. The organic phase is washed with $H_2O$, brine, dried over and then concentrated in vacuo to afford the product of formula (316).

Compound 317. A solution of compound of formula of (316) obtained above is dissolved in an adequate solvent and the protection group PG is removed under standard deprotection conditions such as hydrolysis or hydrogenation to obtain the amine of formula (317).

Compound 319. The mixture of a pyridine compound of formula (317) (1 equivalent) and the compound of formula (318) (1.5 equivalent) in an adequate solvent is heated at reflux for 4-24 hours. To the reaction mixture is added a basic solution such as NaOH solution. The aqueous layer is extracted by an organic solvent such as dichloromethane or ethyl acetate. The combined organic phase is dried, then evaporated to dryness. The crude compound is purified by column chromatography or crystallization to afford the compound of formula (319).

Compound 320. The nitro compound of formula (319) can be reduced to the corresponding amine compound of formula (320) using a standard hydrogenation process known to one skilled in the art.

Compound of Formula (I):

Method A: To a stirred solution of compound of formula (320) (1 equivalent) in a solvent such as dichloromethane, acetonitrile or toluene is added the solution of a compound of formula (321) (1 equivalent) in the presence of a base such as triethylamine or Hunigs base (1 equivalent) at 0° C. The resulting mixture is stirred at ambient temperature for 8-24 hours and then quenched with water. The organic phase is washed with $H_2O$, brine, dried and then concentrated in vacuo to afford the compound of formula (I).

Method B: To a solution of the compound of formula (322) (1 equivalent) in a solvent such as dichloromethane, toluene or THF is added a base such as triethylamine or Hunigs base (2.5 equivalent), followed by the addition of a coupling agent such as (3-dimethylaminopropyl)ethyl carbodiimide (1.1 equivalent). The resulting mixture is stirred for 15 minutes to an hour and an amine of formula (320) (1.1 equivalent) is added. The mixture is stirred at ambient temperature for 8-24 hours, then washed with water, dried and concentrated in vacuo. Purification by column chromatography or crystallization from a suitable solvent affords the compound of formula (I).

Alternatively, the compounds of formula (I) of the invention where G, J and M are $C(R^4)$, L is N, W is —NHC(O)NH— and V is —C(O)—, —S(O)$_2$— or —C($R^{11}$)H— can be synthesized following the general procedure as described in Reaction Scheme 18.

REACTION SCHEME 18

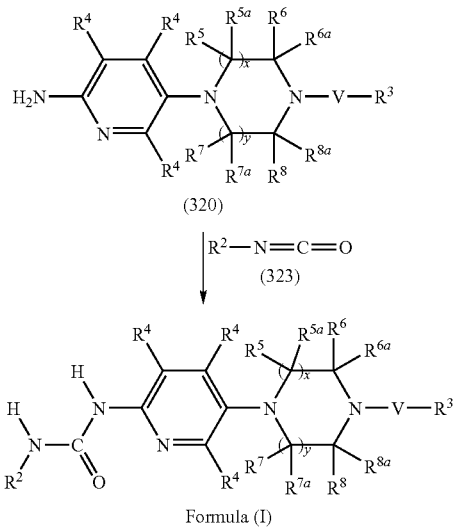

The starting materials for the above reaction scheme are commercially available or can be prepared according to methods known to one skilled in the art or by methods disclosed herein. In general, the compounds of the invention are prepared in the above reaction scheme as follows:

Compound of formula (I). To a stirred solution of the compound of formula (320) (1 equivalent) in an anhydrous solvent such as dimethylformamide is added an isocyanate of formula (323) (3 equivalent), and the mixture is then heated to 60-80° C. for 4-24 hours. The mixture is concentrated in vacuo. Purification of the crude product by column chromatography or crystallization from a suitable solvent affords the compound of formula (I).

Alternatively, the compounds of formula (I) of the invention where G, J and M are C($R^4$), L is N, W is —S(O)$_2$NH— and V is —C(O)—, —S(O)$_2$— or —C($R^{11}$)H— can be synthesized following the general procedure as described in Reaction Scheme 19.

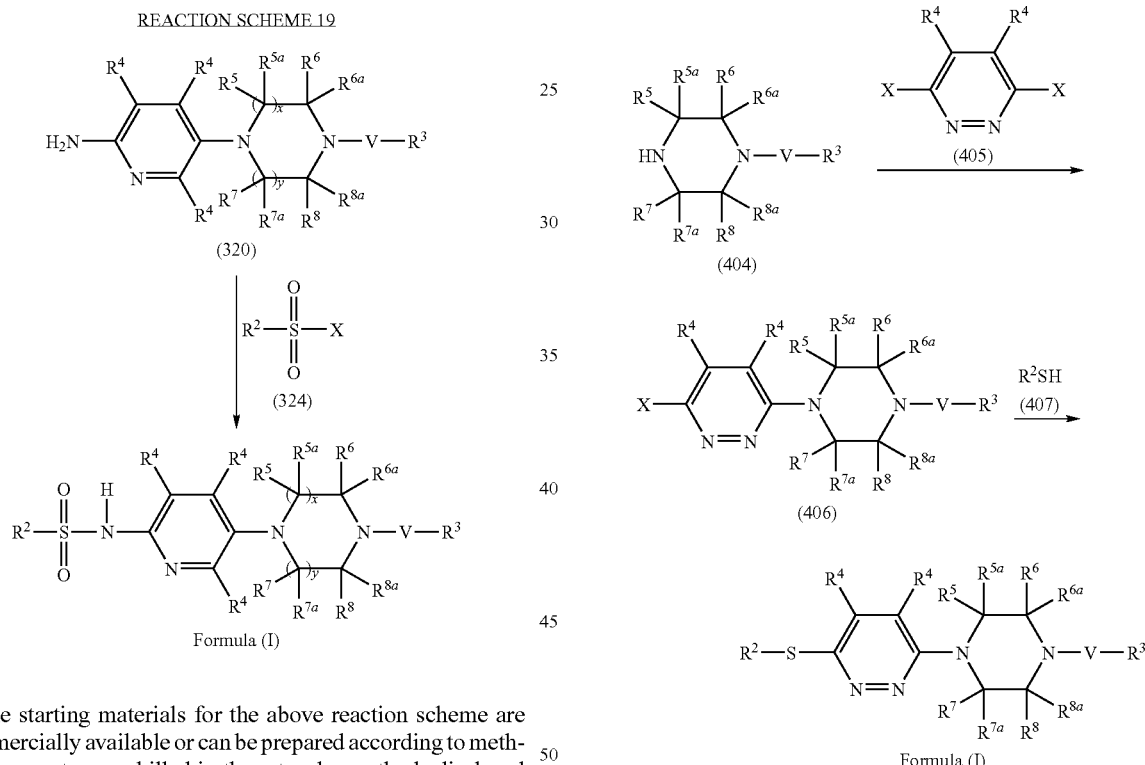

The starting materials for the above reaction scheme are commercially available or can be prepared according to methods known to one skilled in the art or by methods disclosed herein. In general, the compounds of the invention are prepared in the above reaction scheme as follows:

Compound of formula (I): To a solution of compound of formula (320) (1 equivalent) in a solvent such as dichloromethane, acetonitrile or toluene is added slowly the solution of compound of formula (324) (1 equivalent) at 0° C. The resulting mixture is stirred at ambient temperature for 8-24 hours and then quenched with water. After removal of solvent, the product was purified by chromatography to afford the compound of formula (I).

Alternatively, the compounds of formula (I) of this invention where G and J are C($R^4$), L and M are N, W is S and V is —C(O)—, —S(O)$_2$— or —C($R^{11}$)H— can be synthesized following the general procedure as described in Reaction Scheme 20.

The starting materials for the above reaction scheme are commercially available or can be prepared according to methods known to one skilled in the art or by methods disclosed herein. In general, the compounds of the invention are prepared in the above reaction scheme as follows:

Compound 403. To a stirred solution of the amine of formula (401) (1 equivalent) in a solvent such as dichloromethane or toluene is added the solution of a compound of formula (402) (1 equivalent) in a solvent such as dichloromethane or toluene in the presence of a base such as triethylamine or Hunigs base. The resulting mixture is stirred at ambient temperature for an adequate time period and then quenched with water. The organic phase is washed with H$_2$O, brine, dried over and then concentrated in vacuo to afford the product of formula (403).

Compound 404. A solution of compound of formula of (403) obtained above is dissolved in an adequate solvent and the protecting group PG is removed under standard deprotection conditions such as hydrolysis or hydrogenation to obtain the amine of formula (404).

Compound 406. The mixture of a pyridazine compound of formula (405) (1 equivalent) and the compound of formula (404) obtained above (1.5 equivalent) in an adequate solvent is heated at reflux for 4-24 hours. To the reaction mixture is added a basic solution such as NaOH solution. The aqueous layer is extracted by an organic solvent such as dichloromethane or ethyl acetate. The combined organic phase is dried, then evaporated to dryness. The crude compound is purified by column chromatography or crystallization to afford the compound of formula (406).

Compound of formula (I). A mixture of compound (406) (1 equivalent), a thiol compound of formula (407) (1 equivalent) and a base, such as, but not limited to, sodium hydroxide (1 equivalent) in an anhydrous solvent, such as, but not limited to, tetrahydrofuran, 1,4-dioxane, is refluxed for 8-12 h. The reaction mixture is cooled, diluted with water, acidified, then extracted with an organic solvent, such as, but not limited to, dichloromethane. The organic layer is separated and dried over anhydrous $MgSO_4$ to yield compound of formula (I) where G and J are $C(R^4)$, L and M are N, W is —S— and V is —C(O)—, —S(O)$_2$— or —C($R^{11}$)H—.

Alternatively, the compounds of formula (I) of this invention where G and J are $C(R^4)$, L and M are N, W is —O— and V is —C(O)—, —S(O)$_2$— or —C($R^{11}$)H— can be synthesized following the general procedure as described in Reaction Scheme 21.

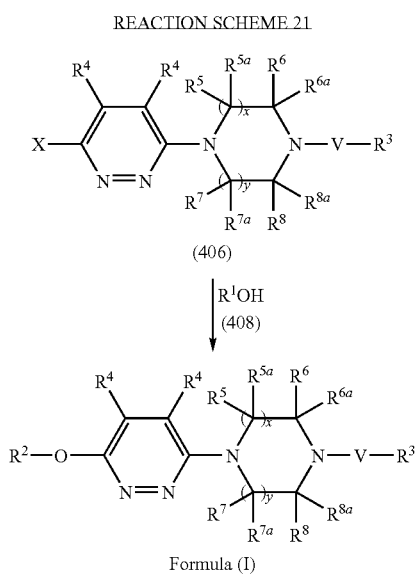

The starting materials for the above reaction scheme are commercially available or can be prepared according to methods known to one skilled in the art or by methods disclosed herein. In general, the compounds of the invention are prepared in the above reaction scheme as follows:

Compound of formula (I). To a mixture of compound (406) (1 equivalent) and an alcohol of formula (408) (1 equivalent) in an anhydrous solvent, such as, but not limited to, benzene or toluene is added 60% NaH (1 equivalent). The reaction mixture is refluxed for 1-4 h with stirring, then cooled to ambient temperature, diluted with water and extracted with an organic solvent, such as, but not limited to, ethyl acetate or dichloromethane. The organic layer is separated, washed with water, dried over anhydrous $MgSO_4$, filtered and concentrated. Purification by column chromatography affords the compound of formula (I) where G and J are $C(R^4)$, L and M are N, W is —O— and V is —C(O)—, —S(O)$_2$— or —C($R^{11}$)H—

Alternatively, the compounds of formula (I) of this invention where G and J are $C(R^4)$, L and M are N, W is —NR$^1$— and V is —C(O)—, —S(O)$_2$— or —C($R^{11}$)H— can be synthesized following the general procedure as described in Reaction Scheme 22.

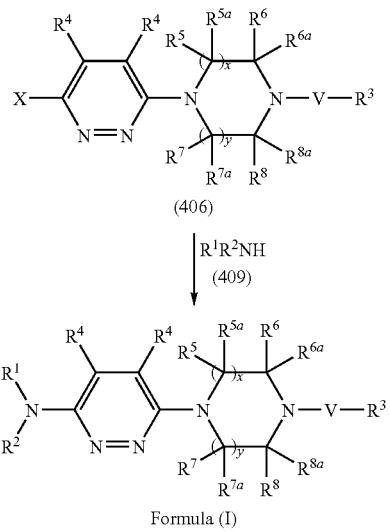

The starting materials for the above reaction scheme are commercially available or can be prepared according to methods known to one skilled in the art or by methods disclosed herein. In general, the compounds of the invention are prepared in the above reaction scheme as follows:

Compound of formula (I). To a stirred solution of compound (406) (1 equivalent) and an amine of formula (409) (1.5-2 equivalent) in an organic solvent, such as, but not limited to, acetone or n-butanol is added 2-3 equivalent of acid in water. The reaction is refluxed for 8-16 h while stirring, then cooled to ambient temperature and the solvent is removed in vacuo. Purification by purified by column chromatography affords the compound of formula (I) where G and J are $C(R^4)$, L and M are N, W is —NR$^1$— and V is —C(O)—, —S(O)$_2$— or —C($R^{11}$)H—.

Alternatively, the compounds of formula (I) of this invention where G and J are $C(R^4)$, L and M are N, W is —S(O)$_t$— (where t ~1 or 2) and V is —C(O)—, —S(O)$_2$— or —C($R^{11}$)H— can be synthesized following the general procedure as described in Reaction Scheme 23.

REACTION SCHEME 23

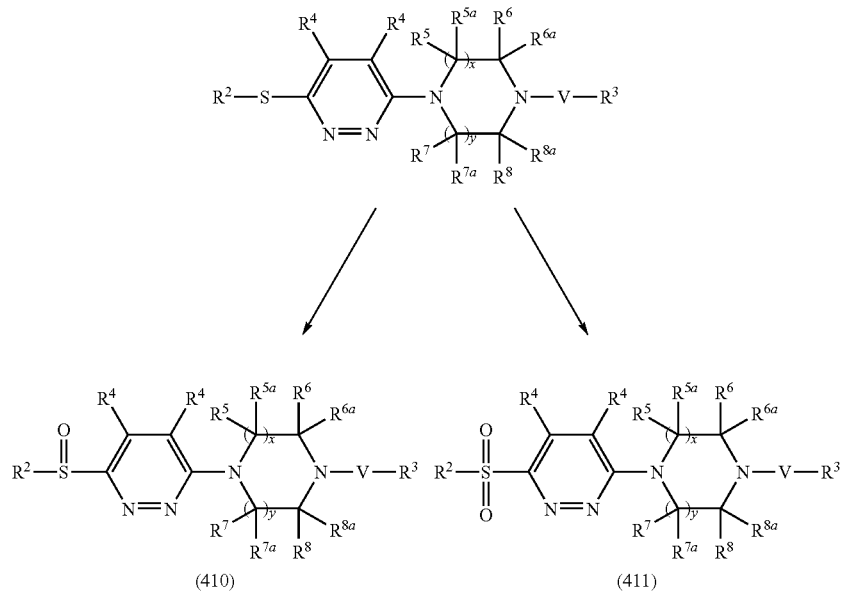

(410)   (411)

The starting materials for the above reaction scheme are commercially available or can be prepared according to methods known to one skilled in the art or by methods disclosed herein. In general, the compounds of the invention are prepared in the above reaction scheme as follows:

Compound (410). To a solution of sodium periodate (1 equivalent) in an appropriate solvent, such as, but not limited to, MeOH and water mixture is added the thioether compound (1 equivalent). The reaction mixture is stirred in an ice-bath for 4-8 hours and then diluted with an organic solvent, such as, but not limited to, dichloromethane. The organic layer is separated and washed with water, dried over anhydrous Na$_2$SO$_4$, concentrated in vacuo. Purification by column chromatography affords the compound (410).

Compound (411). A mixture of the thioether compound (1 equivalent) and an oxidizing agent, such as, but not limited to, m-CPBA (2-4 equivalent) in an appropriate solvent, such as, but not limited to, dichloromethane is stirred in an ice-bath for 2-4 h, and the stirring is continued for another 12-24 hours. The reaction mixture is diluted with an organic solvent such as dichloromethane, washed with a basic solution, such as NaOH solution, and brine. Organic layer is separated and dried over anhydrous Na$_2$SO$_4$, then concentrated in vacuo. Purification by column chromatography yields the compound (411).

Alternatively, the compounds of formula (I) of the invention where G and J are C(R$^4$), L and M are N, W is —NH— and V is —C(O)—, —S(O)$_2$— or —C(R$^{11}$)H— can be synthesized following the general procedure as described in Reaction Scheme 24.

REACTION SCHEME 24

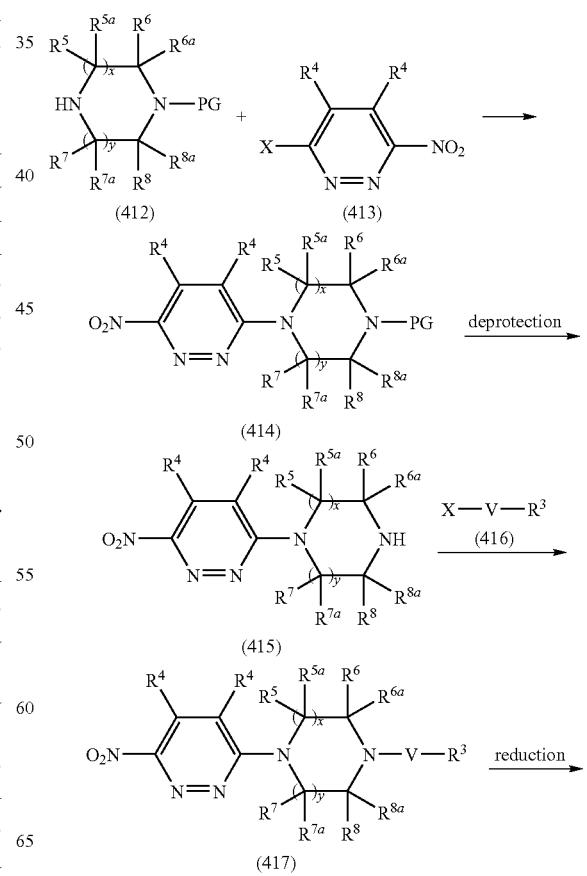

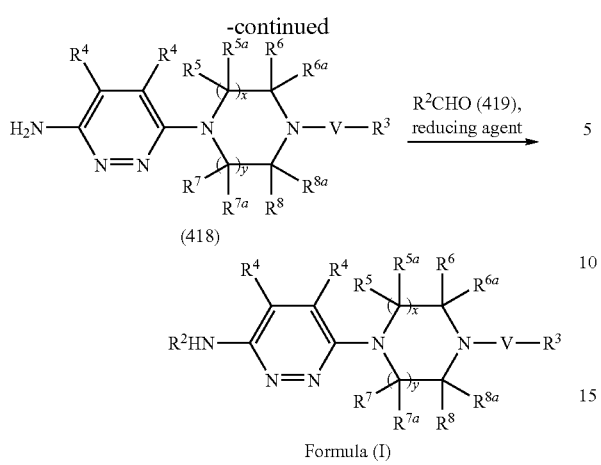

Formula (I)

The starting materials for the above reaction scheme are commercially available or can be prepared according to methods known to one skilled in the art or by methods disclosed herein. In general, the compounds of the invention are prepared in the above reaction scheme as follows:

Compound 414. To a stirred solution of the amine of formula (412) (1 equivalent) in a solvent such as dichloromethane or toluene is added the solution of a chloride of formula (413) (1 equivalent) in a solvent such as dichloromethane or toluene in the presence of a base such as triethylamine or Hunigs base. The resulting mixture is stirred at ambient temperature for an adequate time period and then quenched with water. The organic phase is washed with $H_2O$, brine, dried over and then concentrated in vacuo to afford the product of formula (414).

Compound 415. A solution of compound of formula of (414) obtained above is dissolved in an adequate solvent and the protection group PG is removed under standard deprotection conditions such as hydrolysis or hydrogenation to obtain the amine of formula (415).

Compound 417. The mixture of a pyridine compound of formula (415) (1 equivalent) and the compound of formula (416) (1.5 equivalent) in an adequate solvent is heated at reflux for 4-24 hours. To the reaction mixture is added a basic solution such as NaOH solution. The aqueous layer is extracted by an organic solvent such as dichloromethane or ethyl acetate. The combined organic phase is dried, then evaporated to dryness. The crude compound is purified by column chromatography or crystallization to afford the compound of formula (417).

Compound 418. The nitro compound of formula (417) can be reduced to the corresponding amine compound of formula (418) using a standard hydrogenation process known to one skilled in the art.

Compound of formula (I). Reaction of amine (418) with an appropriate aldehyde of formula (419) in the presence of a reducing agent such as, but not limited to, sodium borohydride in a solvent such as, but not limited, ethanol affords the compound of formula (I) where G and J are $C(R^4)$, L and M are N, W is —NH— and V is —C(O)—, —S(O)$_2$— or —C($R^{11}$)H—.

Alternatively, the compounds of formula (I) of the invention where G and J are $C(R^4)$, L and M are N, W is —O— and V is —C(O)—, —S(O)$_2$— or —C($R^{11}$)H— can be synthesized following the general procedure as described in Reaction Scheme 25.

REACTION SCHEME 25

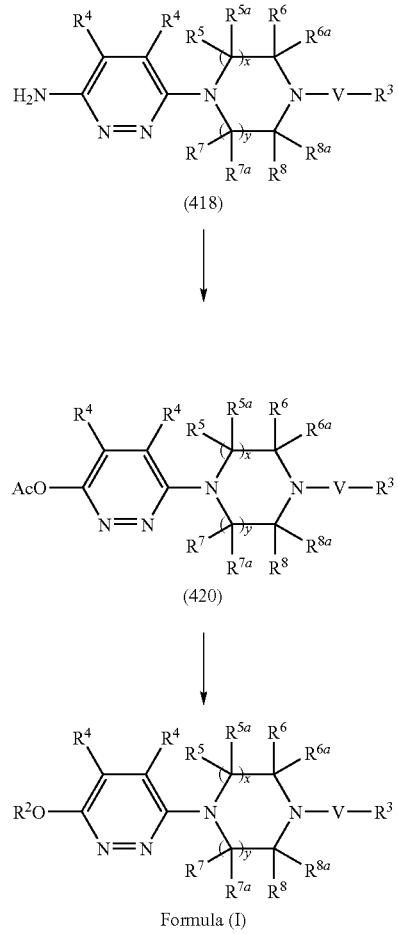

Formula (I)

Reaction of amine (418) with sodium nitrite in the presence of a Lewis acid such as, but not limited to, boron trifluoride diethyl etherate in a solvent such as, but not limited to, N,N-dimethylformamide, generates a diazonium intermediate that can be converted into the acetoxy compound (420) by quenching the above reaction mixture with acetic anhydride. Hydrolysis of the ester compound (420) in the presence of a base such as, but not limited to, sodium hydroxide, produces a hydroxy intermediate that can be converted into the desired product of formula (I) (W=—O—) with an appropriate $R^2X$ in the presence of a base such as, but not limited to, sodium hydride in a solvent such as, but not limited to, tetrahydrofuran or N,N-dimethylformamide.

Alternatively, the compounds of formula (I) of the invention where G and J are $C(R^4)$, L and M are N, W is —S(O)$_t$— (where t is 0, 1 or 2) and V is —C(O)—, —S(O)$_2$— or —C($R^{11}$)H— can be synthesized following the general procedure as described in Reaction Scheme 26.

REACTION SCHEME 26

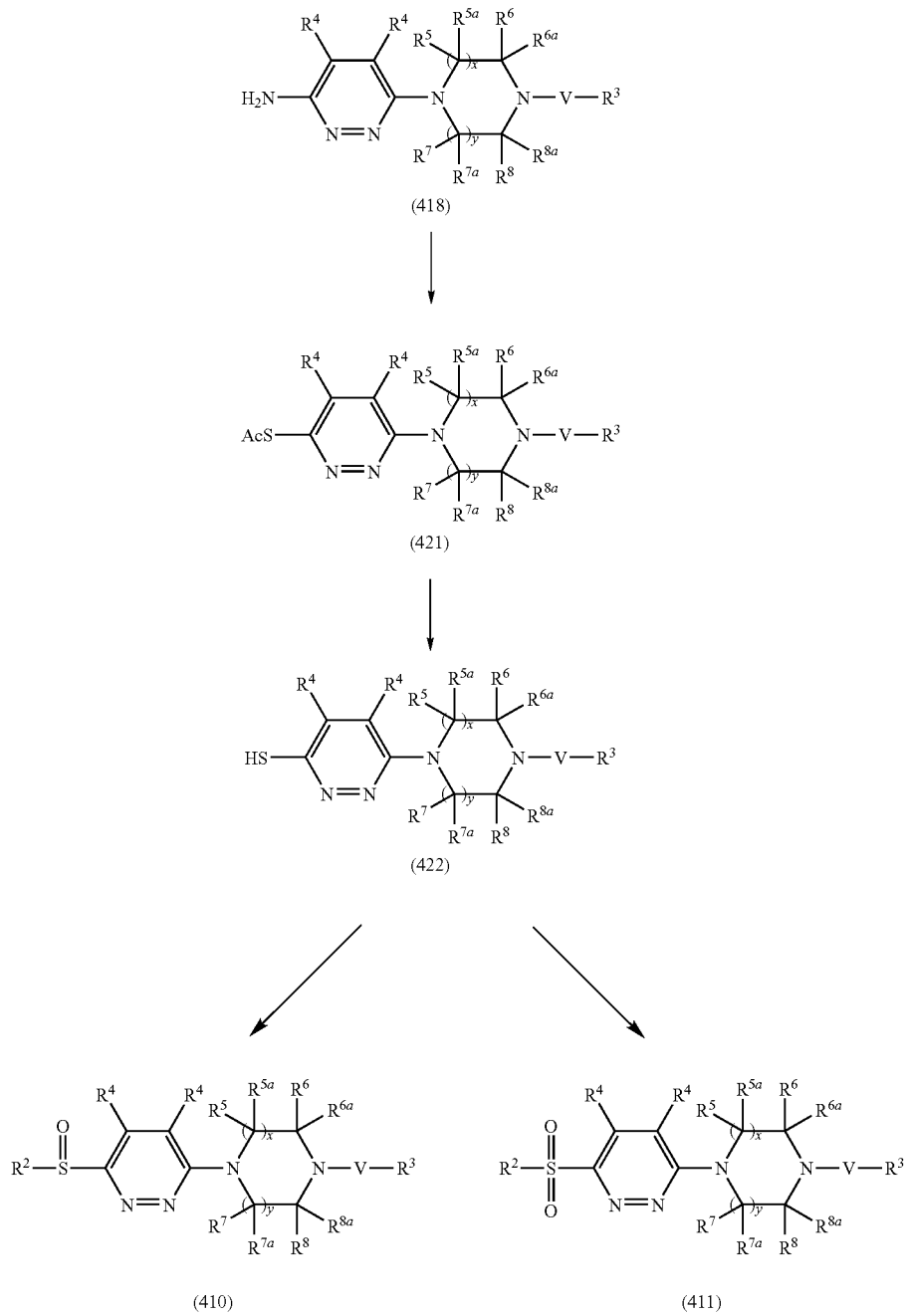

Reaction of amine (418) with sodium nitrite in the presence of a Lewis acid such as, but not limited to, boron trifluoride diethyl etherate in a solvent such as, but not limited to, N,N-dimethylformamide, generates a diazonium intermediate that can be converted into compound (421) by quenching the above reaction mixture with acetyl sulfide. Hydrolysis of the thioester compound (421) in the presence of a base such as, but not limited to, sodium hydroxide, produces a thiol intermediate that can be converted into the desired sulfide product (422) (formula (I), W=—S—) with an appropriate $R^2X$ in the presence of a base such as, but not limited to, sodium hydride in a solvent such as, but not limited to, tetrahydrofuran, 1,4-dioxane or N,N-dimethylformamide. Treatment of compound (422) with an oxidizing agent such as, but not limited to, sodium periodate in a mixture of methanol and water affords the sulfoxide compound (410) (formula (I), W=—S(O)—). Alternatively, the sulfide compound (422) can be treated with trifluoro acetic anhydride and hydrogen peroxide in a solvent such as, but not limited to, dichloromethane to give the sulfone product (411) (formula (I), W=—S(O)$_2$—).

Alternatively, the compounds of formula (I) of this invention where G and L are N, J and M are C($R^4$), W is —NHC(O)—, V is —C(O)—, $R^5$, $R^{5a}$, $R^6$, $R^{6a}$, $R^7$, $R^{7a}$, $R^8$ and $R^{8a}$ are H can be synthesized following the general procedure as described in Reaction Scheme 27.

REACTION SCHEME 27

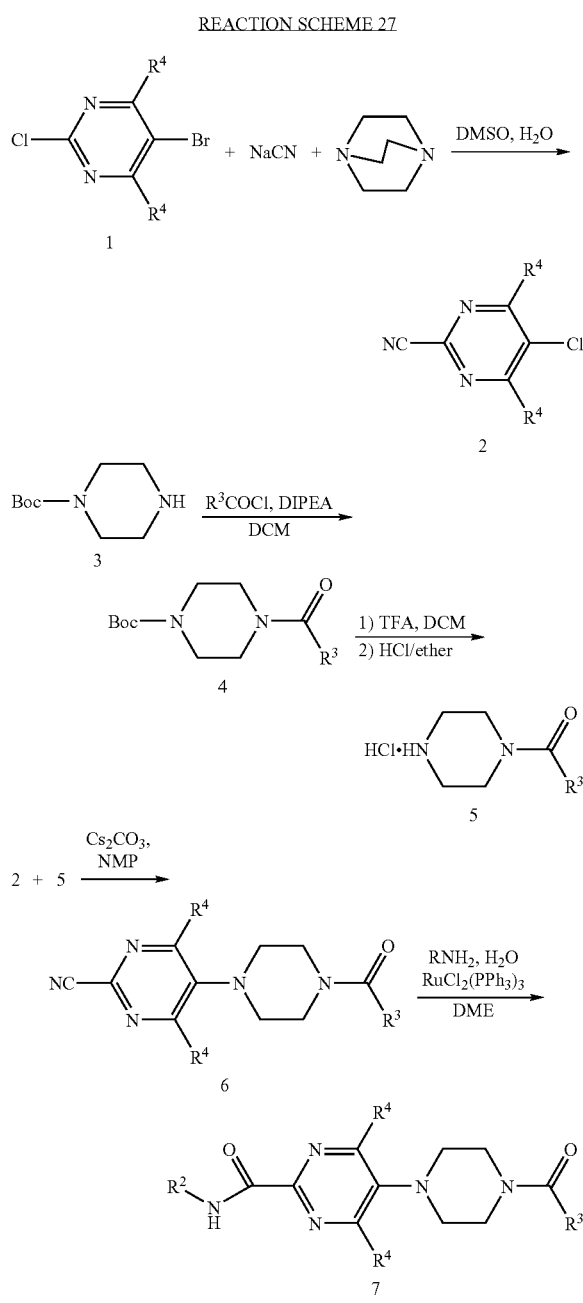

vacuo to afford product 4. Without further purification, compound 4 is dissolved in excess hydrochloric acid in ether solution, concentrated to yield a colourless solid compound 5.

Compound 6. A mixture of compound 2, 5 and cesium carbonate in NMP is heated. The reaction mixture is cooled to room temperature, concentrated in vacuo, added water, extracted with dichloromethane to yield compound 6.

Compound 7. A mixture of compound 6, appropriate amine and triphenylphosphine rutheniumchloride (catalytic amount) in DME and water is heated. The reaction mixture is cooled to room temperature, solvent is removed in vacuo, added water, extracted with ethyl ether. Organic layer is washed with brine solution, dried over anhydrous sodium sulphate, concentrated to yield compound 7.

Alternatively, compounds of formula (I) of this invention where G and L are N, J and M are C($R^4$), W is —C(O)NH—, —$SO_2$NH— and —NHC(O)NH—, V is —C(O)—, $R^5$, $R^{5a}$, $R^6$, $R^{6a}$, $R^7$, $R^{7a}$, $R^8$ and $R^{8a}$ are H can be synthesized following the general procedure as described in Reaction Scheme 28.

REACTION SCHEME 28

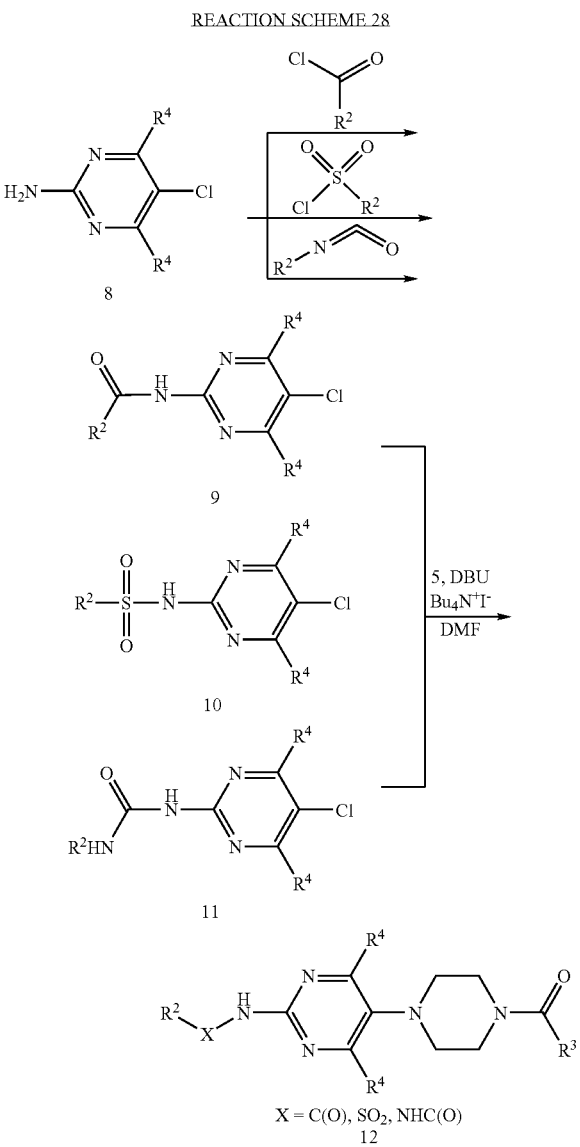

The starting materials for the above reaction scheme are commercially available or can be prepared according to methods known to one skilled in the art or by methods disclosed herein. In general, the compounds of the invention are prepared in the above reaction scheme as follows:

Compound 2. A mixture of 5-bromo-2-chloropyrimidine (1), sodium cyanide, 1,4-diazabicyclo[2,2,2]octane (catalytic amount) in DMSO and water is stirred at room temperature. The reaction is quenched with water and extracted with dichloromethane to yield compound 2.

Compound 5. To a stirred solution of 1-Boc-piperazine (3) in dichloromethane is added appropriate acid chloride as a dichloromethane solution in the presence of N-ethyldiisopropyl amine. The resulting mixture is stirred at RT and then quenched with water. The organic phase is washed with $H_2O$, saturated NaCl, dried over $MgSO_4$ and then concentrated in The starting materials for the above reaction scheme are commercially available or can be prepared according to methods known to one skilled in the art or by methods disclosed herein. In general, the compounds of the invention are prepared in the above reaction scheme as follows:

Compounds 9 and 10. To a stirred solution of 2-amino-5-chloropyrimidine (8) in dichloromethane is added appropriate acid or sulfonyl chloride as a dichloromethane solution in the presence of triethylamine. The resulting mixture is stirred at RT and then quenched with water. The organic phase is washed with H$_2$O, saturated NaCl, dried over MgSO$_4$ and then concentrated in vacuo to afford product 9 or 10.

Compound 11. To a stirred solution of 2-amino-5-chloropyrimidine (8) in anhydrous ethanol is added appropriate isocyanate in the presence of triethylamine. The resulting mixture is concentrated in vacuo. Crystallization of the residue from ether/hexane afforded product 11.

Compound 12. A solution of compound 9, 10 or 11 in DMF is treated with compound 5. The mixture is diluted with EtOAc. The organic phase is washed with H$_2$O, saturated NaCl, and then dried over MgSO$_4$. The organic phase is concentrated in vacuo to afford product 12.

Alternatively, compounds of formula (I) of this invention where G and M are C(R$^4$), J and L are N, W is —C(O)NH—, —SO$_2$NH— and —NHC(O)NH—, V is C(O), R$^5$, R$^{5a}$, R$^6$, R$^{6a}$, R$^7$, R$^{7a}$, R$^8$ and R$^{8a}$ are H can be synthesized following the general procedure as described in Reaction Scheme 29.

REACTION SCHEME 29

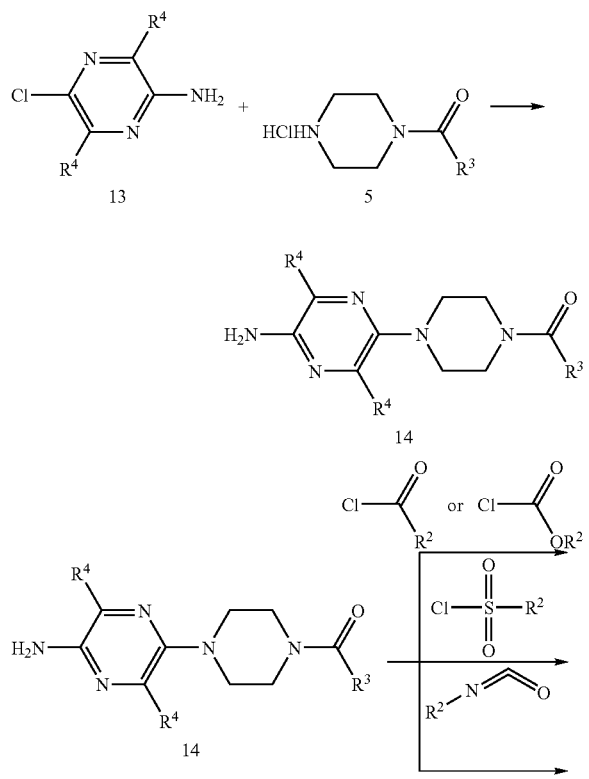

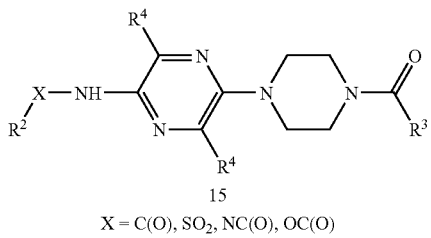

X = C(O), SO$_2$, NC(O), OC(O)

The starting materials for the above reaction scheme are commercially available or can be prepared according to methods known to one skilled in the art or by methods disclosed herein. In general, the compounds of the invention are prepared in the above reaction scheme as follows:

Compound 14. The mixture of 2-amino-5-bromo-pyrazine (13) and compound 5 is heated. To the reaction mixture, after cooling down to room temperature, is added 1N NaOH and dichloromethane, and the aqueous layer is extracted with dichloromethane. The combined organic phase is dried over Na$_2$SO$_4$, evaporated to dryness. The crude compound was purified by flash chromatography to give the desired product 14.

Compound 15. To a stirred solution of compound 14 in anhydrous DMF is added appropriate isocyanate, and the mixture is heated. The mixture is concentrated in vacuo. The crude product is purified by flash chromatography to give the desired product 15.

To a stirred solution of compound 14 in DCM is added appropriate carboxylic chloride, chloroformate or sulfonyl chloride in the presence of triethylamine. The resulting mixture is stirred and then quenched with water. The organic phase is washed with H$_2$O, saturated NaCl, dried over MgSO$_4$ and then concentrated in vacuo to afford the desired product 15.

Alternatively, compounds of formula (I) of this invention where G and L are (CR$^4$), J and M are N, W is —NHC(O)—, V is C(O), G is C(R$^4$), R$^5$, R$^{5a}$, R$^6$, R$^{6a}$, R$^7$, R$^{7a}$, R$^8$ and R$^{8a}$ are H can be synthesized following the general procedure as described in Reaction Scheme 30.

REACTION SCHEME 30

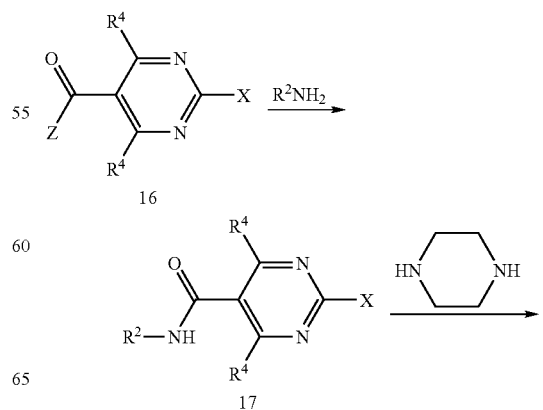

-continued

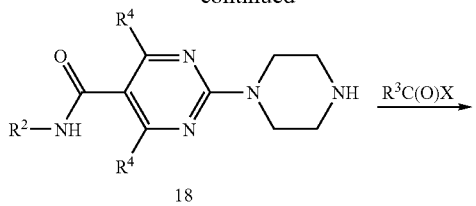

18

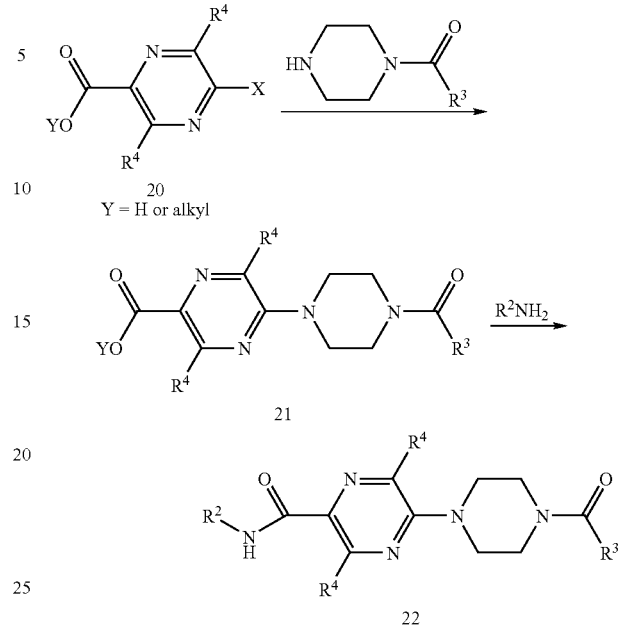

REACTION SCHEME 31

Compound 16 can be used as starting material. In compound 16, X is a leaving group such as chloro or sulfonyl groups. The sulfonyl compound can be prepared starting with X=SMe by oxidation using an oxidant such as, but not limited to, m-chloroperoxybenzoic acid. Z can be hydroxy (acid), alkoxy (ester) or halo (acyl halide). In general, the acid can be obtained by treatment of the corresponding ester by using a base such as, but not limited to lithium hydroxide. The acyl halide such as acyl chloride can be formed by reacting the acid with thionyl chloride. Starting from compound 16, compound 18 can be synthesized either by forming the amide bond first by reacting with an appropriate amine $R^2NH_2$ followed by introduction of the piperazine moiety or vice versa (starting from an ester). Starting from an acid, the coupling conditions such as, but not limited to, hydroxybenzotriazole/1-(3-dimethylaminopropyl)-3-ethylcarbodiimide/diisopropylethylamine/dichloromethane can be used to form the amide by reacting with the amine $R^2NH_2$. Alternatively, starting from an ester, the amide can be produced by mixing the ester with the amine $R^2NH_2$ and heating in microwave, or in the presence of sodium cyanide. Alternatively, starting from an acyl halide such as acyl chloride, the amide can be obtained by reacting with the amine $R^2NH_2$ in the presence of a base such as, but not limited to, triethylamine in a solvent such as, but not limited to, dichloromethane. The piperazine moiety can be introduced by using either piperazine or protected piperazine, for example, tert-butyloxycarbonylpiperazine. If the protected piperazine is used, a deprotection step can be carried out by treatment with an acid such as, but not limited to, trifluoroacetic acid or hydrochloric acid.

Reaction of 18 with an appropriate acyl chloride in the presence of a base such as, but not limited to, diisopropylethylamine in a solvent such as, but not limited to, dichloromethane gives the desired product 19.

Alternatively, compounds of formula (I) of this invention where L and J are $C(R^4)$, G and M are N, W is —NHC(O)—, V is —C(O)—, $R^5, R^{5a}, R^6, R^{6a}, R^7, R^{7a}, R^8$ and $R^{8a}$ are H can be synthesized following the general procedure as described in Reaction Scheme 31.

Compound 20 can be used as starting material. In compound 20, X is a leaving group such as chloro group. Reaction of compound 20 with the free base of 5 in the presence of a base such as, but not limited to, potassium carbonate and tetrabutylammonium iodide in a solvent such as, but not limited to, dimethoxyethane affords the formation of compound 21. In compound 21, Y can be hydroxy (acid) or alkoxy (ester). In general, the acid can be obtained by treatment of the corresponding ester by using a base such as, but not limited to lithium hydroxide. Starting from an acid, the coupling conditions such as, but not limited to, hydroxybenzotriazole/1-(3-dimethylaminopropyl)-3-ethylcarbodiimide/diisopropylethylamine/dichloromethane can be used to form the amide 22 by reacting with an appropriate amine $R^2NH_2$. Alternatively, starting from an ester, the amide 22 can be produced by mixing the ester with the amine $R^2NH_2$ and heating in microwave, or in the presence of sodium cyanide.

Pharmaceutical Compositions Comprising Combinations of an SCD-1 Inhibitor and One or More Drugs Having the Side Effect of Adverse Weight Gain The present invention relates to pharmaceutical compositions and methods of using the pharmaceutical compositions for the treatment of adverse weight gain associated with drug therapies. In general, the present invention provides a pharmaceutical composition comprising therapeutically effective amounts of an SCD-1 inhibitor and a drug therapy having the side effect of adverse weight gain. The pharmaceutical composition is in a medium generally accepted in the art for the delivery of the biologically active compound to mammals, e.g., humans. Such a medium includes all pharmaceutically acceptable carriers, diluents or excipients therefore, which is intended to mean substances, which are substantially harmless to the individual.

The term "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The pharmaceutical composition of the invention can be administered by any means known in the art, e.g., parenterally, orally, or by local administration. Details on techniques for formulation and administration are well described in the scientific and patent literature, e.g., the latest edition of Remington's Pharmaceutical Sciences, Maack Publishing Co., Easton Pa. The route of administration of the pharmaceutical composition of this invention will depend upon the condition or disease being treated, the type of drugs used with the SCD-1 inhibitor compound, the preferred method of administration and the like.

In one embodiment of the invention, an SCD-1 inhibitor in combination with one or more drug therapy in the form of a pharmaceutical composition is preferably administered orally. When the pharmaceutical composition is orally administered, an inert diluent or an assimilable edible carrier may be included, or it may be incorporated directly into the individual's diet. In general, therapeutically effective amounts of SCD-1 inhibitors suitable to practice the invention may range from about 0.01 mg/kg to about 500 mg/kg of body weight per subject per day, preferably in the range of about 0.05 mg/kg to about 100 mg/kg, preferably in the range of about 0.20 mg/kg to about 50 mg/kg, preferably in the range of about 0.50 mg/kg to about 20 mg/kg, preferably in the range of about 1.0 mg/kg to about 2.0 mg/kg. Therapeutically effective amounts of a drug therapy sufficient to effect treatment of a disease or condition, as defined herein, are well known to persons of ordinary skill in the art, and examples are disclosed in table 4 below.

Pharmaceutical formulations for oral administration can be formulated using pharmaceutically acceptable carriers well known in the art in dosages suitable for oral administration. Acceptable carriers can be solid or liquid. For example, solid form preparations include powders, tablets, pills, capsules, cachets, suppositories and dispersible granules. Liquid form preparations include solutions, suspensions and emulsions. Pharmaceutical formulations of the SCD-1 inhibitor and the drug therapy can be prepared according to known methods.

By way of example only, with reference to the following non-limiting examples table 4 below discloses representative oral dosage combinations used in the pharmaceutical compositions for daily administration to a human. The dosage form will typically be administered in a single daily dose or the total daily dosage may be administered in divided doses of 2 to 6 times daily. Furthermore, based on the properties of the compounds selected for administration, the dose may be administered less frequently, e.g. once every 2, 3, 4, 5, 6 days, weekly, twice weekly, monthly, etc. The SCD-1 inhibitor is mixed with the active component of the drug therapy and non-active ingredients in suitable proportions and compacted in the shape and size desired. Compounds of Formula I, such as XEN 1, are representative SCD-1 inhibitor compounds of the invention.

TABLE 4

Representative oral dosage combinations used in the pharmaceutical compositions

| SCD-1 inhibitor (XEN 1) as active | Drug Therapy as active | Non-active ingredients |
| --- | --- | --- |
| 70 mg-140 mg | 2 mg-8 mg Metformin Hydrocholride; Rosiglitazone Maleate (e.g. Avandia ®) as described in U.S. Pat. No. 5,002,953; chemically, (±)5-[[4-[2-(methyl-2-pyridinylamino)ethoxy]phenyl]-methyl]-2,4-thiazolidinedione, (Z)-2-butenedioate (1:1) | Hypromellose 2910, lactose monohydrate, magnesium stearate, microcrystalline cellulose, polyethylene glycol 3000, sodium starch glycolate, titanium dioxide, and triacetin. |
| 70 mg-140 mg | 10 mg-40 mg Fluoxetine Hydrochloride (e.g. prozac ®), chemically, (±)-N-methyl-3-phenyl-3-[(a,a,a-trifluoro-ptolyl)oxy]propylamine hydrochloride | Microcrystalline cellulose, magnesium stearate, crospovidone, hydroxypropyl methylcellulose, titanium dioxide, and polyethylene glycol. |
| 70 mg-140 mg | 5 mg-20 mg Olanzapine (e.g. Zyprexa ®); chemically, 2-methyl-4-(4-methyl-1-piperazinyl)-10H-thieno[2,3-b][1,5]benzodiazepine | Carnauba wax, crospovidone, hydroxypropyl cellulose, hypromellose, lactose, magnesium stearate, and microcrystalline cellulose. |
| 70 mg-140 mg | 25 mg-100 mg Sertraline hydrochloride (e.g. Zoloft ®); chemically, (1S-cis)-4-(3,4-dichlorophenyl)-1,2,3,4-tetrahydro-N-methyl-1-naphthalenamine Hydrochloride | Dibasic calcium phosphate dihydrate, D & C Yellow #10 aluminum lake, FD & C Blue #1 aluminum lake, FD & C Red #40 aluminum lake, FD & C Blue #2 aluminum lake, hydroxypropyl cellulose, hypromellose, magnesium stearate, microcrystalline cellulose, polyethylene glycol, polysorbate 80, sodium starch glycolate, synthetic yellow iron oxide, and titanium dioxide. |
| 70 mg-140 mg | 25 mg-35 mg Phenelzine Sulfate (e.g. Nardil ®); | Mannitol, USP; NF; croscarmellose sodium, NF; povidone, USP; edetate disodium, USP; magnesium stearate, NF; isopropyl alcohol, USP; purified water, USP; opadry orange Y30-13242A; simethicone emulsion, and USP. |
| 70 mg-140 mg | 100 mg-400 mg Carbamazepine (e.g. Tegretol ®); chemically, 5H-dibenz[b,f]azepine-5-carboxamide | Colloidal silicon dioxide, D&C Red No. 30 Aluminum Lake, FD&C Red No. 40, flavoring, gelatin, glycerin, magnesium stearate, sodium starch glycolate, starch, stearic acid, and sucrose. |

TABLE 4-continued

Representative oral dosage combinations used in the pharmaceutical compositions

| SCD-1 inhibitor (XEN 1) as active | Drug Therapy as active | Non-active ingredients |
|---|---|---|
| 70 mg-140 mg | 100 mg-800 mg Gabapentin (e.g. Neurotonin ®); chemically, 1-(aminomethyl)cyclohexaneacetic acid | Poloxamer 407, copolyvidonum, cornstarch, magnesium state, hydroxypropyl cellulose, talc, candelilla wax and purified water. |
| 70 mg-140 mg | 0.5 mg-4.0 mg Repaglinide (e.g. Prandin ®); chemically, S(+)2-ethoxy-4(2((3-methyl-1-(2-(1-piperidinyl)phenyl)-butyl)amino)-2-oxoethyl) benzole acid, | Iron oxides, calcium hydrogen phosphate (anhydrous), microcrystalline cellulose, maize starch, polacrilin potassium, povidone, glycerol (85%), magnesium stearate, meglumine, and poloxamer. |
| 70 mg-140 mg | 0.25 mg-4.0 mg Risperidone (e.g. Risperdal ®); chemically, 3-[2-[4-(6-fluoro-1,2-benzisoxazol-3-yl)-1-piperidinyl]ethyl]-6,7,8,9-tetrahydro-2-methyl-4Hpyrido[1,2-a]pyrimidin-4-one. | Colloidal silicon dioxide, hypromellose, lactose, magnesium stearate, microcrystalline cellulose, propylene glycol, sodium lauryl sulfate, and starch (corn). |
| 70 mg-140 mg | 5.0 mg-30 mg Aripiprazole (e.g. Abilify ™); chemically, 7-[4-[4-(2,3-dichlorophenyl)-1-piperazinyl]butoxy]-3,4-dihydrocarbostyril. | Lactose monohydrate, cornstarch, microcrystalline cellulose, hydroxypropyl cellulose, and magnesium stearate. |
| 70 mg-140 mg | 133.3 mg Lopinavir; 33.3 mg Ritonavir (e.g. Kaletra ®); chemically, Lopinavir is [1S-[1R*,(R*),3R*,4R*]]-N-[4-[[(2,6-dimethylphenoxy)acetyl]amino]-3-hydroxy-5-phenyl-1-(phenylmethyl)pentyl]tetrahydro-alpha-(1-methylethyl)-2-oxo-1(2H)-pyrimidineacetamide; chemically, Ritonavir is 10-Hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5R*,8R*,10R*,11R*)]. | FD&C Yellow No. 6, gelatin, glycerin, oleic acid, polyoxyl 35 castor oil, propylene glycol, sorbitol special, titanium dioxide, and water. |

Although it is preferable that the drug therapy is provided in a therapeutically effective amount, it is envisioned that the drug therapy may be provided in sub-therapeutic amounts, as the necessary therapeutically effective amount could be reached by administration of a number of individual doses.

The dosage regimen for the drug therapy with the SCD-1 inhibitor of this invention is selected in accordance with a variety of factors, including the type, age, weight, sex, diet and medical condition of the patient, the route of administration, pharmacological considerations such as the activity, efficacy, pharmacokinetic and toxicology profiles of the drug therapy. Thus, the dosage regimen actually employed may vary widely and therefore may deviate from the preferred dosage set forth in table 4 above.

The invention is further illustrated by the following examples, which are not to be construed as limiting, but merely as an illustration of some preferred features of the invention.

Treating Weight Gain Associated with Drug Therapy for Diabetes

An embodiment of the invention is related to the use of an SCD-1 inhibitor in combination with one or more drug therapies for diabetes, particularly oral antidiabetics, more particularly the gamma isoform of the peroxisome proliferators-activated receptor ("PPAR-γ") agonists, to treat the consistently documented side effect of adverse weight gain. Such a use is especially valuable in the treatment of type 2 diabetes.

The introduction of troglitazone (Rezulin™) in 1997 promised a new era in therapy for diabetes, particularly type 2 diabetes. Troglitazone belonged to a new drug class called thiazolidinediones ("glitazones" for short) that act directly on the root cause of type 2 diabetes by activating the PPAR-γ in adipose tissues, skeletal muscles, and the liver. The end result of PPAR-γ activation is a reduction in hepatic glucose production and increased insulin-dependent glucose uptake in fat and skeletal tissues. (see, American Diabetes Association. Consensus Development Conference on Insulin Resistance. Diabetes Care. 1998; 21:310-314). Two other glitazones, rosiglitazone (Avandia™) and pioglitazone (Actos™), were approved by the U.S. Food & Drug Administration in 1999. Like troglitazone, rosiglitazone and pioglitazone are believed to also be agonists of the PPARγ and their primary mechanism of action is sensitization of tissues to insulin. Increases in body weight have been observed with all classes of glitazones either as monotherapy or in a regime with other anti-diabetic agents like sulfonylurea, metformin, or insulin (see, Lebovits, H, Differentiating members of the thiazolidinedione class: a focus on safety, Diabetes Metab. Res. Rev. 2002; 18:S23-S29) Weight gain associated with low-dose rosigliatzone (4 mg/day) is at about 8 kg/year after one year treatment. (see SmithKline Beecham Pharmaceuticals. Avandia (rosiglitazone maleate) tablets. Prescribing information. Collegeville, Pa.: 2001).

The present invention relates to the discovery that the co-administration of an SCD-1 inhibitor and a "PPAR-γ" agonist such as rosiglitazone, for instance, exerts beneficial effects on the adverse weight gain associated with the rosiglitazone treatment. Studies were designed to evaluate the effects of treatment with an SCD-1 inhibitor and rosiglitazone, as a combination therapy, on adverse weight gains in diabetic rats. The data showed that the adverse weight gain associated with rosiglitazone monotherapy was decreased when an SCD-1 inhibitor was administered in conjunction with rosiglitazone.

The improvement was statistically significant and maintained over the course of co-administration (6 weeks).

Example 1

Effect of SCD-1 Inhibitor and Rosiglitazone Co-Administration on Body Weight This study was designed to evaluate the effects of using a combination of an SCD-1 inhibitor and rosiglitazone on body weight and in addition, if this combination therapy would prevent the adverse weight gain associated with the rosiglitazone treatment alone.

Method

Male Zucker Diabetic Fatty Rats (ZDF) began treatment at the age of 7 weeks of age. Animals were housed three to a cage in a temperature, humidity and light controlled room. The animals were fed a standard rodent diet and had free access to water. Animals were randomized into groups of 9 and placed in the following experimental groups for daily dosing (10:30 am) as described in table 5 below. Animals were weighed three times per week. Food intake was recorded three times per week. XEN 1 is a representative SCD-1 inhibitor compound of the invention. The formulations were:

Vehicle=1% CMC:0.1% Tween 20:10% PG
Rosi-10=rosiglitazone 10 mg/kg in 1% CMC:0.1% Tween 20:10% PG
Rosi-10+XEN1=rosiglitazone 10 mg/kg+XEN1 5 mg/kg in 1% CMC:0.1% Tween 20:10% PG
XEN1=XEN1 5 mg/kg in 1% CMC:0.1% Tween 20:10% PG

TABLE 5

The experimental groups

| | Group | No of Rats | Strain of rat | Dose Vol (mL/kg) | Dose (mg/kg/day) |
|---|---|---|---|---|---|
| I | Vehicle | 9 | ZDF | 3 | 0 |
| II | Rosiglitazone (po) | 9 | ZDF | 3 | 10 |
| III | Rosiglitazone & XEN 1 | 9 | ZDF | 3 | 10 + 5 |
| IV | XEN 1 | 9 | ZDF | 3 | 5 |

Results

The data from this study, which are summarized in table 6 below, demonstrate (1) body weight gain is observed with administration of rosiglitazone, (2) a reduction of the body weight gain associated with the administration of rosiglitazone is seen upon co-administration of the SCD-1 inhibitor, and (3) a loss of body weight associated with the administration of the SCD-1 inhibitor, as compared to the control. Therefore, an SCD-1 inhibitor attenuates the weight gain caused by the rosiglitazone.

TABLE 6

Changes in body weight

| Rat | Treatment | Initial Body Weight (g) | Final Body Weight (g) | Body Weight Gain - 5 week treatment (g) |
|---|---|---|---|---|
| ZDF | Vehicle | 161.4 +/− 3.8 | 326.0 +/− 8.2 | 164.6 +/− 5.6 |
| ZDF | Rosi (10 mg/kg) | 163.4 +/− 2.1 | 485.3 +/− 7.3 | 321.9 +/− 6.5 |
| ZDF | Rosi (10 mg/kg) + XEN103 (5 mg/kg) | 160.0 +/− 3.3 | 398.4 +/− 4.7 | 238.4 +/− 4.6 |
| ZDF | XEN103 (5 mg/kg) | 161.6 +/− 3.9 | 312.2 +/− 5.1 | 150.7 +/− 3.5 |

Statistics: All data are presented as mean +/− SEM. Significance was judged using an unpaired T-test, with values less than 0.05 considered significant FIG. 1 shows the change in body weight of the ZDF rats throughout the 6 weeks study. Rats who received the Rosiglitazone+XEN 1 combination gained less weight than rats who received rosiglitazone alone.

Example 2

Effect of SCD-1 Inhibitor and Rosiglitazone Co-Administration on Desaturation Index in Rats One method of determining efficacy of SCD-1 inhibitors for treatment of adverse weight gain is to directly measure the reduced adverse weight gain. Another suitable method is to indirectly measure the SCD-1 inhibitors impact on inhibition of SCD enzyme by measuring a subject's desaturation index ('DI') after administration of the SCD-1 inhibitors. DI as employed in this specification means the ratio of the product over the substrate for the SCD enzyme as measured from a given tissue sample. This may be calculated using three different equations 18:1n−9/18:0 (oleic acid over stearic acid); 16:1n−7/16:0 (palmitoleic acid over palmitic acid); and/or 16:1n−7+18:1n−7/16:0 (measuring all reaction products of 16:0 desaturation over 16:0 substrate). DI is primarily measured in liver or plasma triglycerides, but may also be measured in other selected lipid fractions from a variety of tissues. DI, generally speaking, is a tool for plasma lipid profiling. A published clinical study in a Dutch cohort showed that a two-fold increase in DI was associated with a four-fold increase in triglycerides (Attie et al, Journal of Lipid Research, 43;1899-1907, 2002) and a 50% increase in Body Mass Index (unpublished observations).

This study was designed to evaluate the effects of using a combination of an SCD-1 inhibitor and rosiglitazone on DI, and validate the correlation of the DI as an indicator of endogenous SCD1 activity, and shown a correlation of high DI with obesity and metabolic syndrome.

Method

ZDF rats from example 1 above were used in this study. Desaturation indexes were calculated from the fatty acid profile of circulating plasma triglycerides. Lipids were extracted from plasma using a slight modification of the procedure developed by Folch et al., Journal of Biological Chemistry 226 (1957) 497-509, 0.5 mL of plasma was combined with 1.0 mL of saline, 2.0 mL of methanol and 4.0 mL of chloroform. An additional 0.5 mL of chloroform containing 0.05 mg/mL of glyceryl-triheptadecanoin as an internal standard were also added. Samples were thoroughly vortexed and the phases separated by centrifugation at 2000 rpm for 8 minutes. The lower organic phase was transferred to a new tube, following which the plasma was re-extracted with an additional 4.0 mL of chloroform. This process was repeated until the plasma had been extracted a total of 3 times with chloroform.

The sample was evaporated to dryness under a gentle stream of nitrogen and the lipid extract resuspended in 0.1 mL of fresh chloroform.

The resuspended extracts were spotted on silica plates and the neutral lipid fractions were separated by high performance thin layer chromatography using a solvent system of 80:20:2 hexane:ethyl ether:acetic acid (v/v/v). The silica containing the triglyceride fraction was recovered from the plate by scraping and the sample transferred to a fresh tube. The triglyceride fatty acids were converted to their methyl esters by heating with 1:3 14% $BF_3$ in methanol:hexane (v/v) at 100° C. for 30 minutes. The methyl esters were extracted from the sample with two equal volumes of pentane. The methyl ester extracts were evaporated to dryness under nitrogen and resuspended in 0.1 mL of hexane.

Samples were analyzed by gas-liquid chromatography on a 30 m×0.25 mm Supelco SP-2380 column. The column temperature was held at 100° C. for 2 minutes, increased to 145° C. at 5° C./min, held for 27 minutes, increased to 170° C. at 5° C./min and held for 10 minutes, increased to 245° C. at 5° C./min and held for an additional 20 minutes.

3 desaturation indexes were calculated from the chromatograms based on absolute peak areas; the ratio of palmitoleic acid to palmitic acid (C16:1n7/C16:0), the ratio of oleic acid to stearic acid (C18:1n9/C18:0) and the ratio of palmitoleic acid and vaccenic acid to palmitic acid (C16:1n7+C18:1n7/C16:0).

Results

The data from this study, which are summarized in table 7 below, demonstrate (1) increases in DI for all lipid fractions analyzed with administration of rosiglitazone, (2) a reduction of DI associated with the administration of rosiglitazone is seen with co-administration of the SCD-1 inhibitor as compared to rosiglitazone alone for all lipid fractions analyzed. Further, we have previously shown in other experiments that SCD-1 inhibitor acts to reduce DI in many strains of rats in a statistically significant fashion and that this is correlated with a reduction in SCD-1 activity. The SCD-1 inhibitor does not significantly reduce DI in this model due to the low baseline DI in the ZDF model compared to other models tested.

specification and/or listed in the Application Data Sheet are incorporated herein by reference, in their entirety, into this application to describe more fully the art to which the invention pertains.

Although the invention has been described with reference to illustrative embodiments, it is to be understood that the invention is not limited to these precise embodiments, and that various changes and modification are to be intended to be encompassed in the appended claims.

What is claimed is:

1. A method for treating adverse weight gain associated with a drug therapy, comprising administering to a subject in need thereof a therapeutically effective amount of a stearoyl-CoA desaturase-1(SCD-1) inhibitor is a compound having the formula (I):

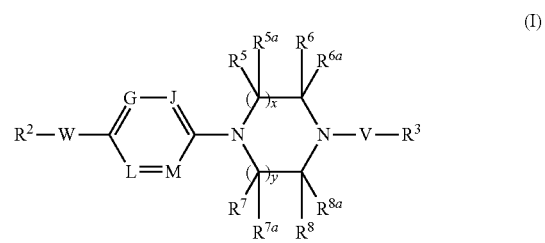

wherein:

x and y are each independently 1, 2 or 3;

W is a direct bond, —N($R^1$)C(O)—, —C(O)N($R^1$)—, —OC(O)N($R^1$)—, —N($R^1$)C(O)N($R^1$)—, —O—, —N($R^1$)—, —S(O)$_t$— (where t is 0, 1 or 2), —N($R^1$)S(O)$_p$— (where p is 1 or 2), —S(O)$_p$N($R^1$)— (where p is 1 or 2), —C(O)—, —OS(O)$_2$N($R^1$)—, —OC(O)—, —C(O)O—, —N($R^1$)C(O)O—, —N$R^1$C(=N$R^{1a}$)N$R^1$—, —N$R^1$C(=S)N$R^1$—, or —C(=N$R^{1a}$)N$R^1$—;

V is —C(O)—, —C(O)O—, —C(S)—, —C(O)N($R^1$)—, —S(O)$_t$— (where t is 0, 1 or 2), —S(O)$_p$N($R^1$)— (where p is 1 or 2), —C($R^{10}$)H—, —N($R^1$)—, —C(=N$R^{1a}$)—, or —O—;

TABLE 7

| Plasma desaturation index (DI) after treatment | | | | |
|---|---|---|---|---|
| C18:1n9/C18:0 | | | | |
| | Vehicle | Rosi-10 | Rosi-10 + XEN 1 | XEN 1 |
| Mean P-Value | 6.203 +/− 1.55 | 9.217 +/− 2.146 a: p = 0.0192 | 4.482 +/− 0.631 a: p = 0.0305, b: p = 0.0004 | 5.874 +/− 0.422 a: p = 0.6821, b: p = 0.0496 |
| C16:1n7/C16:0 | | | | |
| | Vehicle | Rosi-10 | 76310 | XEN 1 |
| Mean P-Value | 0.063 +/− 0.003 | 0.193 +/− 0.013 a: p = 0.0006 | 0.083 +/− 0.003 a: p = 0.0013, b: p = 0.0029 | 0.043 +/− 0.004 a: p = 0.7675, b: p = 0.0079 |

All data are mean +/− standard deviation
a: compare to vehicle (two-tailed unpaired t-test)
b: compare to Rosiglitazone-10 mpk (two-tailed unpaired t-test)
Vehicle = 1% CMC: 0.1% Tween 20: 10% PG
Rosi-10 = rosiglitazone 10 mg/kg in 1% CMC: 0.1% Tween 20: 10% PG
Rosi-10 + XEN1 = rosiglitazone 10 mg/kg + XEN1 5 mg/kg in 1% CMC: 0.1% Tween 20: 10% PG
XEN1 = XEN1 5 mg/kg in 1% CMC: 0.1% Tween 20: 10% PG All of the U.S. patents, U.S. patent application publications, U.S. patent applications, foreign patents, foreign patent applications and non-patent publications referred to in this G, J, L and M are each independently selected from —N= or —C($R^4$)=; provided that at most two of G, J, L and M are —N=, each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

each $R^{1a}$ is independently selected from the group consisting of hydrogen, $C_1$-$C_{12}$alkyl, $C_4$-$C_{12}$cycloalkylalkyl, $C_7$-$C_{19}$aralkyl, $OR^1$, and cyano;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

each $R^4$ is independently selected from hydrogen, fluoro, chloro, methyl, methoxy, trifluoromethyl, cyano, nitro or —$N(R^9)_2$;

each $R^5$, $R^{5a}$, $R^6$, $R^{6a}$, $R^7$, $R^{7a}$, $R^8$ and $R^{8a}$ is independently selected from hydrogen or $C_1$-$C_3$alkyl;

or $R^5$ and $R^{5a}$ together, or $R^6$ and $R^{6a}$ together, or $R^7$ and $R^{7a}$ together, or $R^8$ and $R^{8a}$ together are an oxo group, provided that when V is —C(O)—, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

or one of $R^5$, $R^{5a}$, $R^6$, and $R^{6a}$ together with one of $R^7$, $R^{7a}$, $R^8$ and $R^{8a}$ form an alkylene bridge, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

$R^{10}$ is hydrogen or $C_1$-$C_3$alkyl; and each $R^9$ is independently selected from hydrogen or $C_1$-$C_6$alkyl;

provided that when G, J and L are each —C($R^4$) where each $R^4$ is hydrogen, and M is —N═, and x is 1 or 2 and y is 1; W cannot be —N($R^1$)C(O)—;

a stereoisomer, enantiomer or tautomer thereof, a pharmaceutically acceptable salt thereof in conjunction with a pharmaceutically acceptable diluent or carrier.

2. The method of claim 1, wherein said drug therapy is selected from the group consisting of anti-diabetics, anti-depressants, anti-psychotics, anti-convulsants, anti-epileptics, oral contraceptives, cancer therapy, preventative migraine therapy, therapy for systemic inflammatory conditions, endometriosis therapy, osteoporosis therapy, hair growth therapy, and HIV therapy.

3. The method of claim 1, wherein said drug therapy is an anti-diabetic therapy.

4. The method of claim 3, wherein said anti-diabetic therapy is selected from the group consisting of a sulfonylurea, a meglitinide, a PPAR-γ agonist, and insulin.

5. The method of claim 4, wherein said PPAR-γ agonist is rosiglitazone or pioglitazone.

6. The method of claim 1, wherein said drug therapy is an anti-depressant selected from the group consisting of selective serotonin reuptake inhibitors, monoamine oxidase inhibitors, and tricyclic inhibitors.

7. The method of claim 1, wherein said drug therapy is an anti-psychotic selected from second generation anti-psychotics.

8. The method of claim 1, wherein said drug therapy is for cancer therapy selected from chemotherapy and hormone replacement therapy.

9. The method of claim 1, wherein said drug therapy and said SCD-1 inhibitor are administered together.

10. The method of claim 1, wherein said drug therapy and said SCD-1 inhibitor are administered sequentially.

11. The method of claim 1, wherein said subject is a mammal.

12. The method of claim 11, wherein said mammal is a human.

13. The method of claim 1, wherein said therapeutically effective amounts of SCD-1 inhibitor is about 0.01 mg/kg to about 500 mg/kg per day.

14. The method of claim 13, wherein said therapeutically effective amounts of SCD-1 inhibitor is about 0.05 mg/kg to about 100 mg/kg per day.

15. The method of claim 14, wherein said therapeutically effective amounts of SCD-1 inhibitor is about 0.20 mg/kg to about 50 mg/kg per day.

16. The method of claim 15, wherein said therapeutically effective amounts of SCD-1 inhibitor is about 0.50 mg/kg to about 20 mg/kg per day.

17. The method of claim 16, wherein said therapeutically effective amounts of SCD-1 inhibitor is about 1.0 mg/kg to about 2.0 mg/kg per day.

18. The method of claim 1, wherein said SCD-1 inhibitor is effective to inhibit or reverse the adverse weight gain.

* * * * *